United States Patent
Vokits et al.

(10) Patent No.: US 12,060,341 B2
(45) Date of Patent: *Aug. 13, 2024

(54) SPIROHEPTANYL HYDANTOINS AS ROCK INHIBITORS

(71) Applicant: BRISTOL-MYERS SQUIBB COMPANY, Princeton, NJ (US)

(72) Inventors: Benjamin P. Vokits, New York City, NY (US); Scott A. Shaw, Lawrence Township, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/888,600

(22) Filed: Aug. 16, 2022

(65) Prior Publication Data
US 2024/0092755 A1    Mar. 21, 2024

Related U.S. Application Data

(62) Division of application No. 16/629,784, filed as application No. PCT/US2018/041563 on Jul. 11, 2018, now Pat. No. 11,447,487.

(60) Provisional application No. 62/531,604, filed on Jul. 12, 2017.

(51) Int. Cl.
| | |
|---|---|
| *C07D 401/12* | (2006.01) |
| *C07D 401/14* | (2006.01) |
| *C07D 403/12* | (2006.01) |
| *C07D 405/14* | (2006.01) |
| *C07D 471/04* | (2006.01) |

(52) U.S. Cl.
CPC ......... *C07D 401/12* (2013.01); *C07D 401/14* (2013.01); *C07D 403/12* (2013.01); *C07D 405/14* (2013.01); *C07D 471/04* (2013.01)

(58) Field of Classification Search
CPC .. C07D 401/14; C07D 403/12; C07D 405/14; C07D 471/04
See application file for complete search history.

(56) References Cited

U.S. PATENT DOCUMENTS

| | | | |
|---|---|---|---|
| 8,742,116 B2 | 6/2014 | Plettenburg et al. | |
| 11,078,197 B2 * | 8/2021 | Glunz | A61P 35/00 |
| 11,447,487 B2 * | 9/2022 | Vokits | C07D 471/04 |
| 11,673,886 B2 * | 6/2023 | Glunz | A61P 9/00 |
| | | | 514/210.16 |

FOREIGN PATENT DOCUMENTS

| | | |
|---|---|---|
| EP | 2025676 A1 | 2/2009 |
| WO | WO2014113620 A2 | 7/2014 |
| WO | WO2014134388 A1 | 9/2014 |
| WO | WO2014134391 A1 | 9/2014 |
| WO | WO2015002915 A1 | 1/2015 |
| WO | WO2015002926 A1 | 1/2015 |
| WO | WO-2016010950 A1 * | 1/2016 ........... A61K 31/502 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2017205709 A1 | 11/2017 |
| WO | WO2018009622 A1 | 1/2018 |
| WO | WO2018009625 A1 | 1/2018 |
| WO | WO2018009627 A1 | 1/2018 |
| WO | WO2018102325 A1 | 6/2018 |

(Continued)

OTHER PUBLICATIONS

Pan et al., 18 Drug Discovery Today, 1323-1333 (2013) (Year: 2013).*
Wang et.al, 17(12) Neural Regen Res. 2623-2631(2022). (Year: 2022).*
S. Kim et al., International Journal of Molecular Sciences, 1-21 (2021) (Year: 2021).*

*Primary Examiner* — Theodore R. Howell
(74) *Attorney, Agent, or Firm* — Hong Liu

(57) ABSTRACT

The present invention provides compounds of Formula (I):

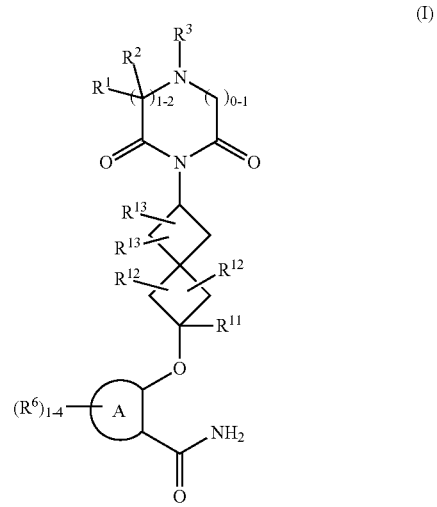

or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

17 Claims, No Drawings

(56) References Cited

FOREIGN PATENT DOCUMENTS

| | | |
|---|---|---|
| WO | WO2019014300 A1 | 1/2019 |
| WO | WO2019014303 A1 | 1/2019 |
| WO | WO2019014308 A1 | 1/2019 |
| WO | WO2019089868 A1 | 5/2019 |

* cited by examiner

SPIROHEPTANYL HYDANTOINS AS ROCK INHIBITORS

CROSS REFERENCE TO RELATED APPLICATIONS

This application is a divisional of U.S. Ser. No. 16/629,784 filed on Jan. 9, 2020, now allowed, which is a 371 International Application of PCT/US2018/041563, filed Jul. 11, 2018, which is entitled to priority pursuant to 35 U.S.C. § 119(e) to U.S. provisional patent application No. 62/531,604, filed Jul. 12, 2017, which is incorporated herein in its entirety.

FIELD OF THE INVENTION

The present invention relates generally to novel spiroheptanyl hydantoins and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovascular Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovascular Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vase. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-

74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer's disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

There are many reports of ROCK inhibitors under investigation (see, for example, US 2012/0122842 A1, US 2010/0041645 A1, US 2008/0161297 A1, and Hu, E. et al., *Exp. Opin. Ther. Targets*, 9:715-736 (2005)). Reports also include WO2014/113620, WO 2014/134388, WO 2014/134391, WO2015/002915, WO2015/002926, WO2016/010950, WO2016/028971, WO2016/112236, and WO2016/144936, all of which are assigned to the present applicant. However, fasudil is the only marketed ROCK inhibitor at this time. An i.v. formulation was approved in Japan for treatment of cerebral vasospasm. Thus, there remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel spiroheptanyl hydantoins and their analogues, including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

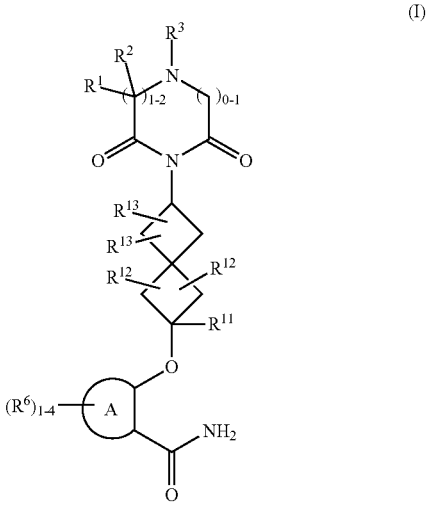

or stereoisomers, tautomers, pharmaceutically acceptable salts, solvates, or prodrugs thereof, wherein Ring A is heteroaryl comprising carbon and 1-2 nitrogen atoms;

$R^1$ is selected from H, $C_{1-7}$ alkyl, $C_{2-7}$ alkenyl, $C_{2-7}$ alkynyl, —$(CR^4R^4)_n NR^5R^5$, —$(CR^4R^4)_n C_{3-10}$ carbocycle and —$(CR^4R^4)_n$-4- to 15-membered heterocycle comprising carbon atoms and 1-4 heteroatoms selected from N, $NR^8$, O, and $S(O)_p$, wherein said alkyl, alkenyl, alkynyl, carbocycle, and heterocycle are substituted with 1-4 $R^7$;

$R^2$ is H; or $R^1$ and $R^2$ are taken together to form =O; or $R^1$ and $R^2$ are taken together with the carbon atom, to which they are both attached, to form a carbocycle or heterocycle wherein said carbocycle, and heterocycle are substituted with 1-4 $R^7$;

$R^3$ is selected from H, $C_{1-4}$ alkyl, $C_{2-4}$ alkenyl, —$(CR^4R^4)_{1-4}$—$NR^5R^5$, —$(CR^4R^4)_n C_{3-10}$ carbocycle and —$(CR^4R^4)_n$-4- to 15-membered heterocycle comprising carbon atoms and 1-4 heteroatoms selected from N, $NR^8$, O, and $S(O)_p$, wherein said alkyl, alkenyl, carbocycle, and heterocycle are substituted with 1-4 $R^7$; provided that $R^1$, $R^2$, and $R^3$ are not all H;

alternatively, $R^1$ and $R^3$ together form a fused ring;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$ and $R^5$ are taken together with the nitrogen atom to which they are attached to form a 4- to 15-membered heterocycle substituted with 1-4 $R^7$;

$R^6$, at each occurrence, is independently selected from H, halogen, $C_{1-6}$ alkyl, $C_{2-6}$ alkenyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, a carbocycle, and a heterocycle, wherein said alkyl, alkenyl, alkoxy, alkylthio, haloalkyl, carbocycle, and heterocycle are substituted with 0-4 $R^9$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —$S(O)_2$-carbocycle, —$S(O)_2$-heterocycle, —NHC O-carbocycle, —NHCO-heterocycle, —$NHCOO(CH_2)_n$carbocycle, —$NHCOO(CH_2)_n$-heterocycle, —CONH-carbocycle, —CONH-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, —$(CH_2)_n$—C(O)$C_{1-4}$alkyl, —$(CH_2)_n$—C(O)carbocycle, —$(CH_2)_n$—C(O)heterocycle, —$(CH_2)_n$—$C(O)NR^aR^a$, —$(CH_2)_n$—$NR^aC(O)$ $C_{1-4}$alkyl, —$(CH_2)_n$—$C(O)OC_{1-4}$alkyl, —$(CH_2)_n$—$C(O)C_{1-4}$alkyl, —$(CH_2)_n$—$C(O)O(CH_2)_n$ carbocycle, —$(CH_2)_n$—$C(O)O(CH_2)_n$-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), —$(CHR^{10})_n NR^aR^a$, $S(O)_p(C_{1-4}$ alkyl), —$(CHR^{10})_n CONR^aR^a$, —$(CHR^{10})_n NR^aCO(C_{1-4}$ alkyl), —$(CHR^{10})_n OCONR^a$ $(CH_2)_n CO_2R^a$, $S(O)_p C_{1-4}$alkyl, $S(O)_p NR^aR^a$, —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, —OH, CN, —$CO_2H$, —$CO_2(C_{1-4}$ alkyl), —$CO(C_{1-4}$ alkyl), —$CONH_2$, —$CONH(C_{1-4}$ alkyl), and —CON$(C_{1-4}$ alkyl)$_2$;

$R^{12}$ and $R^{13}$ are independently selected from H, OH, —$OC_{1-3}$ alkyl substituted with 0-4 $R^d$, and $C_{1-3}$ alkyl with substituted with 0-4 $R^d$;

$R^a$, at each occurrence, is independently selected from H, $C_{1-4}$ alkyl, —$(CH_2)_n OH$, $CO(C_{1-4}$ alkyl), $COCF_3$, $CO_2$$(C_{1-4}$ alkyl), —$CONH_2$, —CONH—$C_{1-4}$ alkylene-$CO_2$ $(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2H$, $CO_2(C_{1-4}$ alkyl), $CONH_2$, —$CONH(C_{1-4}$ alkyl), —$CON(C_{1-4}$ alkyl)$_2$, —CONH—$C_{1-4}$ alkylene-$O(C_{1-4}$ alkyl), —CONH—$C_{1-4}$ alkylene-$NH(C_{1-4}$ alkyl), —CONH—$C_{1-4}$ alkylene-$N(C_{1-4}$ alkyl)$_2$, —$C_{1-4}$ alkylene-O—P(O)$(OH)_2$, —$NHCO_2(C_{1-4}$ alkyl), —$R^c$, $COR^c$, $CO_2R^c$, and $CONHR^c$, wherein said alkyl and alkoxy are substituted with $R^d$.

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$, wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (II):

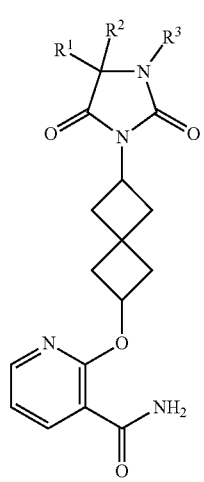

(II)

or stereoisomers, tautomers, pharmaceutically acceptable salts, solvates, or prodrugs thereof, wherein $R^1$ is selected from H, $C_{1-7}$ alkyl, $C_{2-7}$ alkenyl, $C_{2-7}$ alkynyl, $-(CR^4R^4)_n NR^5R^5$, $-(CR^4R^4)_n C_{3-10}$ carbocycle and $-(CR^4R^4)_n$-4- to 15-membered heterocycle comprising carbon atoms and 1-4 heteroatoms selected from N, $NR^8$, O, and $S(O)_p$, wherein said alkyl, alkenyl, carbocycle, and heterocycle are substituted with 1-4 $R^7$;

$R^2$ is H; or $R^1$ and $R^2$ are taken together to form =O; or $R^1$ and $R^2$ together with the carbon atom, to which they are both attached, to form $C_{3-6}$ cycloalkyl substituted with 1-4 $R^7$;

$R^3$ is H;

$R^4$, at each occurrence, is independently selected from H and $C_{1-4}$ alkyl substituted with 0-4 $R^9$;

$R^5$ and $R^5$ are taken together with the nitrogen atom to which they are attached to form a 4- to 15-membered heterocycle substituted with 1-4 $R^7$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, $-(CH_2)_n-CO_2H$, $-(CH_2)_n-CO_2(C_{1-4}$ alkyl), $-(CH_2)_n-NR^8R^8$, $-NHCOH$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-CH_2NHCO_2(C_{1-4}$ alkyl), $-NHC(O)NR^8R^8$, $-NHSO_2(C_{1-4}$ alkyl), $-S(O)_p(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-S(O)_2$-carbocycle, $-S(O)_2$-heterocycle, $-NHC$ O-carbocycle, $-NHCO$-heterocycle, $-CONH$-carbocycle, $-CONH$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, $-(CH_2)_n-C(O)C_{1-4}$alkyl, $-(CH_2)_n-C(O)$carbocycle, $-(CH_2)_n-C(O)$heterocycle, $-(CH_2)_n-C(O)NR^aR^a$, $-(CH_2)_n-NR^aC(O)C_{1-4}$alkyl, $-(CH_2)_n-C(O)OC_{1-4}$alkyl, $-(CH_2)_n-C(O)C_{1-4}$alkyl, $-(CH_2)_n-C(O)O$-carbocycle, $-(CH_2)_n-C(O)O$-heterocycle, $-(CH_2)_n-SO_2$alkyl, $-(CH_2)_n SO_2$carbocycle, $-(CH_2)_n-SO_2$heterocycle, $-(CH_2)_n-SO_2NR^aR^a$, $-(CH_2)_n$-carbocycle, and $-(CH_2)_n$-heterocycle, wherein said alkyl, carbocycle, and heterocycle are substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), $-(CHR^{10})_n NR^aR^a$, $S(O)_p(C_{1-4}$ alkyl), $-(CHR^{10})_n CONR^aR^a$, $-(CHR^{10})_n NR^aCO(C_{1-4}$ alkyl), $-(CHR^{10})_n OCONR^a$ $(CH_2)_n CO_2R^a$, $S(O)_p C_{1-4}$alkyl, $S(O)_p NR^aR^a$, $-O(CHR^{10})_n$carbocycle, $-O(CHR^{10})_n$heterocycle, $-O(CHR^c)_n NR^aR^a$, and $-(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^a$, at each occurrence, is independently selected from H, $C_{1-4}$ alkyl, $-(CH_2)_n OH$, $CO(C_{1-4}$ alkyl), $COCF_3$, $CO_2(C_{1-4}$ alkyl), $-CONH_2$, $-CONH-C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2H$, $CO_2(C_{1-4}$ alkyl), $CONH_2$, $-CONH(C_{1-4}$ alkyl), $-CON(C_{1-4}$ alkyl)$_2$, $-CONH-C_{1-4}$ alkylene-$O(C_{1-4}$ alkyl), $-CONH-C_{1-4}$ alkylene-$NH(C_{1-4}$ alkyl), $-CONH-C_{1-4}$ alkylene-$N(C_{1-4}$ alkyl)$_2$, $-C_{1-4}$ alkylene-$O-P(O)$ $(OH)_2$, $-NHCO_2(C_{1-4}$ alkyl), $-R^c$, $COR^c$, $CO_2R^c$, and $CONHR^c$, wherein said alkyl and alkoxy are substituted with $R^d$;

$R^c$, at each occurrence, is independently selected from $-(CH_2)_n-C_{3-6}$ cycloalkyl, $-(CH_2)_n$-phenyl, and $-(CH_2)_n$-5- to 6-membered heterocycle containing carbon atoms and 1-4 heteroatoms selected from the group consisting of: N, NH, $N(C_{1-4}$ alkyl), O, and $S(O)_p$, wherein each ring moiety is substituted with 0-2 $R^d$;

$R^d$, at each occurrence, is independently selected from =O, halogen, $-OH$, $C_{1-4}$ alkyl, $NH_2$, $NH(C_{1-4}$ alkyl), $N(C_{1-4}$ alkyl)$_2$, $C_{1-4}$ alkoxy, and $-NHCO(C_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (II):

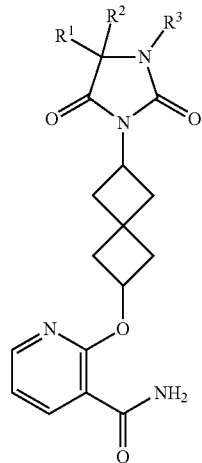
(II)

or stereoisomers, tautomers, pharmaceutically acceptable salts, solvates, or prodrugs thereof, wherein $R^1$ is selected from H and —$(CH_2)_{1-4}$-phenyl;

$R^2$ is H; alternatively, $R^1$ and $R^2$ are taken together to form =O;

$R^3$ is selected from $C_{1-7}$ alkyl, —$(CH_2)_{1-4}NR^5R^5$, —$(CH_2)_nC_{3-8}$ carbocycle selected from

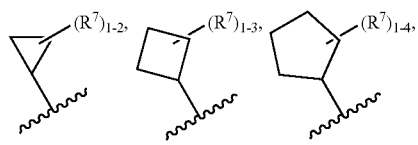

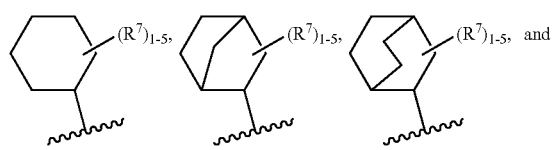

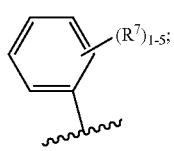

$R^5$ and $R^5$ are taken together with the nitrogen atom to which they are attached to form a 4- to 15-membered heterocycle selected from

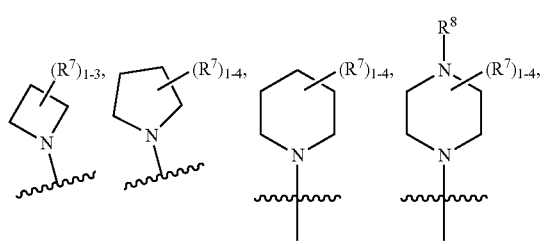

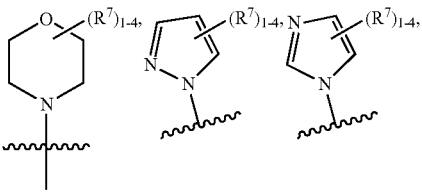

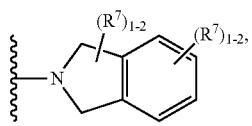

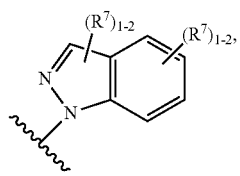

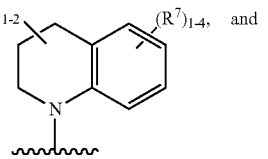

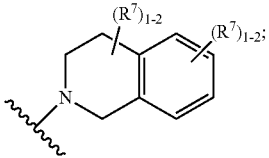

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —NHCO($C_{1-4}$ alkyl), —NHCO$_2$($C_{1-4}$ alkyl), —NHSO$_2$($C_{1-4}$ alkyl), —S(O)$_p$($C_{1-4}$ alkyl), —SO$_2$NH$_2$, —SO$_2$NH($C_{1-4}$ alkyl), —SO$_2$N($C_{1-4}$ alkyl)$_2$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, $NR^8$, O, and S(O)$_p$, wherein said alkyl, alkenyl, alkynyl, alkoxy, carbocycle, and heterocycle are substituted with 0-4 $R^9$;

$R^9$, at each occurrence, is independently selected from halogen, OH, =O, CN, $C_{1-4}$ alkyl, and $C_{1-4}$ alkoxy;

n, at each occurrence, is independently selected from 0, 1, 2, 3, and 4; and p, at each occurrence, is independently selected from 0, 1, and 2.

In another aspect, the present invention provides compounds of Formula (III):

(III)

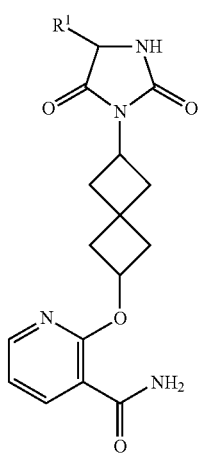

or stereoisomers, tautomers, pharmaceutically acceptable salts, solvates, or prodrugs thereof, wherein $R^1$ is selected from $C_{1-6}$ alkyl, $C_{2-7}$ alkenyl, and $C_{2-7}$ alkynyl, wherein said alkyl, alkenyl, and alkynyl are substituted with 1-4 $R^7$;

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —NHCO($C_{1-4}$ alkyl), —NHCO$_2$($C_{1-4}$ alkyl), —NHSO$_2$($C_{1-4}$ alkyl), —S(O)$_2$ ($C_{1-4}$ alkyl), —SO$_2$NH$_2$, —SO$_2$NH($C_{1-4}$ alkyl), —SO$_2$N($C_{1-4}$ alkyl)$_2$, wherein said alkyl, alkenyl, alkynyl, and alkoxy are substituted with 0-4 $R^9$; and $R^9$, at each occurrence, is independently selected from halogen, OH, =O, CN, $C_{1-4}$ alkyl, and $C_{1-4}$ alkoxy.

In another aspect, the present invention provides compounds of Formula (III):

(III)

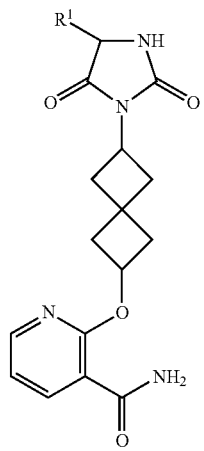

or stereoisomers, tautomers, pharmaceutically acceptable salts, solvates, or prodrugs thereof, wherein $R^1$ is —(CH$_2$)$_{1-4}$—$C_{3-6}$ carbocycle wherein said carbocycle is selected from

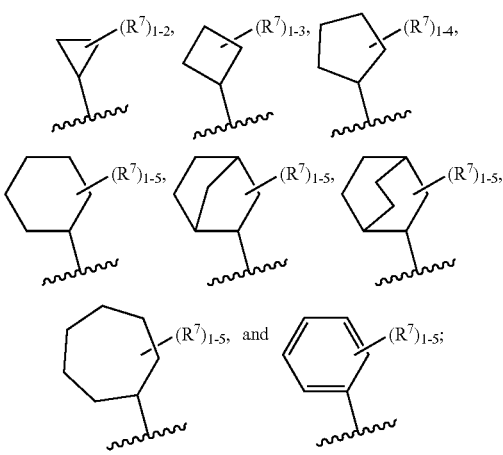

$R^7$, at each occurrence, is independently selected from H, =O, halogen, $C_{1-7}$ alkyl, $C_{1-4}$ alkoxy, CN, OH, $CHF_2$, $CF_3$, —(CH$_2$)$_n$—CO$_2$H, —(CH$_2$)$_n$—CO$_2$($C_{1-4}$ alkyl), wherein said alkyl, alkoxy, are substituted with 0-4 $R^9$;

$R^9$, at each occurrence, is independently selected from halogen, OH, =O, CN, NO$_2$, $C_{1-4}$ alkyl, $C_{1-4}$ alkoxy, CO($C_{1-4}$ alkyl), CO$_2$H, and CO$_2$($C_{1-4}$ alkyl); and n, at each occurrence, is independently selected from 0, 1, 2, 3, and 4.

In another aspect, the present invention provides compounds of Formula (III):

(III)

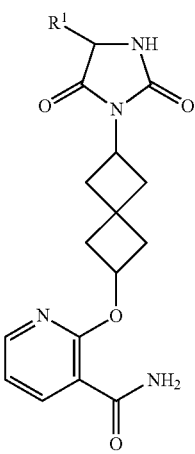

or stereoisomers, tautomers, pharmaceutically acceptable salts, solvates, or prodrugs thereof, wherein $R^1$ is —(CH$_2$)$_{1-4}$-4- to 15-membered heterocycle selected from

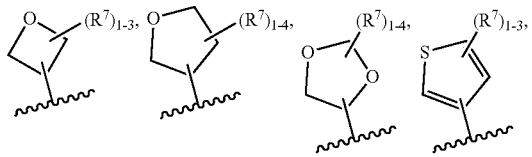

-continued

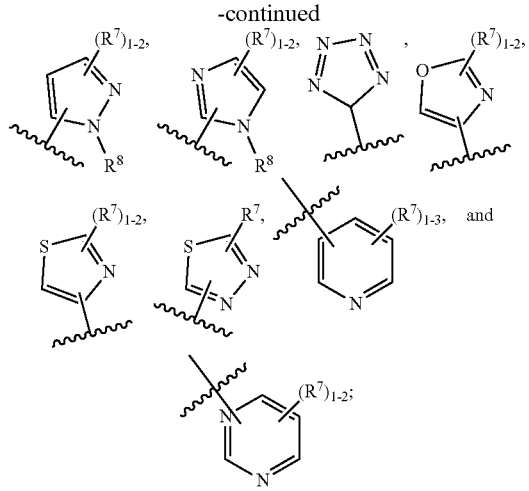

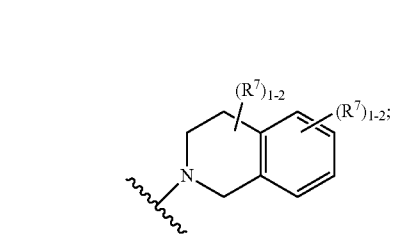

R[7], at each occurrence, is independently selected from H, =O, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —O($CH_2$)$_n$-carbocycle, —O($CH_2$)$_n$-heterocycle, —NHCO-carbocycle, —NHCO-heterocycle, —($CH_2$)$_n$-carbocycle, and —($CH_2$)$_n$-heterocycle comprising carbon atoms and 1-4 heteroatoms selected from N, NR[8], O, and S(O)$_p$, wherein said alkyl, alkenyl, alkynyl, alkoxy, carbocycle, and heterocycle are substituted with 0-4 R[9];

R[8], at each occurrence, is independently selected from H and $C_{1-6}$ alkyl substituted with 0-4 R[9];

R[9], at each occurrence, is independently selected from halogen, OH, =O, CN, $NO_2$, $C_{1-4}$ alkyl, $C_{1-4}$ alkoxy, CO($C_{1-4}$ alkyl), $CO_2H$, and $CO_2$($C_{1-4}$ alkyl); and n, at each occurrence, is independently selected from 0, 1, 2, 3, and 4.

In another aspect, the present invention provides compounds of Formula (III):

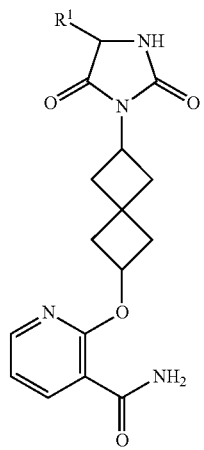

(III)

or stereoisomers, tautomers, pharmaceutically acceptable salts, solvates, or prodrugs thereof, wherein R[1] is —($CH_2$)$_{1-4}$NR[5]R[5];

R[5] and R[5] are taken together with the nitrogen atom to which they are attached to form a 4- to 15-membered heterocycle selected from R[7], at each occurrence, is independently selected from H, =O, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —($CH_2$)$_n$—$CO_2H$, —($CH_2$)$_n$—$CO_2$($C_{1-4}$ alkyl), wherein said alkyl, alkenyl, alkynyl, alkoxy, carbocycle, and heterocycle are substituted with 0-4 R[9];

R[9], at each occurrence, is independently selected from halogen, OH, =O, CN, $NO_2$, $C_{1-4}$ alkyl, $C_{1-4}$ alkoxy, CO($C_{1-4}$ alkyl), $CO_2H$, and $CO_2$($C_{1-4}$ alkyl); and n, at each occurrence, is independently selected from 1, 2, 3, and 4.

In another aspect, the present invention provides compounds of Formula (IV):

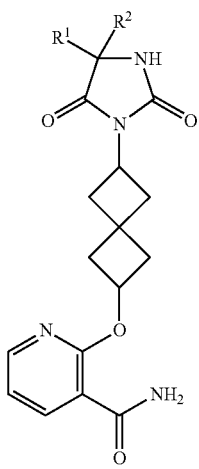

(IV)

or stereoisomers, tautomers, pharmaceutically acceptable salts, solvates, or prodrugs thereof, wherein $R^1$ and $R^2$ are taken together with the carbon atom they are both attached to form cyclobutyl, cyclopentyl, and cyclohexyl, wherein said cyclobutyl, cyclopentyl, and cyclohexyl are substituted with 1-4 $R^7$;

$R^7$, at each occurrence, is independently selected from H, =O, halogen, phenyl substituted with 0-4 $R^9$; and $R^9$, at each occurrence, is independently selected from halogen, OH, CN, $C_{1-4}$ alkyl, and $C_{1-4}$ alkoxy.

In another aspect, the present invention provides compounds of Formula (V):

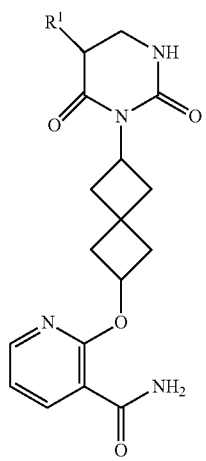

(V)

or stereoisomers, tautomers, pharmaceutically acceptable salts, solvates, or prodrugs thereof, wherein $R^1$ is $C_{1-7}$ alkyl substituted with 1-4 $R^7$;

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —NHCO($C_{1-4}$ alkyl), —NHCO$_2$($C_{1-4}$ alkyl), —NHSO$_2$($C_{1-4}$ alkyl), —S(O)$_p$ ($C_{1-4}$ alkyl), —SO$_2$NH$_2$, —SO$_2$NH($C_{1-4}$ alkyl), —SO$_2$N($C_{1-4}$ alkyl)$_2$, wherein said alkyl, alkenyl, alkynyl, and alkoxy are substituted with 0-4 $R^9$; and $R^9$, at each occurrence, is independently selected from halogen, OH, CN, $C_{1-4}$ alkyl, and $C_{1-4}$ alkoxy.

In another aspect, the present invention provides compounds of Formula (VI):

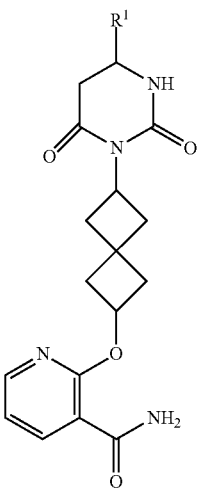

(VI)

or stereoisomers, tautomers, pharmaceutically acceptable salts, solvates, or prodrugs thereof, wherein $R^1$ is selected from $C_{1-7}$ alkyl, $C_{2-4}$ alkenyl, and —(CH$_2$)$_n$ $C_{3-10}$ carbocycle and —(CH$_2$)$_n$-4- to 15-membered heterocycle comprising carbon atoms and 1-4 heteroatoms selected from N, NR$^8$, O, and S(O)$_p$, wherein said alkyl, alkenyl, carbocycle, and heterocycle are substituted with 1-4 $R^7$;

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —NHCO($C_{1-4}$ alkyl), —NHCO$_2$($C_{1-4}$ alkyl), —NHSO$_2$($C_{1-4}$ alkyl), —S(O)$_p$ ($C_{1-4}$ alkyl), —SO$_2$NH$_2$, —SO$_2$NH($C_{1-4}$ alkyl), —SO$_2$N($C_{1-4}$ alkyl)$_2$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 $R^9$;

$R^9$, at each occurrence, is independently selected from halogen, OH, =O, CN, $C_{1-4}$ alkyl, and $C_{1-4}$ alkoxy;

n, at each occurrence, is independently selected from 0, 1, 2, 3, and 4; and p, at each occurrence, is independently selected from 0, 1, and 2.

In another aspect, the present invention provides compounds of Formula (VII):

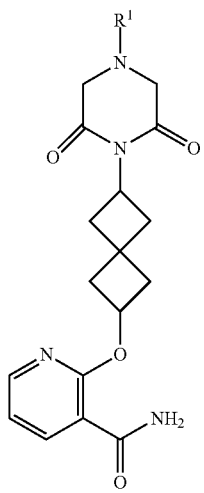

(VII)

or stereoisomers, tautomers, pharmaceutically acceptable salts, solvates, or prodrugs thereof, wherein $R^3$ is selected from $C_{1-7}$ alkyl substituted with 1-4 $R^7$ and —$(CH_2)_n C_{3-8}$ carbocycle selected from

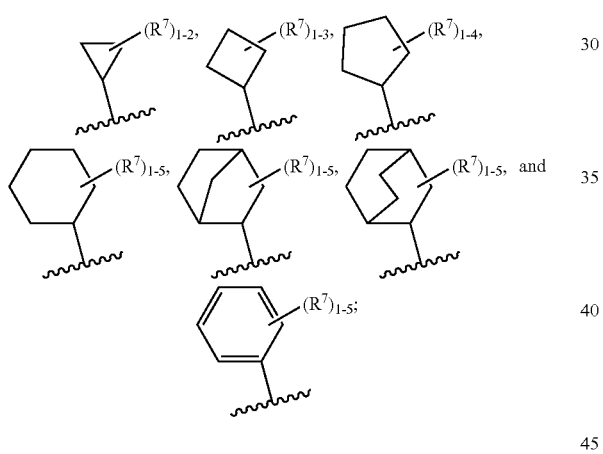

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —NHCO($C_{1-4}$ alkyl), —$NHCO_2$($C_{1-4}$ alkyl), —$NHSO_2$($C_{1-4}$ alkyl), —$S(O)_p$ ($C_{1-4}$ alkyl), —$SO_2NH_2$, —$SO_2NH(C_{1-4}$ alkyl), —$SO_2N(C_{1-4}$ alkyl)$_2$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^9$, at each occurrence, is independently selected from halogen, OH, =O, CN, and $C_{1-4}$ alkyl, $C_{1-4}$ alkoxy;

n, at each occurrence, is independently selected from 0, 1, 2, 3, and 4; and p, at each occurrence, is independently selected from 0, 1, and 2.

In another aspect, the present invention provides compounds of Formula (VIII):

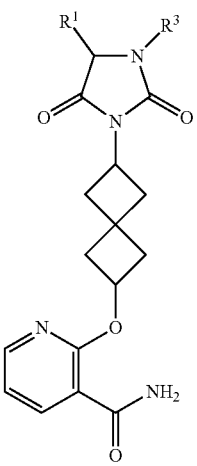

(VIII)

or stereoisomers, tautomers, pharmaceutically acceptable salts, solvates, or prodrugs thereof, wherein $R^1$ and $R^3$ form a fused 5- to 6-membered ring.

In another aspect, the present invention provides compounds of Formula (IX):

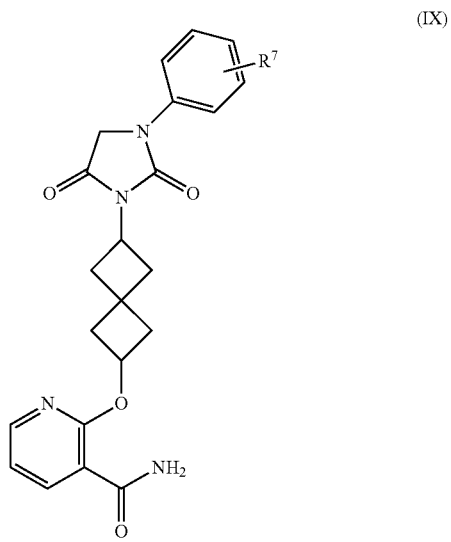

(IX)

or stereoisomers, tautomers, pharmaceutically acceptable salts, solvates, or prodrugs thereof, wherein $R^7$, at each occurrence, is independently selected from H, halogen, $C_{1-7}$ alkyl, $C_{1-4}$ alkoxy, CN, OH, $CHF_2$, $CF_3$, —$S(O)_p(C_{1-4}$ alkyl), —$SO_2NH_2$, —$SO_2NH(C_{1-4}$ alkyl), —$SO_2N(C_{1-4}$ alkyl)$_2$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkoxy, carbocycle, and heterocycle are substituted with 0-4 $R^9$;

$R^9$, at each occurrence, is independently selected from halogen, OH, =O, CN, $C_{1-4}$ alkyl, and $C_{1-4}$ alkoxy;

n, at each occurrence, is independently selected from 0, 1, 2, 3, and 4; and p, at each occurrence, is independently selected from 0, 1, and 2.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments.

For example, in one non-limiting embodiment,

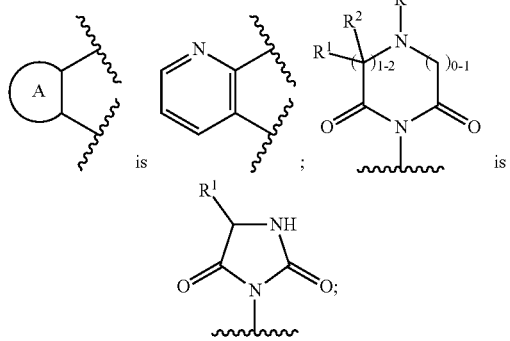

$R^1$ is selected from —$(CH_2)_{1-2}$—$C_{3-6}$cycloalkyl (optionally substituted with F),

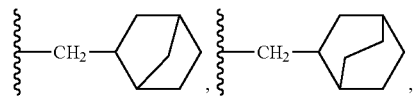

—$(CH_2)_{1-2}$-phenyl, —$(CH_2)_{1-2}$-heterocycle (optionally substituted with $C_{1-4}$ alkyl), $C_{1-6}$ alkyl (optionally substituted with F, OH, $C_{1-4}$ alkoxy (optionally substituted with F), $NHCO_2(C_{1-4}alkyl)$, $SC_{1-4}alkyl$, $S(O)_2NH_2$, $OCH_2$-phenyl), $C_{2-4}$ alkenyl, and $C_{2-4}$ alkynyl.

In another non-limiting embodiment,

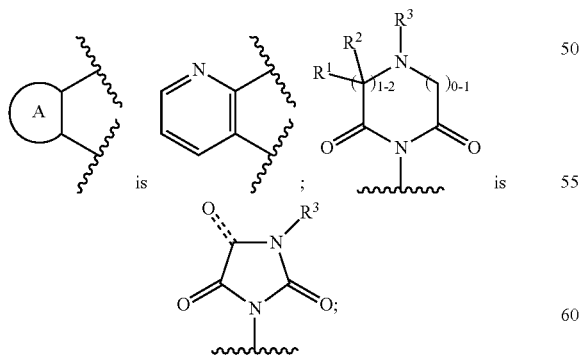

$R^3$ is selected from —$(CH_2)_{1-2}$—$C_{3-6}$cycloalkyl, —$(CH_2)_{0-2}$-phenyl, and $C_{1-6}$ alkyl optionally substituted with F, OH, $C_{1-4}$ alkoxy (optionally substituted with F), $NHCO_2(C_{1-4}alkyl)$, $SC_{1-4}alkyl$, $S(O)_2NH_2$, $OCH_2$-phenyl).

In another non-limiting embodiment,

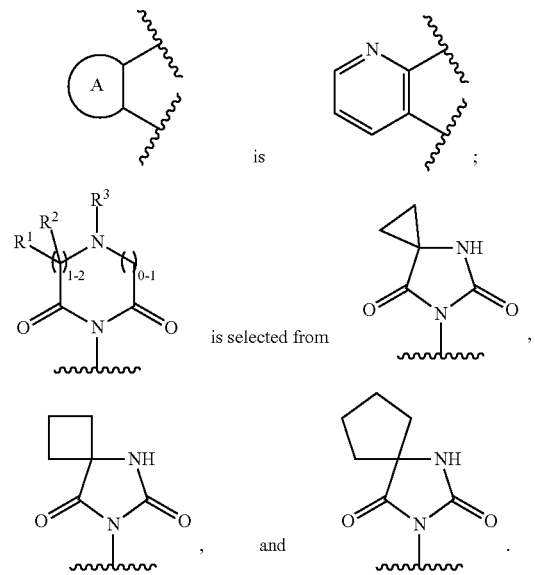

In another non-limiting embodiment,

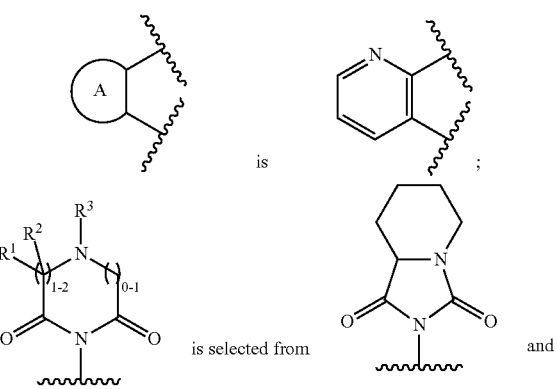

In another non-limiting embodiment,

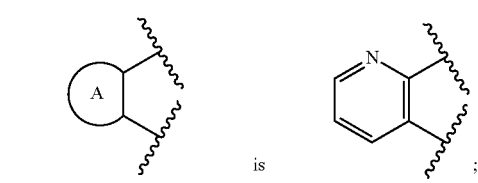

-continued

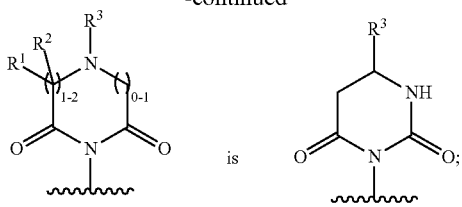
is
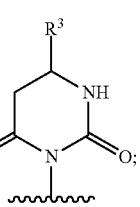

$R^1$ is selected from —$(CH_2)_{1-2}$—$C_{3-6}$cycloalkyl (optionally substituted with F), —$(CH_2)_{0-2}$-phenyl, —$(CH_2)_{1-2}$-heterocycle (optionally substituted with $C_{1-4}$ alkyl), $C_{1-6}$ alkyl (optionally substituted with F, OH, $C_{1-4}$ alkoxy (optionally substituted with F), $NHCO_2(C_{1-4}$alkyl), $SC_{1-4}$alkyl, $S(O)_2NH_2$, $OCH_2$-phenyl), $C_{2-4}$ alkenyl, and $C_{2-4}$ alkynyl.

In another non-limiting embodiment,

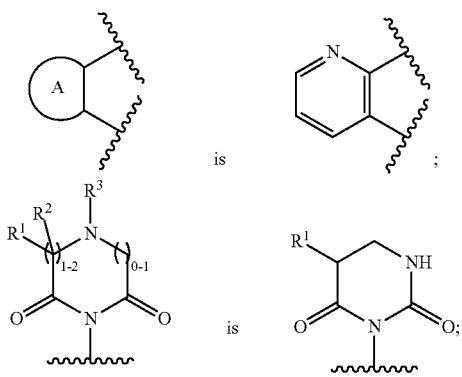
is
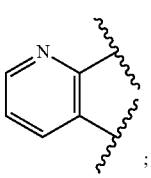
;
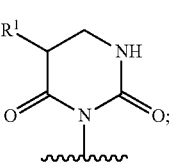
is $R^1$ is selected from —$(CH_2)_{1-2}$—$C_{3-6}$cycloalkyl (optionally substituted with F), —$(CH_2)_{0-2}$-phenyl, —$(CH_2)_{1-2}$-heterocycle (optionally substituted with $C_{1-4}$ alkyl), $C_{1-6}$ alkyl (optionally substituted with F, OH, $C_{1-4}$ alkoxy (optionally substituted with F), $NHCO_2(C_{1-4}$alkyl), $SC_{1-4}$alkyl, $S(O)_2NH_2$, $OCH_2$-phenyl), $C_{2-4}$ alkenyl, and $C_{2-4}$ alkynyl.

In another aspect, the present invention provides a compound selected from any subset list of compounds exemplified in the present application.

In another embodiment, the compounds of the present invention have ROCK $IC_{50}$ values ≤10 µM.

In another embodiment, the compounds of the present invention have ROCK $IC_{50}$ values ≤1 µM.

In another embodiment, the compounds of the present invention have ROCK $IC_{50}$ values ≤0.1 µM.

In another embodiment, the compounds of the present invention have ROCK $IC_{50}$ values ≤0.05 µM.

In another embodiment, the compounds of the present invention have ROCK $IC_{50}$ values ≤0.01 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "Co alkyl" or "Co alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, $C_1$, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., $N \rightarrow O$ and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs,* Elsevier (1985), and Widder, K. et al., eds., *Methods in Enzymology,* 112:309-396, Academic Press (1985);
b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988); and
e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, CA (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2H$" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | Methyl |
| Et | Ethyl |
| Pr | Propyl |
| i-Pr | Isopropyl |
| Bu | Butyl |
| i-Bu | Isobutyl |
| t-Bu | tert-butyl |
| Ph | Phenyl |
| Bn | Benzyl |
| Boc | tert-butyloxycarbonyl |
| AcOH or HOAc | acetic acid |
| BOP reagent | benzotriazol-1-yloxytris(dimethylamino)phosphonium hexafluorophosphate |
| CBz | carbobenzyloxy |
| $CH_2Cl_2$ | dichloromethane |

-continued

| | |
|---|---|
| CH₃CN or ACN | Acetonitrile |
| CDCl₃ | deutero-chloroform |
| CHCl₃ | Chloroform |
| DCM | dichloromethane |
| DEA | Diethylamine |
| DIC or DIPCDI | diisopropylcarbodiimide |
| DIEA, DIPEA or Hunig's base | diisopropylethylamine |
| DMAP | 4-dimethylaminopyridine |
| DME | 1,2-dimethoxyethane |
| DMF | dimethyl formamide |
| DMSO | dimethyl sulfoxide |
| cDNA | complimentary DNA |
| EDTA | ethylenediaminetetraacetic acid |
| Et₃N or TEA | triethylamine |
| EtOAc | ethyl acetate |
| Et₂O | diethyl ether |
| EtOH | Ethanol |
| HCl | hydrochloric acid |
| Hex | Hexane |
| K₂CO₃ | potassium carbonate |
| KOAc | potassium acetate |
| K₃PO₄ | potassium phosphate |
| LAH | lithium aluminum hydride |
| LG | leaving group |
| MeOH | Methanol |
| MgSO₄ | magnesium sulfate |
| MsOH or MSA | methylsulfonic acid |
| NaOAc | sodium acetate |
| NaCl | sodium chloride |
| NaH | sodium hydride |
| NaHCO₃ | sodium bicarbonate |
| Na₂CO₃ | sodium carbonate |
| Na₂SO₄ | sodium sulfate |
| NH₄Cl | ammonium chloride |
| OTf | triflate or trifluoromethanesulfonate |
| Pd/C | palladium on carbon |
| PG | protecting group |
| i-PrOH or IPA | Isopropanol |
| rt | Room temperature |
| RT or $t_R$ | retention time |
| SiO₂ | silica oxide |
| TEA | Trimethylamine |
| TFA | trifluoroacetic acid |
| THF | Tetrahydrofuran |
| T3P ® | propane phosphonic acid anhydride |

IV. Biology

In Vitro Assays

The effectiveness of compounds of the present invention as ROCK inhibitors can be determined in a 30 µL assay containing 20 mM HEPES, pH 7.5, 20 mM MgCl₂, 0.015% Brij-35, 4 mM DTT, 5 µM ATP and 1.5 µM peptide substrate (FITC-AHA-AKRRRLSSLRA-OH) (SEQ ID No. 1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC₅₀; i.e., the concentration of compound required to inhibit 50% of kinase activity.

Representative Examples were tested in the ROCK assay described above and found having ROCK inhibitory activity. A range of ROCK inhibitory activity (IC₅₀ values) of ≤50 µM (50000 nM) was observed. Table A below lists the ROCK IC₅₀ values measured for the following examples.

TABLE A

| Example No. | ROCK2 IC₅₀ (nM) |
|---|---|
| 1 | 8 |
| 2 | 8 |
| 3 | 9 |
| 4 | 13 |
| 5 | 25 |
| 6 | 91 |
| 7 | 129 |
| 8 | 190 |
| 9 | 219 |
| 10 | 224 |
| 11 | 225 |
| 12 | 270 |
| 13 | 515 |
| 14 | 562 |
| 15 | 744 |
| 16 | 902 |
| 17 | 1,340 |
| 18 | 1,498 |
| 19 | 1,633 |
| 20 | 1,713 |
| 21 | 2,378 |
| 22 | 2,953 |
| 23 | 2,023 |
| 24 | 197 |
| 25 | 10 |
| 26 | 38 |
| 27 | 45 |
| 28 | 57 |
| 29 | 62 |
| 30 | 89 |
| 31 | 123 |
| 32 | 156 |
| 33 | 426 |
| 34 | 539 |
| 35 | 1,664 |
| 36 | 2,388 |
| 37 | 44 |
| 38 | 5 |
| 39 | 14 |
| 40 | 14 |
| 41 | 19 |
| 42 | 22 |
| 43 | 23 |
| 44 | 29 |
| 45 | 30 |
| 46 | 48 |
| 47 | 50 |
| 48 | 56 |
| 49 | 99 |
| 50 | 62 |
| 51 | 155 |
| 52 | 160 |
| 53 | 171 |
| 54 | 186 |
| 55 | 212 |
| 56 | 256 |
| 57 | 259 |
| 58 | 289 |
| 59 | 303 |
| 60 | 311 |
| 61 | 378 |
| 62 | 421 |
| 63 | 617 |
| 64 | 802 |
| 65 | 968 |
| 66 | 1,547 |
| 67 | 1,781 |
| 68 | 17 |
| 69 | 16 |
| 70 | 20 |
| 71 | 36 |
| 72 | 885 |
| 73 | 2,275 |

TABLE A-continued

| Example No. | ROCK2 IC$_{50}$ (nM) |
| --- | --- |
| 74 | 75 |
| 75 | 138 |
| 76 | 456 |
| 77 | 614 |
| 78 | 963 |
| 79 | 131 |
| 80 | 2 |
| 81 | 3 |
| 82 | 5 |
| 83 | 9 |
| 84 | 17 |
| 85 | 6 |
| 86 | 6 |
| 87 | 5 |
| 88 | 55 |
| 89 | 13 |
| 90 | 21 |
| 91 | 29 |
| 92 | 6 |
| 93 | 9 |
| 94 | 27 |
| 95 | 6 |
| 96 | 264 |
| 97 | 28 |
| 98 | 52 |
| 99 | 659 |
| 100 | 52 |
| 101 | 146 |
| 102 | 5 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof, and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

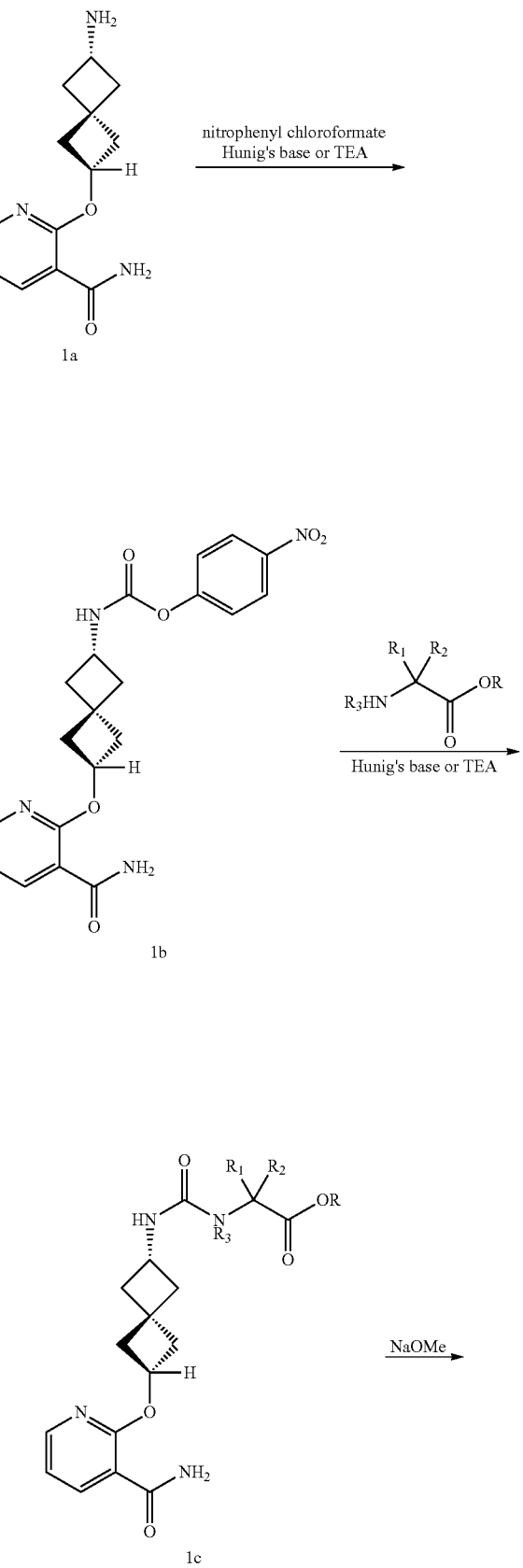

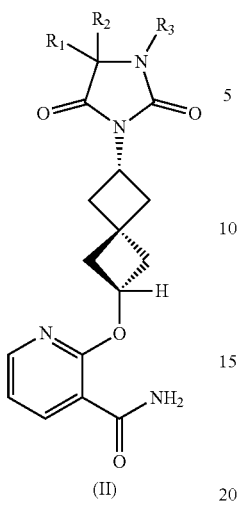

(II)

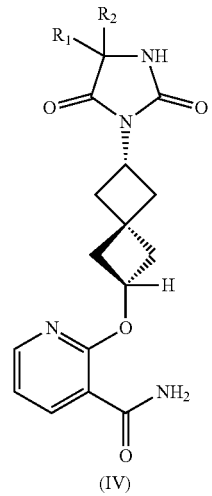

(IV)

Scheme 1 shows the synthesis of compound (II) from spiroheptane amine 1a. Treatment of amine 1a with an amine base such as TEA or Hünig's base and nitrophenyl chloroformate affords carbamate 1b. Carbamate 1b can then be treated with commercially available amino acid esters (R=Me, Et) where $R_3$=H, alkyl, aryl to afford urea 1c. Urea 1c can then be cyclized to hydantoin (II) by treatment with NaOMe.

Scheme 2

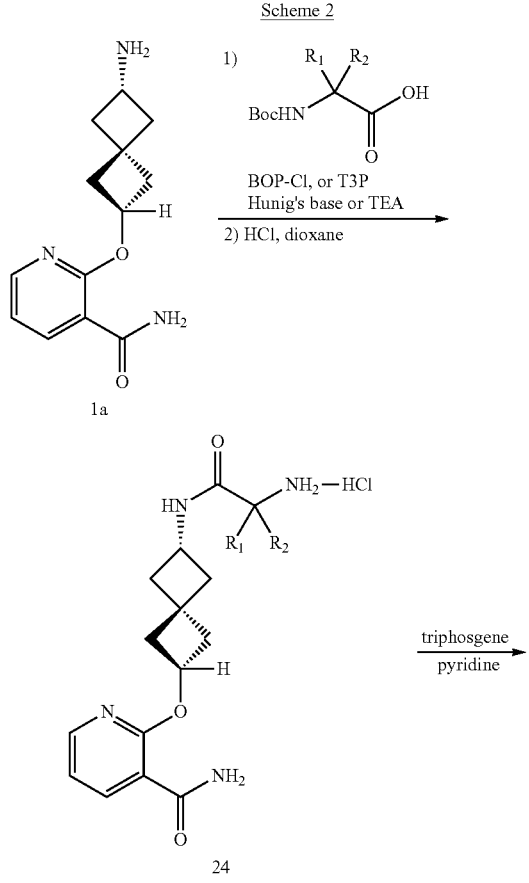

Scheme 2 shows an alternative method for the production of hydantoins (IV) from intermediate 1a. Treatment of amine 1a with a commercially available Boc-protected amino acid, an amine base such as TEA or Hunig's base, and a known amide forming reagent such as BOP-Cl or T3P®, followed by removal of the Boc group with HCl in dioxane leads to the formation of amine 24 as the HCl salt. Treatment of this salt with triphosgene in pyridine results in the formation of hydantoins of the formula (IV).

Scheme 3

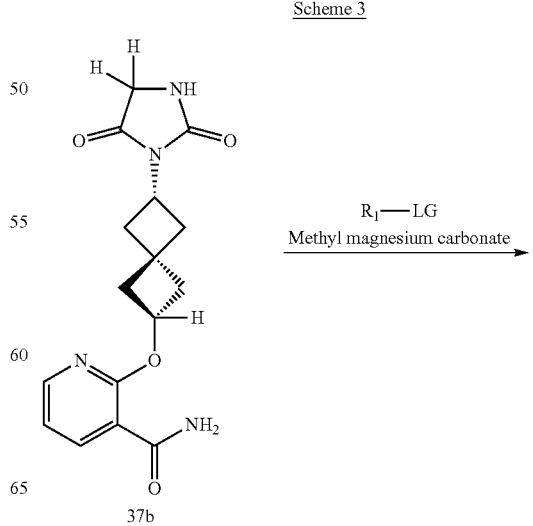

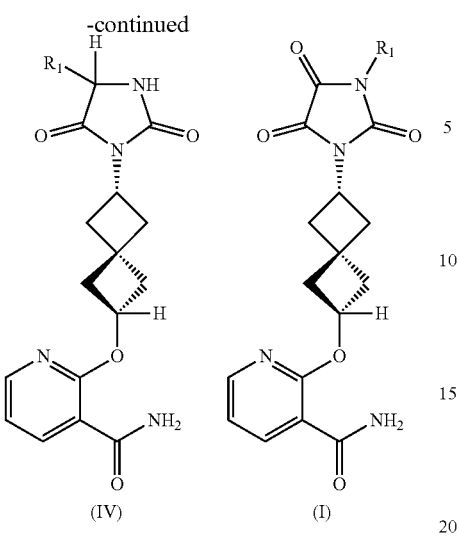
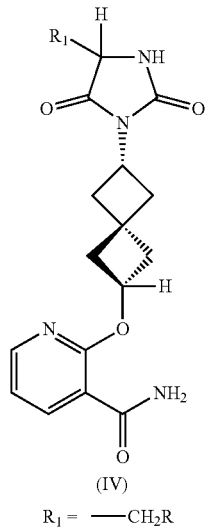

$R_1 = -CH_2R$

Scheme 4 shows how hydantoins of the formula IV can be produced from intermediate 37b. Hydantoin IV was treated with a suitable aldehyde RCHO in the presence of either KOAc or NaOAc and heated in DMF. The resulting aldol condensation product was then reduced with $NaBH_4$ in the presence of $CoCl_2$ to furnish hydantoin IV.

Scheme 3 shows how hydantoins of the formula IV (where $R_2$=H) were prepared. Intermediate 37b was prepared according to the procedure outlined in Scheme 1 using glycine methyl ester ($R_1$=$R_2$=$R_3$=H). Treatment of intermediate 37b with methyl magnesium carbonate and a suitable alkane bearing a leaving group, followed by workup with HCl furnished hydantoins IV. These reactions can also produce imidazole trione I when oxygen has not been rigorously excluded, and these adducts were prepared accordingly.

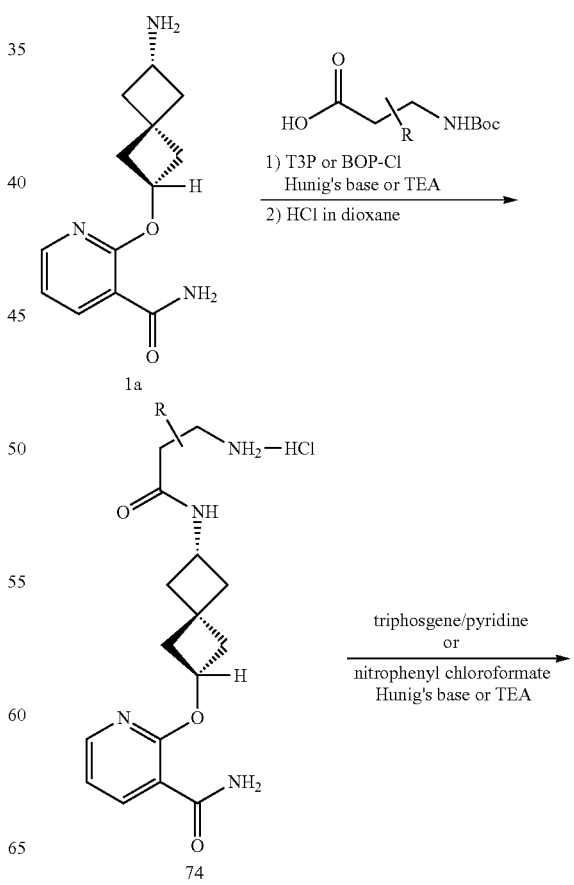

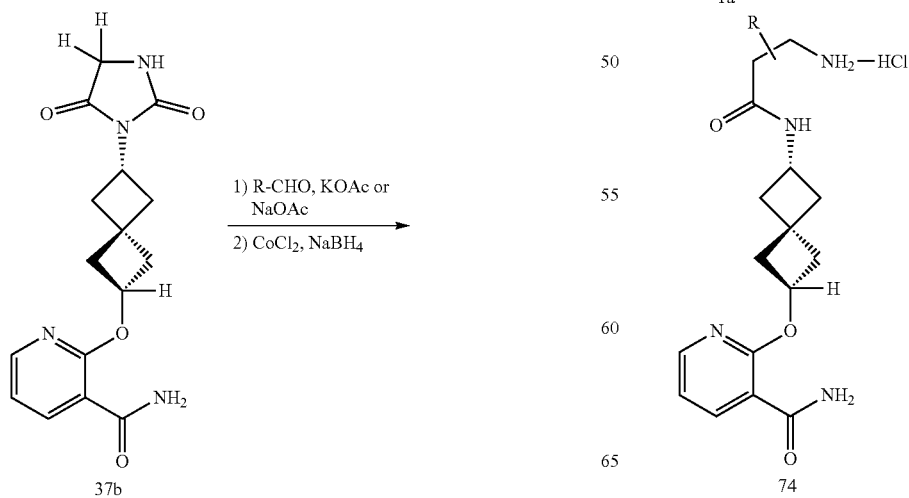

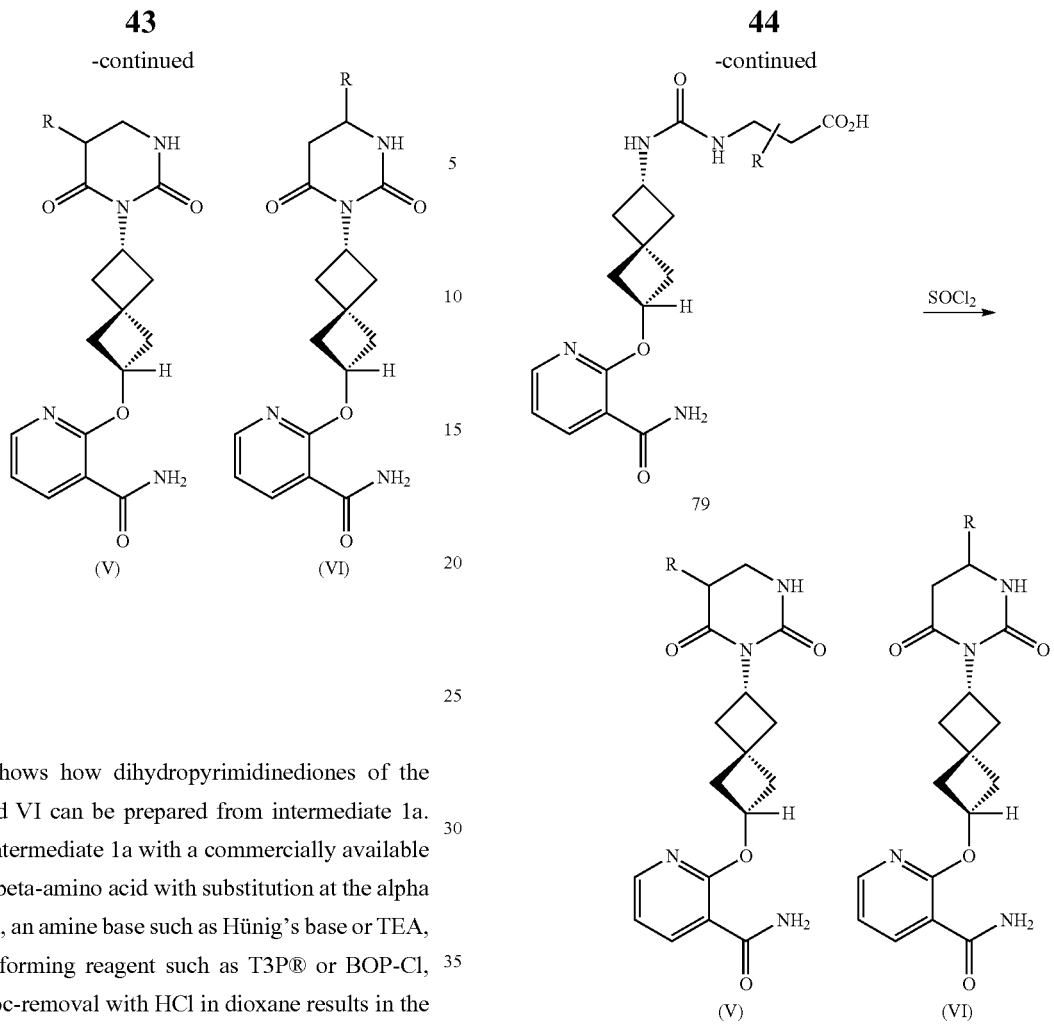

Scheme 5 shows how dihydropyrimidinediones of the formulas V and VI can be prepared from intermediate 1a. Treatment of intermediate 1a with a commercially available Boc-protected beta-amino acid with substitution at the alpha or beta position, an amine base such as Hünig's base or TEA, and an amide forming reagent such as T3P® or BOP-Cl, followed by Boc-removal with HCl in dioxane results in the formation of amine 74 as the HCl salt. Treatment of amine 74 with a carbonylating reagent such as triphosgene or nitrophenyl chloroformate in the presence of a suitable amine base results in the formation of dihydropyrimidinediones V or VI depending on whether alpha or beta substituted amino acids were employed as starting materials.

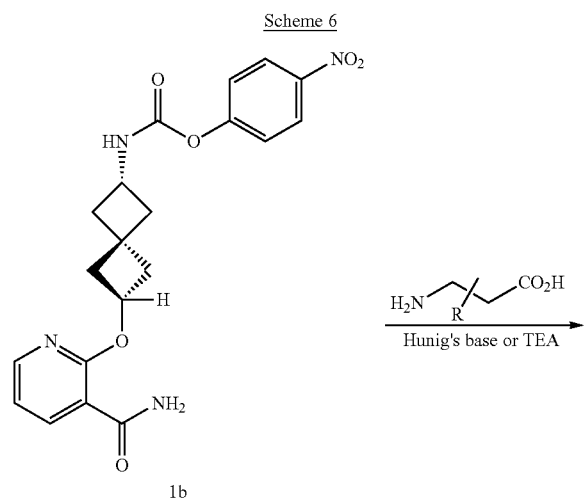

Scheme 6 shows an alternative method for the production of dihydropyrimidinediones V and VI from intermediate 1b. Carbamate 1b could be treated with beta-amino acids bearing a substituent in the alpha or beta position and an amine base such as TEA or Hunig's base. The resulting urea 79 could then be treated with thionyl chloride to furnish dihydropyrimidinediones (V) or (VI) respectively depending on whether alpha or beta substituted amino acids were employed.

Purification of intermediates and final products were carried out via either normal or reverse phase chromatography. Normal phase chromatography was carried out using pre-packed $SiO_2$ cartridges eluting with either gradients of hexanes and EtOAc, DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% $CH_3CN$, 0.1% TFA) and Solvent B (10% water, 90% $CH_3CN$, 0.1% TFA, UV 220 nm) or with gradients of Solvent A (98% water, 2% $CH_3CN$, 0.05% TFA) and Solvent B (98% $CH_3CN$, 2% water, 0.05% TFA, UV 220 nm) (or) Sunfire Prep C18 OBD 5 u 30×100 mm, 25 min gradient from 0-100% B. A=$H_2O$/$CH_3CN$/TFA 90:10:0.1. B=$CH_3CN$/$H_2O$/TFA 90:10:0.1

Unless otherwise stated, analysis of final products was carried out by reverse phase analytical HPLC.

Method A: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Method B: Waters Acquity UPLC BEH C18, 2.1×50 mm, 1.7-μm particles; Mobile Phase A: 5:95 acetonitrile: water with 0.1% TFA; Mobile Phase B: 95:5 acetonitrile: water with 0.1% TFA; Temperature: 50° C.; Gradient: 0-100% B over 3 minutes, then a 0.75-minute hold at 100% B; Flow: 1.11 mL/min.

Intermediate 1a. Preparation of 2-(((aR)-6-aminospiro[3.3]heptan-2-yl)oxy)nicotinamide

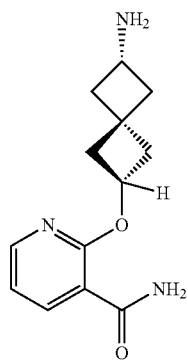

Intermediate 1-1. Preparation of Benzyl (6-oxospiro[3.3]heptan-2-yl)carbamate

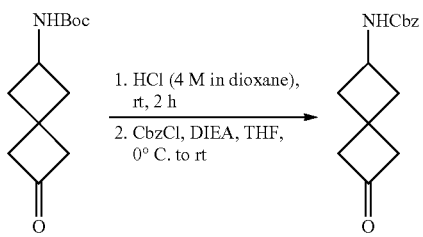 [SMILES: CC(C)(C)OC(=O)NC1CC2(CC(=O)C2)C1 ; O=C1CC2(C1)CC(NC(=O)OCc1ccccc1)C2]

Commercially available tert-butyl (6-oxospiro[3.3]heptan-2-yl)carbamate (0.150 g, 0.666 mmol) was dissolved in HCl (4 M in dioxane) (5.0 mL, 20 mmol). After stirring for 2 h, the reaction mixture was concentrated, and co-evaporated with Et$_2$O (4×10 mL), and further dried under high vacuum. The deprotected aminospiroketone, HCl salt was suspended in anhydrous THF (5 mL) and cooled to 0° C. Afterwards, Cbz-Cl (0.105 mL, 0.732 mmol) was added dropwise, followed by immediate addition of DIEA (0.291 mL, 1.66 mmol). The reaction mixture was stirred at 0° C. for 30 min, then ice bath was removed, and the reaction mixture was stirred at rt. After 1 h, the reaction mixture was quenched by the addition of MeOH (0.5 mL), concentrated under reduced pressure and the residue was purified normal phase chromatography to give benzyl (6-oxospiro[3.3]heptan-2-yl)carbamate (0.15 g, 89% yield) as a colorless syrup. MS (ESI) m/z: 260.1 (M+H)$^+$. $^1$H NMR (500 MHz, CDCl$_3$) δ ppm 7.36 (s, 5H), 5.10 (s, 2H), 4.95 (br s, 1H), 4.31-4.15 (m, 1H), 3.14 (br d, J=2.9 Hz, 2H), 3.09-3.04 (m, 2H), 2.71-2.50 (m, 2H), 2.27-2.13 (m, 2H).

Intermediate 1-2. Benzyl (6-hydroxyspiro[3.3]heptan-2-yl)carbamate

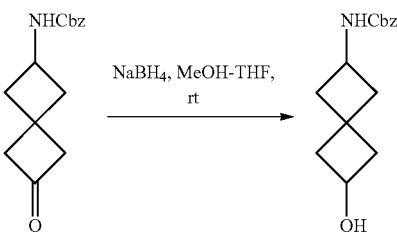 [SMILES: O=C1CC2(C1)CC(NC(=O)OCc1ccccc1)C2 ; O=C(NC1CC2(CC(O)C2)C1)OCc1ccccc1]

Benzyl (6-oxospiro[3.3]heptan-2-yl)carbamate (0.153 g, 0.590 mmol) was dissolved in anhydrous THF (3 mL)/MeOH (3 mL) and cooled to 0° C. NaBH$_4$ (0.033 g, 0.89 mmol) was added in one portion and stirred at 0° C. for 30 min before allowing the reaction mixture to come to rt. After an additional 30 min, the reaction was quenched by the addition of saturated NH$_4$Cl (1 mL). The organics were removed by concentrating under reduced pressure. The resulting residue was dissolved in EtOAc (50 mL) and treated with saturated NH$_4$Cl (25 mL). After 5 min, the organic phase was separated, washed with brine (25 mL), dried over Na$_2$SO$_4$, filtered, and concentrated under reduced pressure to afford benzyl (6-hydroxyspiro[3.3]heptan-2-yl)carbamate (0.154 g, 0.589 mmol, 100% yield) as a white solid. The material was used without further purification in the next step. MS (ESI) m/z: 262.1 (M+H)$^+$. $^1$H NMR (500 MHz, CDCl$_3$) δ ppm 7.27 (s, 5H), 5.10-4.95 (m, 2H), 4.08-3.95 (m, 1H), 3.74 (br s, 3H), 2.47-2.13 (m, 4H), 1.94-1.70 (m, 4H).

Example 1-3. Preparation of benzyl (6-((3-cyanopyridin-2-yl)oxy)spiro[3.3]heptan-2-yl)carbamate

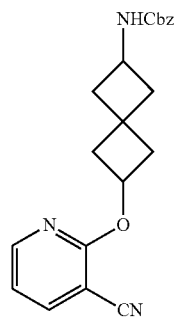 [SMILES: N#Cc1cccnc1OC1CC2(CC(NC(=O)OCc3ccccc3)C2)C1]

To a solution of Intermediate 1-2 (0.48 g, 1.8 mmol) in anhydrous THF (14 mL) at 0° C., was added 60% NaH (0.162 g, 4.04 mmol). The reaction mixture was stirred at rt until becoming mostly homogeneous (~30 min), then, 2-chloronicotinonitrile (0.5 g, 4 mmol) was added in one portion, and the reaction mixture was allowed to stir for 16 h. The reaction mixture was quenched by the addition of sat. NH$_4$Cl and evaporated. The residue was partitioned between water (20 mL) and ethyl acetate (50 mL). The aqueous layer was extracted with ethyl acetate (2×20 mL). The combined organic layers were washed with sat. NaHCO$_3$ and brine, dried (MgSO$_4$) and concentrated under reduced pressure. The residue was purified via flash chromatography to afford benzyl (6-((3-cyanopyridin-2-yl)oxy)spiro[3.3]heptan-2-yl)

carbamate (0.52 g, 78% yield), as a clear oil. MS (ESI) m/z: 364.1 (M+H)+; $^1$H NMR (400 MHz, CDCl$_3$) δ 8.31 (dd, J=5.1, 2.0 Hz, 1H), 7.86 (dd, J=7.5, 2.0 Hz, 1H), 7.42-7.29 (m, 5H), 6.95 (dd, J=7.6, 5.0 Hz, 1H), 5.23 (quin, J=7.2 Hz, 1H), 5.09 (s, 2H), 4.83 (br. s., 1H), 2.74-2.61 (m, 1H), 2.59-2.38 (m, 3H), 2.27 (dt, J=11.8, 7.3 Hz, 2H), 2.02-1.91 (m, 2H).

Intermediate 1-4. Preparation of benzyl ((aR)-6-((3-carbamoylpyridin-2-yl)oxy)spiro[3.3]heptan-2-yl)carbamate

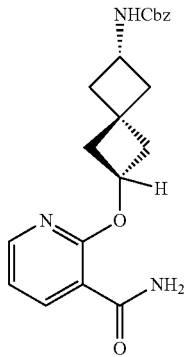

To a solution of Intermediate 1-3 (0.52 g, 1.4 mmol) in DMSO (12 mL), were added K$_2$CO$_3$ (0.593 g, 4.29 mmol) and magnesium oxide (0.288 g, 7.15 mmol). To the reaction mixture was added 30% aq. hydrogen peroxide (1.61 mL, 15.7 mmol) dropwise over 5 min (slight exotherm), and the reaction mixture was stirred at rt. The reaction mixture was diluted with EtOAc (80 mL) and dilute HCl (25 mL). Organic phase was separated, washed with sat. NaHCO$_3$ (2×25 mL) and brine (1×25 mL), dried (MgSO$_4$) and filtered. Solvent was removed under reduced pressure. The racemic product was subjected to chiral prep HPLC (Instrument: Berger MGII Prep SFC (Column: Chiralpak IC, 21×250 mm, 5 micron; Mobile Phase: 35% MeOH/65% CO$_2$; Flow Conditions: 45 mL/min, 110 Bar, 40° C.; Detector Wavelength: 220 nm; Injection Details: 0.5 mL of 12 mg/mL in Methanol) and the second peak was collected to afford Intermediate 1-4 (229 mg, 42.0% yield). MS (ESI) m/z: 382.1 (M+H)+.

Intermediate 1a. Preparation of 2-(((aR)-6-amino-spiro[3.3]heptan-2-yl)oxy)nicotinamide

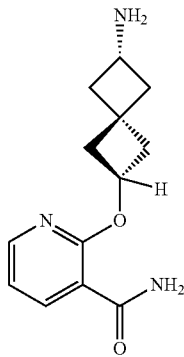

Intermediate 1-4 (229 mg, 0.601 mmol) in MeOH/EtOH and 90 mg (50% water) Pd/C was hydrogenated at 50 psi. The mixture was filtered and concentrated under reduced pressure to afford Intermediate 1a (146 mg, 98.0% yield) which was used without further purification. MS (ESI) m/z: 248.1 (M+H)+.

Example 1. Preparation of 2-(((aR)-6-(4-isobutyl-2,5-dioxoimidazolidin-1-yl)spiro[3.3]heptan-2-yl)oxy)nicotinamide

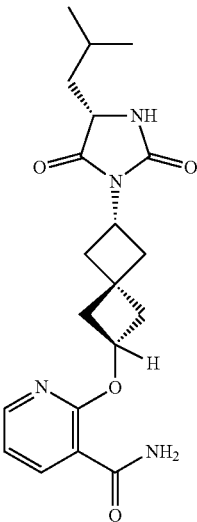

Intermediate 1b. Preparation of 4-nitrophenyl ((aR)-6-((3-carbamoylpyridin-2-yl)oxy)spiro[3.3]heptan-2-yl)carbamate

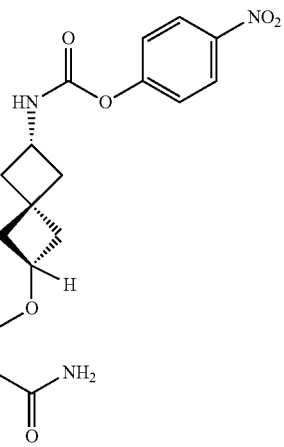

2-((((R)-6-aminospiro[3.3]heptan-2-yl)oxy)nicotinamide (2.0 g, 8.1 mmol) was suspended in anhydrous THF (210 mL), and DIEA (2.1 mL, 12 mmol) was added. The reaction mixture was cooled to 0° C., and 4-nitrophenyl chloroformate (2.0 g, 9.7 mmol) was added in one portion. The reaction mixture was allowed to warm to room temperature over 30 min. The reaction mixture was filtered through a membrane filter, and intermediate 1b was used without further purification in the subsequent urea formation step. MS (ESI) m/z 413.1 (M+H)

Intermediate 1c. Preparation of methyl ((((R)-6-((3-carbamoylpyridin-2-yl)oxy)spiro[3.3]heptan-2-yl)carbamoyl)-L-leucinate

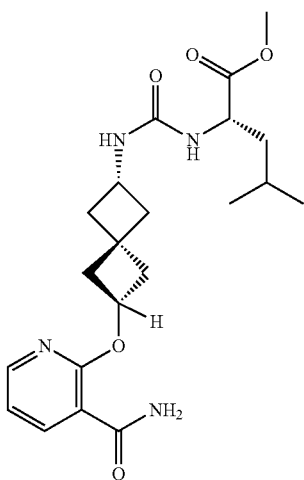

A mixture of methyl L-leucinate hydrogen chloride salt (1.5 g, 8.1 mmol) and DIEA (5.7 mL, 32 mmol) was dissolved in anhydrous THF (50 mL) and a solution of 4-nitrophenyl (((R)-6-((3-carbamoylpyridin-2-yl)oxy)spiro[3.3]heptan-2-yl)carbamate (210 mL, 8.1 mmol) was added. The reaction mixture was stirred at rt for 5 min, and then heated to 50° C. for 14 h. The cooled reaction solution was partitioned between EtOAc and 1M pH 7 phosphate buffer and the organic layer was concentrated under reduced pressure to furnish methyl ((((R)-6-((3-carbamoylpyridin-2-yl)oxy)spiro[3.3]heptan-2-yl)carbamoyl)-L-leucinate (3.4 g, 8.1 mmol, 100% yield) which was used without further purification. MS (ESI) m/z 419.1 (M+H).

Example 1. Preparation of 2-((((R)-6-((S)-4-isobutyl-2,5-dioxoimidazolidin-1-yl)spiro[3.3]heptan-2-yl)oxy)nicotinamide To a solution of methyl ((((R)-6-((3-carbamoylpyridin-2-yl)oxy)spiro[3.3]heptan-2-yl)carbamoyl)-L-leucinate (5.1 g, 12 mmol) dissolved in MeOH (40 mL) was added sodium methoxide (3.0 mL, 13 mmol) and the reaction mixture heated to 50° C. for 2 h. The reaction was concentrated under reduced pressure, the residue triturated with 1M NaOH, filtered, washed with water and dried under vacuum to furnish 2-((((R)-6-(4-isobutyl-2,5-dioxoimidazolidin-1-yl)spiro[3.3]heptan-2-yl)oxy)nicotinamide (3.7 g, 9.5 mmol, 79% yield) as a mixture of diastereomers. $^1$H NMR (500 MHz, chloroform-d) δ 8.52 (dd, J=7.6, 2.1 Hz, 1H), 8.28 (dd, J=4.8, 2.1 Hz, 1H), 7.80 (br s, 1H), 7.06 (dd, J=7.6, 4.8 Hz, 1H), 5.81 (br s, 1H), 5.42-5.28 (m, 2H), 4.53 (quin, J=8.8 Hz, 1H), 4.03-3.93 (m, 1H), 3.09-2.96 (m, 2H), 2.84-2.76 (m, 1H), 2.71 (dt, J=12.1, 6.1 Hz, 1H), 2.48-2.36 (m, 1H), 2.34-2.20 (m, 3H), 1.85-1.74 (m, 2H), 1.53 (dd, J=9.5, 8.1 Hz, 1H), 1.00 (dd, J=7.3, 6.5 Hz, 6H). MS (ESI) m/z 387.1 (M+H).

Diastereomers of 2-((((R)-6-(4-isobutyl-2,5-dioxoimidazolidin-1-yl)spiro[3.3]heptan-2-yl)oxy)nicotinamide were separated via preparative SFC with the following conditions: Column: Chiralpak IA, 4.6×250 mm, 5-µm particles; Mobile Phase 35% MeOH/65% $CO_2$; Flow: 2.0 mL/min, 150 Bar, 40° C. Fractions containing the individual isomers were dried via centrifugal evaporation to furnish peak 1: 2-((((R)-6-((S)-4-isobutyl-2,5-dioxoimidazolidin-1-yl)spiro[3.3]heptan-2-yl)oxy)nicotinamide, Example 1 (1.3 g, 3.4 mmol, 28% yield). $^1$H NMR (500 MHz, chloroform-d) δ 8.52 (dd, J=7.6, 2.1 Hz, 1H), 8.28 (dd, J=4.8, 2.1 Hz, 1H), 7.81 (br s, 1H), 7.06 (dd, J=7.6, 4.8 Hz, 1H), 5.98 (br s, 1H), 5.74 (s, 1H), 5.35 (quin, J=7.2 Hz, 1H), 4.60-4.45 (m, 1H), 4.05-3.90 (m, 1H), 3.02 (q, J=10.4 Hz, 2H), 2.80 (dt, J=11.6, 5.9 Hz, 1H), 2.71 (dt, J=12.0, 5.9 Hz, 1H), 2.46-2.36 (m, 1H), 2.34-2.20 (m, 3H), 1.86-1.76 (m, 2H), 1.59-1.47 (m, 1H), 1.00 (t, J=6.3 Hz, 6H). MS (ESI) m/z 387.1 (M+H).

Examples 2-23 were prepared using the general methods described above for Example 1 using the corresponding commercially available amino acid esters. Compounds were prepared as an epimeric mixture of diastereomers at the hydantoin methine stereocenter. Chiral separation conditions and retention times for examples that were separated into single diastereomers are included in Table 1. Unless otherwise noted, compounds were evaluated as a mixture of diastereomers.

Example 24. Preparation of 2-((((R)-6-((S)-4-benzyl-2,5-dioxoimidazolidin-1-yl)spiro[3.3]heptan-2-yl)oxy)nicotinamide

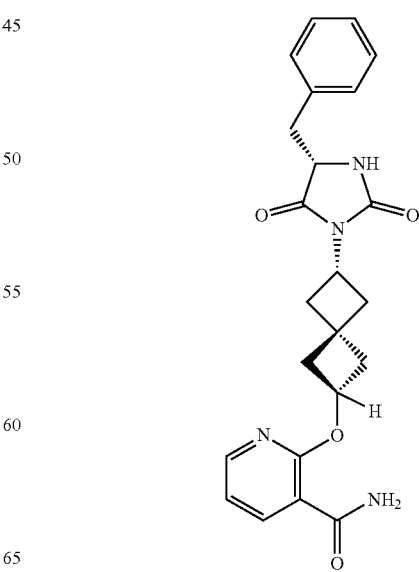

Intermediate 24a. Preparation of tert-butyl ((S)-1-((((R)-6-((3-carbamoylpyridin-2-yl)oxy)spiro[3.3]heptan-2-yl)amino)-1-oxo-3-phenylpropan-2-yl)carbamate

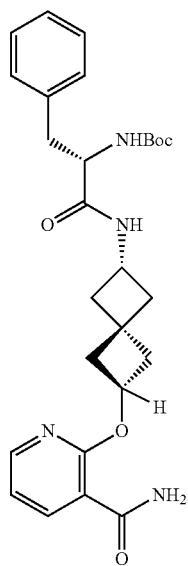

To a mixture of 2-((((R)-6-aminospiro[3.3]heptan-2-yl)oxy)nicotinamide (0.017 g, 0.069 mmol), (S)-2-((tert-butoxycarbonyl)amino)-3-phenylpropanoic acid (0.018 g, 0.069 mmol), and Et$_3$N (0.057 mL, 0.41 mmol) slurried in THF (0.7 mL) was added T3P® (0.12 mL, 0.21 mmol) and stirred for 16 h. The reaction mixture was partitioned between EtOAc and 1M dibasic phosphate buffer, and the organic phase was concentrated under reduced pressure to furnish tert-butyl ((S)-1-((((R)-6-((3-carbamoylpyridin-2-yl)oxy)spiro[3.3]heptan-2-yl)amino)-1-oxo-3-phenylpropan-2-yl)carbamate (0.034 g, 0.069 mmol, 100% yield) which was used without further purification. MS (ESI) m z 395.2 (M+H-Boc)

Intermediate 24b. Preparation of 2-((((R)-6-((S)-2-amino-3-phenylpropanamido)spiro[3.3]heptan-2-yl)oxy)nicotinamide hydrochloride Salt

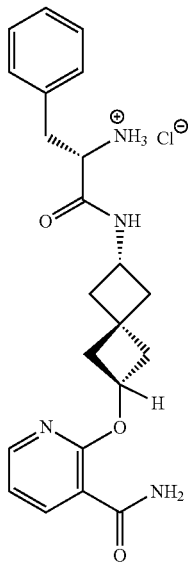

To tert-butyl ((S)-1-((((R)-6-((3-carbamoylpyridin-2-yl)oxy)spiro[3.3]heptan-2-yl)amino)-1-oxo-3-phenylpropan-2-yl)carbamate (0.033 g, 0.067 mmol) was added a solution of HCl (0.34 mL, 1.3 mmol) in dioxane and stirred for 16 h. The reaction mixture was partitioned between EtOAc/1M phosphate buffer, concentrated to furnish 2-((((R)-6-((S)-2-amino-3-phenylpropanamido)spiro[3.3]heptan-2-yl)oxy)nicotinamide hydrochloride salt (0.030 g, 0.067 mmol, 100% yield) which was used without further purification. MS (ESI) m/z 395.2 (M+H).

Example 24. Preparation of 2-((((R)-6-((S)-4-benzyl-2,5-dioxoimidazolidin-1-yl)spiro[3.3]heptan-2-yl)oxy)nicotinamide To a solution of pyridine (0.092 mL, 1.1 mmol) and 2-((((R)-6-((S)-2-amino-3-phenylpropanamido)spiro[3.3]heptan-2-yl)oxy)nicotinamide hydrochloride (0.030 g, 0.069 mmol) dissolved in DCM (0.7 mL) and cooled to 0° C. was added a solution of triphosgene (0.008 g, 0.03 mmol) dissolved in DCM (0.5 mL). The reaction mixture was allowed to warm to room temperature for 30 min and then heated to 50° C. for 2 h. The reaction mixture was concentrated under reduced pressure and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 12-52% B over 25 minutes, then a 5-minute hold at 100% B; Flow: 20 mL/min. Fractions containing Example 24 were combined and dried via centrifugal evaporation to furnish 2-((((R)-6-((S)-4-benzyl-2,5-dioxoimidazolidin-1-yl)spiro[3.3]heptan-2-yl)oxy)nicotinamide (1.8 mg, 4.3 μmol, 6.2% yield): $^1$H NMR (500 MHz, DMSO-d$_6$) δ 8.30-8.22 (m, 1H), 8.20-8.11 (m, 2H), 7.71-7.54 (m, 2H), 7.31-7.18 (m, 3H), 7.14 (br d, J=7.0 Hz, 2H), 7.10 (dd, J=7.3, 4.9 Hz, 1H), 5.16 (quin, J=7.2 Hz, 1H), 4.27 (br t, J=4.3 Hz, 1H), 4.10 (quin, J=8.9 Hz, 1H), 2.94 (br d, J=4.3 Hz, 2H), 2.58 (br d, J=10.1 Hz, 3H), 2.47-2.37 (m, 1H), 2.24-2.12 (m, 2H), 2.11-1.95 (m, 2H). MS (ESI) m z 421.1 (M+H).

Examples 25-36 were prepared by the general procedures described for Example 24. Each isomer was prepared as a single stereoisomer as drawn.

Example 37. Preparation of 2-((((R)-6-(4-(2-cyclopropylethyl)-2,5-dioxoimidazolidin-1-yl)spiro[3.3]heptan-2-yl)oxy)nicotinamide

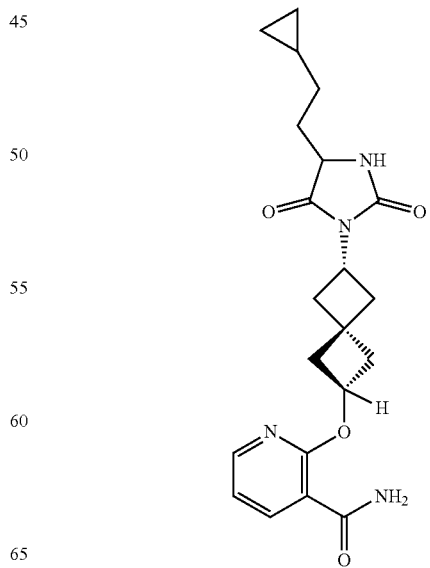

Intermediate 37a. Preparation of methyl (((R)-6-((3-carbamoylpyridin-2-yl)oxy)spiro[3.3]heptan-2-yl)carbamoyl)glycinate

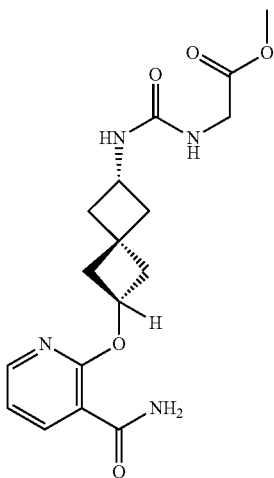

To a mixture of methyl glycinate hydrochloride salt (2.0 g, 16 mmol) and DIEA (11 mL, 65 mmol) dissolved in anhydrous THF (80 mL) was added 4-nitrophenyl ((R)-6-((3-carbamoylpyridin-2-yl)oxy)spiro[3.3]heptan-2-yl)carbamate (430 mL, 16 mmol). The reaction mixture was stirred at rt for 5 min, and then at 50° C. for 16 h. The reaction mixture was partitioned between EtOAc and 1M phosphate buffer, and the organic layer was concentrated under reduced pressure to furnish methyl (((R)-6-((3-carbamoylpyridin-2-yl)oxy)spiro[3.3]heptan-2-yl)carbamoyl)glycinate (5.9 g, 16 mmol, 100% yield) which was used without further purification. MS (ESI) m/z 363.1 (M+H).

Intermediate 37b. Preparation of 2-(((( R)-6-(2,5-dioxoimidazolidin-1-yl)spiro[3.3]heptan-2-yl)oxy)nicotinamide

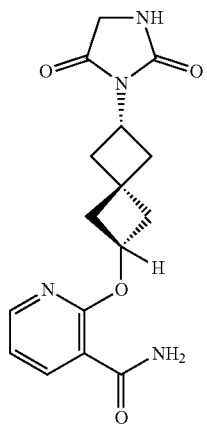

To a solution of methyl (((R)-6-((3-carbamoylpyridin-2-yl)oxy)spiro[3.3]heptan-2-yl)carbamoyl)glycinate (5.9 g, 16 mmol) dissolved in MeOH (54 mL) was added sodium methoxide (4.1 mL, 18 mmol) and heated to 50° C. 2 h. The resultant thick suspension was filtered, and solids were washed with water to furnish off-white solid 2-(((( R)-6-(2,5-dioxoimidazolidin-1-yl)spiro[3.3]heptan-2-yl)oxy)nicotinamide (3.7 g, 11 mmol, 69% yield): $^1$H NMR (500 MHz, methaol-$d_4$) δ 8.38 (dd, J=7.6, 2.1 Hz, 1H), 8.27 (dd, J=5.0, 1.9 Hz, 1H), 7.08 (dd, J=7.7, 5.0 Hz, 1H), 5.33 (quin, J=7.2 Hz, 1H), 4.56-4.42 (m, 1H), 3.87 (s, 2H), 3.01 (t, J=10.2 Hz, 2H), 2.79 (dt, J=11.6, 6.1 Hz, 1H), 2.72-2.63 (m, 1H), 2.45-2.36 (m, 1H), 2.34-2.24 (m, 3H). MS (ESI) m/z 331.1 (M+H).

Example 37. Preparation of 2-(((( R)-6-(4-(2-cyclopropylethyl)-2,5-dioxoimidazolidin-1-yl)spiro[3.3]heptan-2-yl)oxy)nicotinamide

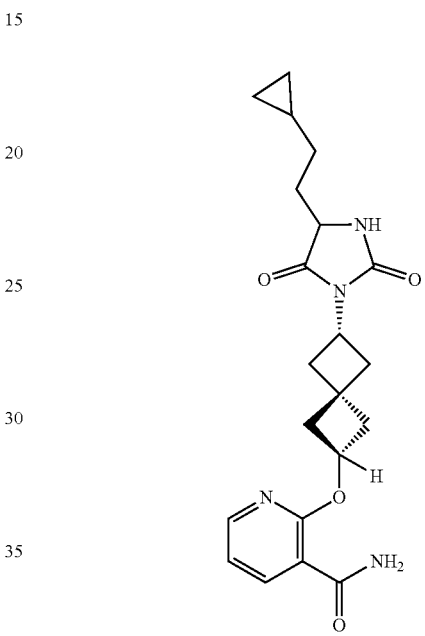

To a septum covered sealable vessel under nitrogen atmosphere containing mixture of 2-(((( R)-6-(2,5-dioxoimidazolidin-1-yl)spiro[3.3]heptan-2-yl)oxy)nicotinamide (33 mg, 0.10 mmol) and sodium iodide (15 mg, 0.10 mmol) was added magnesium methyl carbonate in DMF (0.1 mL, 0.2 mmol) and heated to 80° C. for 90 min. To the reaction mixture was added a solution of (2-bromoethyl)cyclopropane (15 mg, 0.10 mmol) dissolved in 0.1 mL of DMF and further heated 16 h. The reaction mixture was cooled in an ice bath and 0.05 mL conc. HCl was added. The residue was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 17-57% B over 20 minutes, then a 4-minute hold at 100% B; Flow: 20 mL/min. Fractions containing Example 37 were combined and dried via centrifugal evaporation to furnish a mixture of diastereomers 2-(((( R)-6-(4-(2-cyclopropylethyl)-2,5-dioxoimidazolidin-1-yl)spiro[3.3]heptan-2-yl)oxy)nicotinamide (0.015 g, 0.038 mmol, 38.0% yield). $^1$H NMR (500 MHz, DMSO-$d_6$) δ 8.28 (dd, J=4.9, 1.8 Hz, 1H), 8.23 (s, 1H), 8.17 (dd, J=7.3, 1.8 Hz, 1H), 7.77-7.52 (m, 2H), 7.12 (dd, J=7.3, 4.9 Hz, 1H), 5.23 (quin, J=7.2 Hz, 1H), 4.33 (quin, J=8.9 Hz, 1H), 4.06-3.96 (m, 1H), 2.92-2.77 (m, 2H), 2.68 (dt, J=11.9, 5.6 Hz, 1H), 2.51-2.45 (m, 1H), 2.37-2.13 (m, 4H), 1.86-1.72 (m, 1H), 1.59 (dq, J=14.3, 7.3 Hz, 1H), 1.27-1.15 (m, 2H), 0.71-0.58 (m, 1H), 0.40 (br d, J=8.2 Hz, 2H), 0.10-0.07 (m, 2H). MS (ESI) m/z 399.4 (M+H). Examples 38-67 were prepared using the general methods described for Example 37 using the corresponding commercially available alkyl halides. Compounds were prepared as an epimeric mixture of diastereomers at the hydantoin methine stereocenter. Separation conditions for select compounds employed the same method as for Example 1. Chiral separation conditions and retention times for examples that were separated into single diastereomers are included in Table 1. Unless otherwise noted, compounds were evaluated as a mixture of diastereomers.

Example 68. Preparation of 2-((((R)-6-(4-((1-adamantyl)methyl)-2,5-dioxoimidazolidin-1-yl)spiro[3.3]heptan-2-yl)oxy)nicotinamide

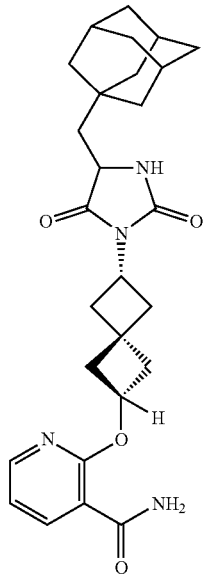

Intermediate 68a. Preparation of 2-((((R)-6-((Z)-4-((adamantan-1-yl)methylene)-2,5-dioxoimidazolidin-1-yl)spiro[3.3]heptan-2-yl)oxy)nicotinamide

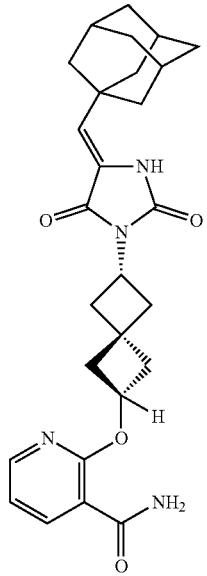

A solution of 2-((((R)-6-(2,5-dioxoimidazolidin-1-yl)spiro[3.3]heptan-2-yl)oxy)nicotinamide (33 mg, 0.10 mmol), adamantane-1-carbaldehyde (16 mg, 0.10 mmol) and sodium acetate (16 mg, 0.20 mmol) in DMF (0.4 mL) was heated in a sealed vessel to 160° C. overnight. The reaction mixture was then allowed to cool to rt and concentrated. The residue, 2-((((R)-6-((Z)-4-((adamantan-1-yl)methylene)-2,5-dioxoimidazolidin-1-yl)spiro[3.3]heptan-2-yl)oxy)nicotinamide (47.6 mg, 0.100 mmol, 100% yield) was used without further purification.

Example 68. Preparation of 2-((((R)-6-(4-((1-adamantyl)methyl)-2,5-dioxoimidazolidin-1-yl)spiro[3.3]heptan-2-yl)oxy)nicotinamide A solution of 2-((((R)-6-((Z)-4-(bicyclo[2.2.2]octan-1-ylmethylene)-2,5-dioxoimidazolidin-1-yl)spiro[3.3]heptan-2-yl)oxy)nicotinamide (45 mg, 0.10 mmol) in EtOH (2.0 mL) was treated with cobalt(II) chloride hexahydrate (24 mg, 0.10 mmol) and sodium borohydride (7.6 mg, 0.20 mmol) and allowed to stir for 14 h. The reaction mixture was then concentrated under reduced pressure and the residue partitioned between brine and EtOAc. The organic layer was concentrated under reduced pressure and the residue purified by preparative HPLC to furnish 2-((((R)-6-(4-(bicyclo[2.2.2]octan-1-ylmethyl)-2,5-dioxoimidazolidin-1-yl)spiro[3.3]heptan-2-yl)oxy)nicotinamide (2.5 mg, 5.3 μmol, 5.3% yield) as a ~1:1 mixture of diastereomers. MS (ESI) m/z: 453.0 (M+H)+. $^1$H NMR (500 MHz, DMSO-d6) δ 8.30-8.23 (m, 1H), 8.16 (br d, J=7.3 Hz, 1H), 8.08 (s, 1H), 7.71-7.58 (m, 2H), 7.11 (dd, J=7.3, 4.9 Hz, 1H), 5.21 (br t, J=7.0 Hz, 1H), 4.32 (quin, J=8.5 Hz, 1H), 3.96 (br d, J=9.2 Hz, 1H), 2.82 (q, J=9.3 Hz, 2H), 2.70-2.60 (m, 1H), 2.34-2.12 (m, 4H), 1.56 (br s, 1H), 1.54-1.43 (m, 7H), 1.34 (br d, J=6.1 Hz, 6H), 1.23 (s, 2H). Analytical HPLC RT=1.698 min (Method A) and 1.529 min (Method B), purity=100%.

Examples 69-73 were prepared as a roughly 1:1 mixture of diastereomers from commercially available aldehydes analogously to the procedure outlined above for Example 68.

Example 74. Preparation of 2-((((R)-6-((S)-2,6-dioxo-4-phenethyltetrahydropyrimidin-1(2H)-yl)spiro[3.3]heptan-2-yl)oxy)nicotinamide

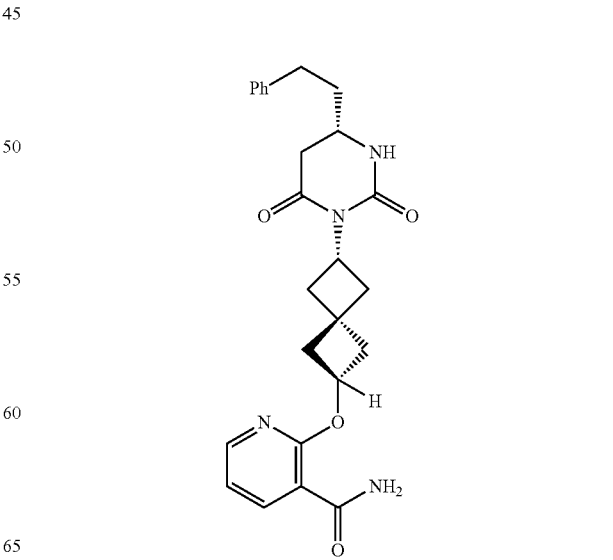

Intermediate 74a. 2-((((R)-6-((S)-3-amino-5-phenylpentanamido)spiro[3.3]heptan-2-yl)oxy)nicotinamide

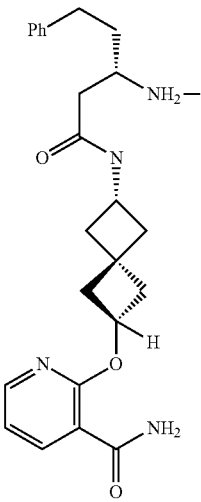

Intermediate 74a was prepared in two steps from the corresponding commercially available Boc-protected β-amino acid employing the same methods used to prepare Intermediate 24b.

Example 74: 2-((((R)-6-((S)-2,6-dioxo-4-phenethyltetrahydropyrimidin-1(2H)-yl)spiro[3.3]heptan-2-yl)oxy)nicotinamide A solution of 2-((((R)-6-((S)-3-amino-5-phenylpentanamido)spiro[3.3]heptan-2-yl)oxy)nicotinamide (42.3 mg, 0.100 mmol) in DCM (1.0 mL) was treated with Hunig's Base (0.09, 0.5 mmol) and 4-nitrophenyl chloroformate (24.2 mg, 0.120 mmol) and stirred for 14 h. The reaction mixture was concentrated under reduced pressure. The residue was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 21-61% B over 20 minutes, then a 4-minute hold at 100% B; Flow: 20 mL/min. Fractions containing Example 74 were combined and dried via centrifugal evaporation to furnish 2-((((R)-6-((S)-2,6-dioxo-4-phenethyltetrahydropyrimidin-1(2H)-yl)spiro[3.3]heptan-2-yl)oxy)nicotinamide (7.0 mg, 0.014 mmol, 14% yield). MS (ESI) m/z: 449.4 (M+H)+. 1H NMR (500 MHz, DMSO-d6) δ 8.33-8.13 (m, 2H), 7.74 (br s, 1H), 7.53 (br s, 2H), 7.34-7.01 (m, 6H), 5.31-5.19 (m, 1H), 4.69 (quin, J=8.7 Hz, 1H), 3.41 (br s, 1H), 3.29 (br d, J=6.0 Hz, 2H), 2.77-2.60 (m, 5H), 2.45 (br dd, J=16.4, 9.1 Hz, 1H), 2.38-2.29 (m, 1H), 2.28-2.13 (m, 3H), 1.86-1.60 (m, 2H). Analytical HPLC RT=1.64 min (Method A), purity=90%.

Examples 75-78 were prepared from commercially available aldehydes using the general procedure outlined for Example 68. Compounds were prepared as a single stereoisomer where all stereocenters are explicitly shown. All other compounds were prepared and evaluated as a 1:1 mixture of diastereomers.

Example 79. Preparation of 2-((((R)-6-(5-isobutyl-2,6-dioxotetrahydropyrimidin-1(2H)-yl)spiro[3.3]heptan-2-yl)oxy)nicotinamide

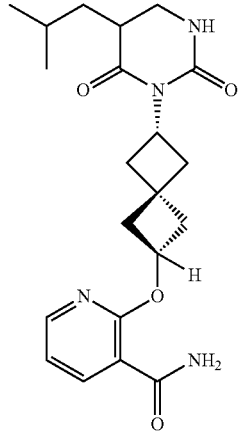

Intermediate 79a: 2-((3-(((R)-6-((3-carbamoylpyridin-2-yl)oxy)spiro[3.3]heptan-2-yl)ureido)methyl)-4-methylpentanoic acid

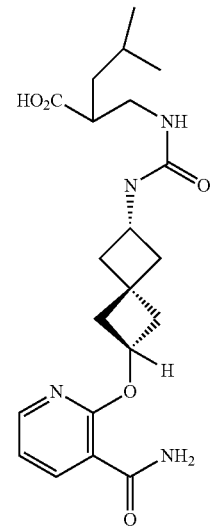

Intermediate 79a was prepared analogously to Intermediate 1c from Intermediate 1b by employing an unprotected β-amino acid in place of the α-amino acid methyl ester previously specified.

Example 79. 2-((((R)-6-(5-isobutyl-2,6-dioxotetrahydropyrimidin-1(2H)-yl)spiro[3.3]heptan-2-yl)oxy)nicotinamide A solution of 2-((3-(((R)-6-((3-carbamoylpyridin-2-yl)oxy)spiro[3.3]heptan-2-yl)ureido)methyl)-4-methylpentanoic acid (41.8 mg, 0.100 mmol) in toluene (1.0 mL) was treated with thionyl chloride (0.02 mL, 0.2 mmol) and the solution heated to 110° C. for 14 h.

The reaction mixture was concentrated under reduced pressure and the residue was purified via preparative LC/MS with the following conditions: Column: XBridge C18, 19×200 mm, 5-μm particles; Mobile Phase A: 5:95 acetonitrile: water with 0.10% trifluoroacetic acid; Mobile Phase B: 95:5 acetonitrile: water with 0.1% trifluoroacetic acid; Gradient: 15-55% B over 20 minutes, then a 5-minute hold at 100% B; Flow: 20 mL/min. Fractions containing Example 79 were combined and dried via centrifugal evaporation to furnish 2-((((R)-6-(5-isobutyl-2,6-dioxotetrahydropyrimidin-1(2H)-yl)spiro[3.3]heptan-2-yl)oxy)nicotinamide (1.7 mg, 4.1 μmol, 4.1% yield) as a 1:1 mixture of diastereomers. MS (ESI) m/z: 401.2 (M+H)+. 1H NMR (500 MHz, DMSO-d6) δ 8.36-8.09 (m, 2H), 7.66-7.47 (m, 3H), 7.10 (dd, J=7.4, 4.9 Hz, 1H), 5.24 (quin, J=7.0 Hz, 1H), 4.66 (quin, J=8.7 Hz, 1H), 3.00-2.86 (m, 1H), 2.78-2.61 (m, 3H), 2.42-2.31 (m, 1H), 2.29-2.15 (m, 3H), 1.73-1.51 (m, 2H), 1.26 (ddd, J=13.4, 8.1, 5.7 Hz, 1H), 1.00-0.80 (m, 6H). Analytical HPLC RT=1.51 min (Method A), purity=97%.

TABLE 1

| Ex. No. | Structure | Name | MS (ESI) (M + H) | ¹H NMR | LC RT<sup>a</sup> (min) and chiral conditions when separated |
|---|---|---|---|---|---|
| 2 | 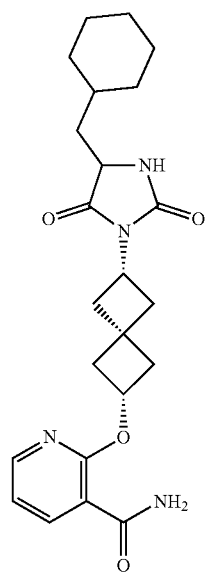 | 2-{[(αR)-6-[4-(cyclohexylmethyl)-2,5-dioxoimidazolidin-1-yl]spiro[3.3]heptan-2-yl]oxy}pyridine-3-carboxamide | 427.1 | 1H NMR (500 MHz, DMSO-d6) δ 8.28 (br s, 2H), 8.17 (dd, J = 7.5, 1.7 Hz, 1H), 7.75-7.52 (m, 2H), 7.11 (dd, J = 7.3, 4.9 Hz, 1H), 5.23 (quin, J = 7.2 Hz, 1H), 4.34 (quin, J = 8.8 Hz, 1H), 4.02 (br dd, J = 8.9, 4.0 Hz, 1H), 2.90-2.77 (m, 2H), 2.68 (dt, J = 11.4, 5.8 Hz, 1H), 2.50-2.46 (m, 1H), 2.36-2.13 (m, 4H), 1.73 (br d, J = 12.2 Hz, 1H), 1.70-1.58 (m, 4H), 1.58-1.51 (m, 1H), 1.47 (br d, J = 5.8 Hz, 1H), 1.35 (ddd, J = 13.4, 9.0, 4.7 Hz, 1H), 1.27-1.08 (m, 3H), 0.97-0.79 (m, 2H) | 1.76 Chiralpak IC, 21x250 mm, 5 mm, 75% CO2/25% methanol-ACN 50-50, Flow 100 mL/min: t<sub>R</sub> = 23.77 min |
| 3 | 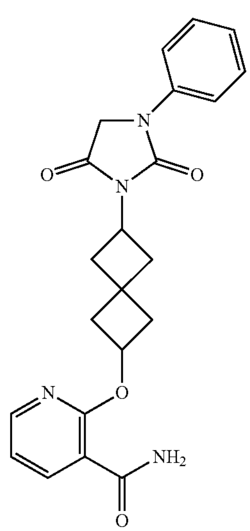 [SMILES: NC(=O)c1cccnc1OC1CC2(C1)CC(N1C(=O)CN(c3ccccc3)C1=O)C2] | 2-{[6-(2,5-dioxo-3-phenylimidazolidin-1-yl)spiro[3.3]heptan-2-yl]oxy}pyridine-3-carboxamide | 407.1 | 1H NMR (500 MHz, DMSO-d6) δ 8.33-8.23 (m, 1H), 8.17 (dd, J = 7.3, 1.8 Hz, 1H), 7.75-7.53 (m, 4H), 7.39 (br t, J = 7.9 Hz, 2H), 7.19-7.04 (m, 2H), 5.24 (quin, J = 7.0 Hz, 1H), 4.53-4.35 (m, 3H), 2.91 (br t, J = 10.2 Hz, 2H), 2.75-2.64 (m, 1H), 2.59-2.53 (m, 1H), 2.44-2.33 (m, 1H), 2.32-2.18 (m, 3H) | 1.6 |

TABLE 1-continued

| Ex. No. | Structure | Name | MS (ESI) (M + H) | ¹H NMR | LC RT$^a$ (min) and chiral conditions when separated |
|---|---|---|---|---|---|
| 4 | 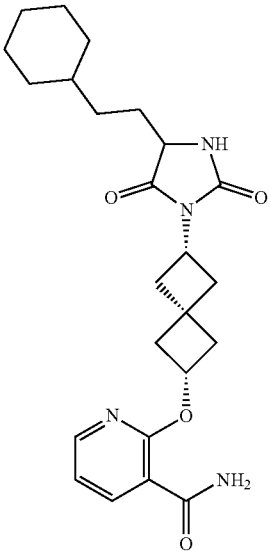 | 2-{[(αR)-6-[4-(2-cyclohexylethyl)-2,5-dioxoimidazolidin-1-yl]spiro[3.3]heptan-2-yl]oxy}pyridine-3-carboxamide | 440.1 | 1H NMR (500 MHz, DMSO-d6) δ 8.27 (dd, J = 4.8, 1.9 Hz, 1H), 8.18 (dd, J = 7.4, 1.9 Hz, 1H), 8.07 (s, 1H), 7.53 (br s, 2H), 7.10 (dd, J = 7.4, 4.9 Hz, 1H), 5.25 (quin, J = 7.0 Hz, 1H), 4.33 (quin, J = 8.8 Hz, 1H), 2.84 (q, J = 10.1 Hz, 2H), 2.75-2.63 (m, 1H), 2.54-2.52 (m, 1H), 2.38-2.29 (m, 1H), 2.25 (dt, J = 11.8, 7.3 Hz, 3H), 1.78-1.57 (m, 6H), 1.56-1.45 (m, 1H), 1.32-1.07 (m, 7H), 0.86 (br d, J = 8.1 Hz, 2H) | 1.89 |
| 5 | 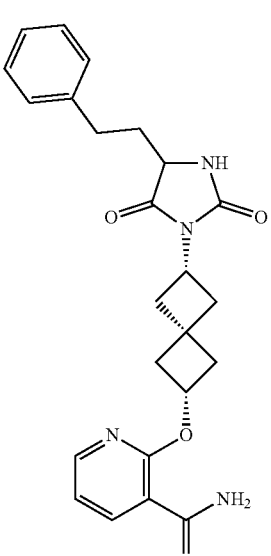 | 2-{[(αR)-6-[2,5-dioxo-4-(2-phenylethyl)imidazolidin-1-yl]spiro[3.3]heptan-2-yl]oxy}pyridine-3-carboxamide | 435.1 | 1H NMR (500 MHz, DMSO-d6) δ 8.36 (s, 1H), 8.27 (dd, J = 4.7, 1.7 Hz, 1H), 8.17 (dd, J = 7.5, 1.7 Hz, 1H), 7.74-7.56 (m, 2H), 7.34-7.25 (m, 2H), 7.23-7.17 (m, 3H), 7.11 (dd, J = 7.5, 5.0 Hz, 1H), 5.21 (quin, J = 7.1 Hz, 1H), 4.31 (quin, J = 8.9 Hz, 1H), 3.93 (br dd, J = 6.7, 4.9 Hz, 1H), 2.82 (dt, J = 14.0, 10.4 Hz, 2H), 2.72-2.59 (m, 3H), 2.50-2.45 (m, 1H), 2.33-2.14 (m, 4H), 2.02-1.89 (m, 1H), 1.81 (dq, J = 14.2, 7.4 Hz, 1H) | 1.57 Chiralpak AD, 30x250 mm, 5 mm 70% CO2/30% IPA w/ 0.1% DEA, Flow 100 mL/min: $t_R$ = 10.27 min |

TABLE 1-continued

| Ex. No. | Structure | Name | MS (ESI) (M + H) | ¹H NMR | LC RT[a] (min) and chiral conditions when separated |
|---|---|---|---|---|---|
| 6 | 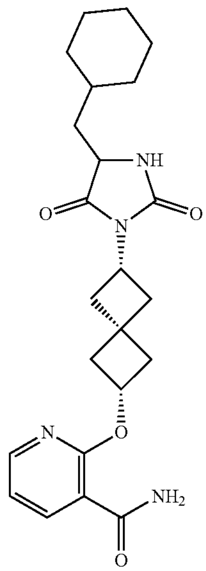 | 2-{[(αR)-6-(4-cyclohexylmethyl-2,5-dioxoimidazolidin-1-yl)spiro[3.3]heptan-2-yl]oxy}pyridine-3-carboxamide | 427.2 | 1H NMR (500 MHz, DMSO-d6) δ 8.27 (br s, 2H), 8.17 (dd, J = 7.3, 1.5 Hz, 1H), 7.74-7.53 (m, 2H), 7.11 (dd, J = 7.3, 4.9 Hz, 1H), 5.22 (quin, J = 7.1 Hz, 1H), 4.33 (quin, J = 8.8 Hz, 1H), 4.01 (br dd, J = 8.9, 4.0 Hz, 1H), 2.83 (q, J = 9.7 Hz, 2H), 2.67 (dt, J = 11.0, 5.8 Hz, 1H), 2.50-2.46 (m, 1H), 2.35-2.14 (m, 4H), 1.72 (br d, J = 12.2 Hz, 1H), 1.69-1.58 (m, 4H), 1.57-1.50 (m, 1H), 1.46 (br s, 1H), 1.35 (ddd, J = 13.4, 8.9, 4.9 Hz, 1H), 1.27-1.06 (m, 3H), 0.97-0.76 (m, 2H) | 1.75 Chiralpak AD, 30x250 mm, 5 mm 70% CO2/30% IPA w/ 0.1% DEA Flow 100 mL/min: t$_R$ = 26.33 min |
| 7 | 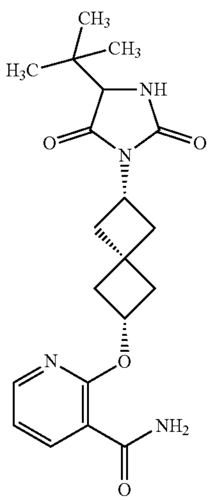 | 2-{[(αR)-6-(4-tert-butyl-2,5-dioxoimidazolidin-1-yl)spiro[3.3]heptan-2-yl]oxy}pyridine-3-carboxamide | 387.1 | 1H NMR (500 MHz, DMSO-d6) δ 8.26 (dd, J = 4.8, 1.8 Hz, 1H), 8.17 (dd, J = 7.5, 1.8 Hz, 1H), 8.10 (s, 1H), 7.53 (br d, J = 19.4 Hz, 2H), 7.10 (dd, J = 7.4, 5.0 Hz, 1H), 5.23 (quin, J = 7.0 Hz, 1H), 4.32 (quin, J = 8.7 Hz, 1H), 3.64 (s, 1H), 2.83 (q, J = 9.3 Hz, 2H), 2.74-2.63 (m, 1H), 2.35-2.14 (m, 4H), 0.93 (s, 9H).[b] | 1.44 Chiralpak AD, 30x250 mm, 5 mm 60% CO2/40% methanol w/0.1% DEA Flow 100 mL/min: t$_R$ = 3.63 min |
| 8 | 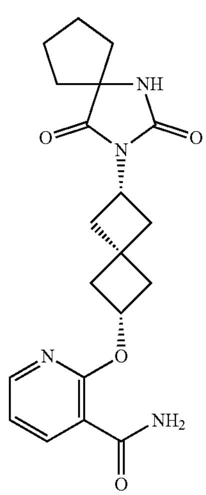 | 2-{[(αR)-6-{2,4-dioxo-1,3-diazaspiro[4.4]nonan-3-yl}spiro[3.3]heptan-2-yl]oxy}pyridine-3-carboxamide | 385.2 | 1H NMR (500 MHz, DMSO-d6) δ 8.47 (s, 1H), 8.27 (dd, J = 4.9, 1.8 Hz, 1H), 8.17 (dd, J = 7.5, 1.7 Hz, 1H), 7.75-7.53 (m, 2H), 7.11 (dd, J = 7.3, 4.9 Hz, 1H), 5.23 (quin, J = 7.2 Hz, 1H), 4.34 (quin, J = 8.8 Hz, 1H), 2.91-2.77 (m, 2H), 2.68 (dt, J = 11.4, 5.8 Hz, 1H), 2.50-2.47 (m, 1H), 2.38-2.29 (m, 1H), 2.28-2.16 (m, 3H), 1.98-1.86 (m, 2H), 1.79-1.60 (m, 6H) | 1.32 |

TABLE 1-continued

| Ex. No. | Structure | Name | MS (ESI) (M + H) | ¹H NMR | LC RT$^a$ (min) and chiral conditions when separated |
|---|---|---|---|---|---|
| 9 | 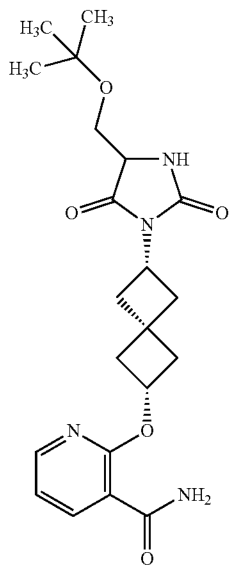 | 2-{[(αR)-6-(4-tert-butoxymethyl-2,5-dioxoimidazolidin-1-yl)spiro[3.3]heptan-2-yl]oxy}pyridine-3-carboxamide | 417.3 | 1H NMR (500 MHz, DMSO-d6) δ 8.27 (dd, J = 4.7, 1.8 Hz, 1H), 8.18 (dd, J = 7.4, 1.7 Hz, 1H), 7.95 (s, 1H), 7.53 (br s, 2H), 7.10 (dd, J = 7.4, 4.9 Hz, 1H), 5.25 (quin, J = 7.0 Hz, 1H), 4.32 (quin, J = 8.8 Hz, 1H), 4.02 (br s, 1H), 3.61-3.47 (m, 2H), 2.93-2.78 (m, 2H), 2.68 (dt, J = 11.5, 5.8 Hz, 1H), 2.37-2.12 (m, 4H), 1.10 (s, 9H).$^b$ | 1.36 Chiralpak AD, 30x250 mm, 5 mm 80% CO2/20% IPA w/0.1% DEA Flow 100 mL/min: t$_R$ = 11.73 min |
| 10 | 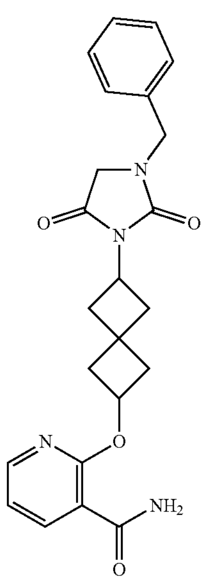 [SMILES: NC(=O)c1cccnc1OC1CC2(C1)CC(N1C(=O)CN(Cc3ccccc3)C1=O)C2] | 2-{[6-(3-benzyl-2,5-dioxoimidazolidin-1-yl)spiro[3.3]heptan-2-yl]oxy}pyridine-3-carboxamide | 421.0 | 1H NMR (500 MHz, DMSO-d6) δ 8.27 (dd, J = 4.7, 1.7 Hz, 1H), 8.17 (dd, J = 7.3, 1.8 Hz, 1H), 7.76-7.50 (m, 2H), 7.41-7.33 (m, 2H), 7.32-7.23 (m, 3H), 7.11 (dd, J = 7.5, 5.0 Hz, 1H), 5.23 (quin, J = 7.1 Hz, 1H), 4.47 (s, 2H), 4.39 (quin, J = 8.8 Hz, 1H), 3.82 (s, 2H), 2.87 (br t, J = 9.9 Hz, 2H), 2.68 (dt, J = 11.4, 5.8 Hz, 1H), 2.53 (br s, 1H), 2.38-2.30 (m, 1H), 2.29-2.18 (m, 3H)$^b$ | 1.56 |

TABLE 1-continued

| Ex. No. | Structure | Name | MS (ESI) (M + H) | ¹H NMR | LC RT[a] (min) and chiral conditions when separated |
|---|---|---|---|---|---|
| 11 | 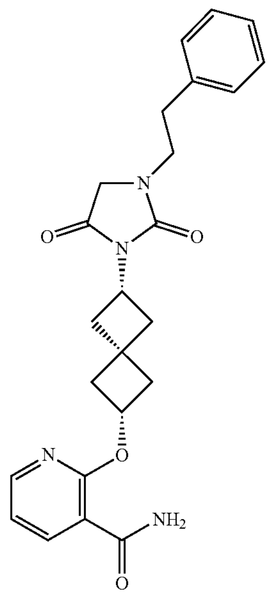 | 2-{[(αR)-6-[2,5-dioxo-3-(2-phenylethyl)imidazolidin-1-yl]spiro[3.3]heptan-2-yl]oxy}pyridine-3-carboxamide | 435.2 | 1H NMR (500 MHz, DMSO-d6) δ 8.27 (dd, J = 4.8, 1.9 Hz, 1H), 8.16 (dd, J = 7.5, 1.9 Hz, 1H), 7.76-7.56 (m, 2H), 7.34-7.27 (m, 2H), 7.26-7.18 (m, 3H), 7.11 (dd, J = 7.4, 4.9 Hz, 1H), 5.21 (quin, J = 7.1 Hz, 1H), 4.32 (quin, J = 8.8 Hz, 1H), 3.87 (s, 2H), 3.57-3.41 (m, 2H), 2.88-2.75 (m, 4H), 2.66 (dt, J = 11.5, 5.8 Hz, 1H), 2.49-2.44 (m, 1H), 2.33-2.13 (m, 4H). | 1.62 |
| 12 | 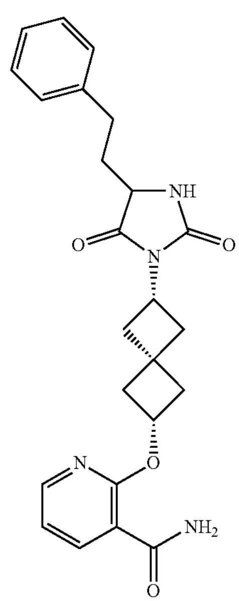 | 2-{[(αR)-6-(4-(2-phenylethyl)-2,5-dioxoimidazolidin-1-yl)spiro[3.3]heptan-2-yl]oxy}pyridine-3-carboxamide | 435.1 | 1H NMR (500 MHz, DMSO-d6) δ 8.37 (s, 1H), 8.27 (dd, J = 4.7, 1.7 Hz, 1H), 8.17 (dd, J = 7.5, 1.7 Hz, 1H), 7.74-7.56 (m, 2H), 7.34-7.25 (m, 2H), 7.25-7.17 (m, 3H), 7.11 (dd, J = 7.3, 4.9 Hz, 1H), 5.22 (quin, J = 7.1 Hz, 1H), 4.32 (quin, J = 8.8 Hz, 1H), 3.98-3.91 (m, 1H), 2.93-2.75 (m, 2H), 2.72-2.59 (m, 3H), 2.50-2.45 (m, 1H), 2.36-2.14 (m, 4H), 2.01-1.90 (m, 1H), 1.87-1.74 (m, 1H) | 1.56 Chiralpak AD, 30x250 mm, 5 mm 70% CO2/30% IPA w/ 0.1% DEA Flow 100 mL/min: t_R = 8.23 min |

TABLE 1-continued

| Ex. No. | Structure | Name | MS (ESI) (M + H) | ¹H NMR | LC RT$^a$ (min) and chiral conditions when separated |
|---|---|---|---|---|---|
| 13 | 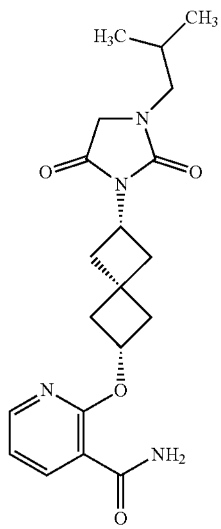 | 2-{[(αR)-6-[3-(2-methylpropyl)-2,5-dioxoimidazolidin-1-yl]spiro[3.3]heptan-2-yl]oxy}pyridine-3-carboxamide | 386.9 | 1H NMR (500 MHz, DMSO-d6) δ 8.27 (dd, J = 4.9, 1.8 Hz, 1H), 8.17 (dd, J = 7.5, 1.7 Hz, 1H), 7.82-7.51 (m, 2H), 7.11 (dd, J = 7.3, 4.9 Hz, 1H), 5.23 (quin, J = 7.1 Hz, 1H), 4.37 (quin, J = 8.8 Hz, 1H), 3.91 (s, 2H), 3.06 (d, J = 7.3 Hz, 2H), 2.86 (br t, J = 10.1 Hz, 2H), 2.68 (dt, J = 11.5, 5.7 Hz, 1H), 2.49 (br s, 1H), 2.36-2.29 (m, 1H), 2.28-2.15 (m, 3H), 1.85 (dquin, J = 13.5, 6.8 Hz, 1H), 0.85 (d, J = 6.4 Hz, 6H) | 1.47 |
| 14 | 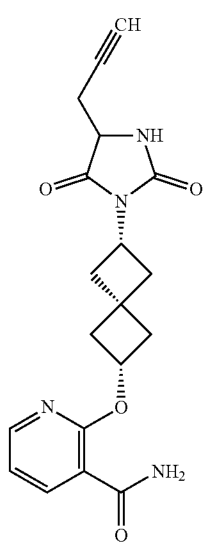 | 2-{[(αR)-6-[2,5-dioxo-4-(prop-2-yn-1-yl)imidazolidin-1-yl]spiro[3.3]heptan-2-yl]oxy}pyridine-3-carboxamide | 369.1 | 1H NMR (500 MHz, DMSO-d6) δ 8.31-8.21 (m, 2H), 8.17 (dd, J = 7.3, 1.5 Hz, 1H), 7.73-7.55 (m, 2H), 7.11 (dd, J = 7.3, 4.9 Hz, 1H), 5.22 (quin, J = 7.2 Hz, 1H), 4.34 (quin, J = 8.8 Hz, 1H), 4.13 (t, J = 3.8 Hz, 1H), 2.91-2.78 (m, 3H), 2.73-2.64 (m, 1H), 2.58 (br dd, J = 7.2, 3.8 Hz, 2H), 2.49 (br s, 1H), 2.36-2.16 (m, 4H) | 1.23 Chiralpak AD, 30x250 mm, 5 mm 70% CO2/30% IPA w/0.1% DEA Flow 100 mL/min: $t_R$ = 7.24 min |

TABLE 1-continued

| Ex. No. | Structure | Name | MS (ESI) (M + H) | ¹H NMR | LC RT[a] (min) and chiral conditions when separated |
|---|---|---|---|---|---|
| 15 | 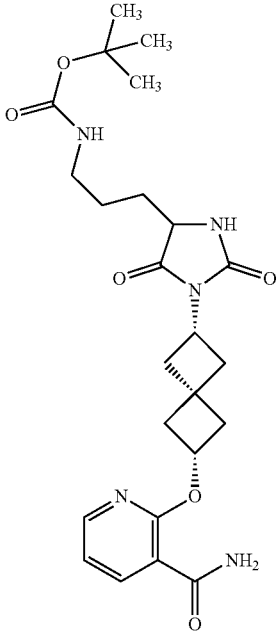 | tert-butyl N-(3-{2,5-dioxo-1-[(αR)-6-[(3-carbamoylpyridin-2-yl)oxy]spiro[3.3]heptan-2-yl]imidazolidin-4-yl}propyl)carbamate | 488.1 | 1H NMR (500 MHz, DMSO-d6) δ 8.27 (dd, J = 4.9, 1.9 Hz, 1H), 8.18 (dd, J = 7.4, 1.9 Hz, 1H), 8.08 (s, 1H), 7.53 (br s, 2H), 7.10 (dd, J = 7.4, 4.9 Hz, 1H), 6.67 (br s, 1H), 5.25 (quin, J = 7.0 Hz, 1H), 4.33 (quin, J = 8.8 Hz, 1H), 3.95 (br t, J = 5.3 Hz, 1H), 2.93 (q, J = 6.3 Hz, 2H), 2.89-2.76 (m, 2H), 2.68 (dt, J = 11.4, 5.8 Hz, 1H), 2.38-2.29 (m, 1H), 2.28-2.15 (m, 3H), 1.75-1.62 (m, 1H), 1.57-1.32 (m, 12H).[b] | 1.42 Chiralpak AD, 30x250 mm, 5 mm 75% CO2/25% IPA w/0.1% DEA Flow 100 mL/min: t_R = 12.18 min |
| 16 | 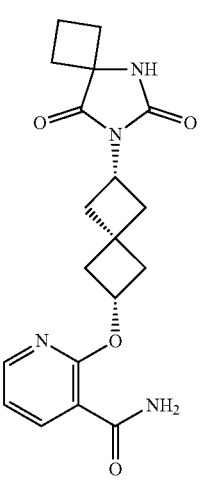 | 2-{[(αR)-6-{6,8-dioxo-5,7-diazaspiro[3.4]octan-7-yl}spiro[3.3]heptan-2-yl]oxy}pyridine-3-carboxamide | 371.0 | 1H NMR (500 MHz, DMSO-d6) δ 8.60 (s, 1H), 8.27 (dd, J = 4.7, 1.7 Hz, 1H), 8.17 (dd, J = 7.5, 1.7 Hz, 1H), 7.79-7.50 (m, 2H), 7.11 (dd, J = 7.3, 4.9 Hz, 1H), 5.23 (quin, J = 7.2 Hz, 1H), 4.32 (quin, J = 8.8 Hz, 1H), 2.91-2.77 (m, 2H), 2.67 (dt, J = 11.4, 5.9 Hz, 1H), 2.50-2.47 (m, 1H), 2.43-2.15 (m, 8H), 1.97-1.85 (m, 1H), 1.81-1.68 (m, 1H) | 1.21 |

TABLE 1-continued

| Ex. No. | Structure | Name | MS (ESI) (M + H) | ¹H NMR | LC RT[a] (min) and chiral conditions when separated |
|---|---|---|---|---|---|
| 17 | 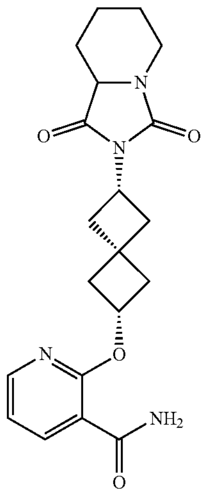 | 2-{[(αR)-6-{1,3-dioxo-hexahydro-1H-piperidino[1,2-c]imidazolidin-2-yl}spiro[3.3]heptan-2-yl]oxy}pyridine-3-carboxamide | 385.0 | 1H NMR (500 MHz, DMSO-d6) δ 8.28 (dd, J = 4.7, 1.7 Hz, 1H), 8.17 (dd, J = 7.3, 1.8 Hz, 1H), 7.81-7.51 (m, 2H), 7.11 (dd, J = 7.3, 4.9 Hz, 1H), 5.23 (quin, J = 7.2 Hz, 1H), 4.36 (quin, J = 8.8 Hz, 1H), 4.00-3.83 (m, 2H), 2.94-2.74 (m, 3H), 2.68 (dt, J = 11.6, 5.8 Hz, 1H), 2.49 (br s, 1H), 2.38-2.30 (m, 1H), 2.29-2.18 (m, 3H), 1.98 (br dd, J = 9.0, 3.5 Hz, 1H), 1.84 (br d, J = 13.1 Hz, 1H), 1.65 (br d, J = 12.8 Hz, 1H), 1.46 (q, J = 13.1 Hz, 1H), 1.34-1.11 (m, 2H) | 1.28 Chiralpak AD, 30x250 mm, 5 mm 75% CO2/25% IPA-ACN 50-50 w/0.1% DEA Flow 100 mL/min: $t_R$ = 18.60 min |
| 18 | 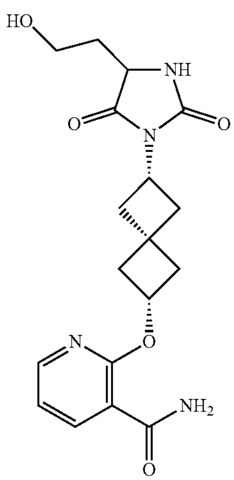 | 2-{[(αR)-6-[2,5-dioxo-4-(2-hydroxyethyl)imidazolidin-1-yl]spiro[3.3]heptan-2-yl]oxy}pyridine-3-carboxamide | 375.1 | 1H NMR (500 MHz, DMSO-d6) δ 8.31-8.26 (m, 1H), 8.21 (s, 1H), 8.17 (dd, J = 7.3, 1.5 Hz, 1H), 7.80-7.51 (m, 2H), 7.11 (dd, J = 7.3, 4.9 Hz, 1H), 5.23 (quin, J = 7.1 Hz, 1H), 4.33 (quin, J = 8.9 Hz, 1H), 4.02 (br dd, J = 7.3, 4.6 Hz, 1H), 3.62-3.32 (m, 2H), 2.85 (q, J = 10.6 Hz, 2H), 2.74-2.62 (m, 1H), 2.50-2.45 (m, 1H), 2.37-2.15 (m, 4H), 1.94-1.81 (m, 1H), 1.70-1.58 (m, 1H) | 0.87 Chiralpak OD, 30x250 mm, 5 mm 75% CO2/25% IPA-ACN 50-50 w/0.1% DEA Flow 100 mL/min: $t_R$ = 36.04 min |
| 19 | 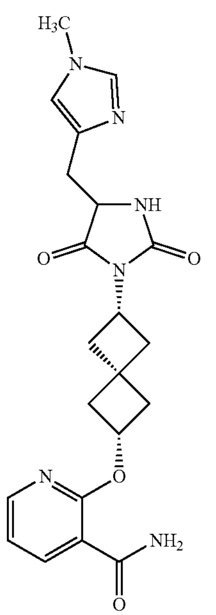 | 2-{[(αR)-6-[2,5-dioxo-4-(1-methyl-4-imidazylmethyl)imidazolidin-1-yl]spiro[3.3]heptan-2-yl]oxy}pyridine-3-carboxamide | 425.2 | 1H NMR (500 MHz, DMSO-d6) δ 8.27 (dd, J = 4.8, 1.8 Hz, 1H), 8.18 (dd, J = 7.4, 1.8 Hz, 1H), 7.86 (s, 1H), 7.54 (br s, 2H), 7.46 (s, 1H), 7.10 (dd, J = 7.4, 4.9 Hz, 1H), 6.82 (s, 1H), 5.25 (quin, J = 7.1 Hz, 1H), 4.28 (quin, J = 8.8 Hz, 1H), 4.15 (t, J = 5.3 Hz, 1H), 3.59 (s, 3H), 2.89 (dd, J = 14.8, 4.4 Hz, 1H), 2.85-2.73 (m, 3H), 2.71-2.63 (m, 1H), 2.35-2.12 (m, 4H)[b] | 0.76 Chiralpak AD, 30x250 mm, 5 mm 60% CO2/40% IPA w/0.1% DEA Flow 100 mL/min: $t_R$ = 7.75 min |

TABLE 1-continued

| Ex. No. | Structure | Name | MS (ESI) (M + H) | ¹H NMR | LC RT[a] (min) and chiral conditions when separated |
|---|---|---|---|---|---|
| 20 | 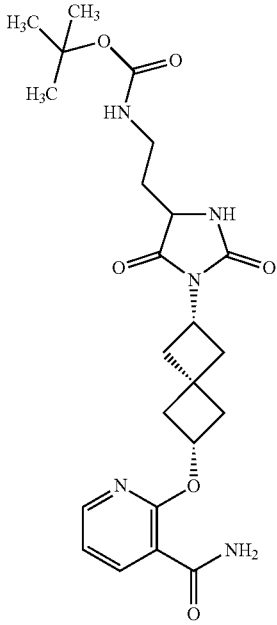 | tert-butyl N-(2-{2,5-dioxo-1-[(αR)-6-[(3-carbamoylpyridin-2-yl)oxy]spiro[3.3]heptan-2-yl]imidazolidin-4-yl}ethyl)carbamate | 474.2 | 1H NMR (500 MHz, DMSO-d6) δ 8.27 (dd, J = 4.7, 1.7 Hz, 1H), 8.23-8.12 (m, 2H), 7.75-7.55 (m, 2H), 7.11 (dd, J = 7.5, 5.0 Hz, 1H), 6.84 (br s, 1H), 5.22 (quin, J = 7.2 Hz, 1H), 4.32 (quin, J = 8.8 Hz, 1H), 4.02-3.93 (m, 1H), 3.01 (q, J = 6.7 Hz, 2H), 2.84 (q, J = 9.2 Hz, 2H), 2.67 (dt, J = 11.4, 5.8 Hz, 1H), 2.50-2.44 (m, 1H), 2.37-2.16 (m, 4H), 1.87-1.74 (m, 1H), 1.61 (dt, J = 13.9, 7.1 Hz, 1H), 1.38 (s, 9H) | 1.34 Chiralpak AD, 30x250 mm, 5 mm 65% CO2/35% methanol-CAN 50-50 Flow 100 mL/min: $t_R$ = 8.46 min |
| 21 | 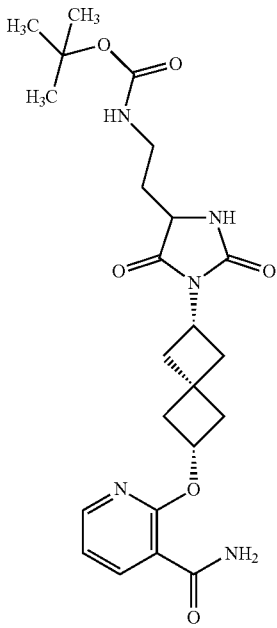 | tert-butyl N-(2-{2,5-dioxo-1-[(αR)-6-[(3-carbamoylpyridin-2-yl)oxy]spiro[3.3]heptan-2-yl]imidazolidin-4-yl}ethyl)carbamate | 474.2 | 1H NMR (500 MHz, DMSO-d6) δ 8.28 (dd, J = 4.7, 1.7 Hz, 1H), 8.23-8.10 (m, 2H), 7.75-7.50 (m, 2H), 7.11 (dd, J = 7.5, 5.0 Hz, 1H), 6.84 (br s, 1H), 5.23 (quin, J = 7.2 Hz, 1H), 4.33 (quin, J = 8.8 Hz, 1H), 4.01-3.93 (m, 1H), 3.02 (q, J = 6.5 Hz, 2H), 2.85 (q, J = 10.7 Hz, 2H), 2.67 (dt, J = 10.9, 5.7 Hz, 1H), 2.51-2.45 (m, 1H), 2.38-2.14 (m, 4H), 1.81 (br dd, J = 13.0, 5.0 Hz, 1H), 1.68-1.54 (m, 1H), 1.39 (s, 9H) | 1.33 Chiralpak AD, 30x250 mm, 5 mm 65% CO2/35% methanol-CAN 50-50 Flow 100 mL/min: $t_R$ = 12.19 min |

TABLE 1-continued

| Ex. No. | Structure | Name | MS (ESI) (M + H) | ¹H NMR | LC RT$^a$ (min) and chiral conditions when separated |
|---|---|---|---|---|---|
| 22 | 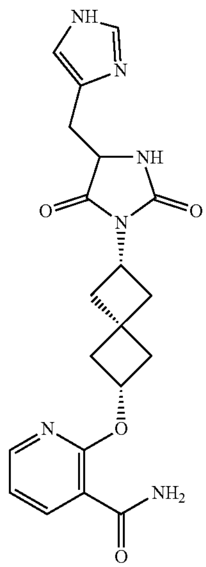 | 2-{[(αR)-6-{4-[(1H-imidazol-4-yl)methyl]-2,5-dioxoimidazolidin-1-yl}spiro[3.3]heptan-2-yl]oxy}pyridine-3-carboxamide | 411.1 | 1H NMR (500 MHz, DMSO-d6) δ 8.31-8.23 (m, 1H), 8.16 (dd, J = 7.3, 1.5 Hz, 1H), 8.05 (s, 1H), 7.65 (br d, J = 7.3 Hz, 3H), 7.11 (dd, J = 7.3, 5.2 Hz, 1H), 6.83 (s, 1H), 5.19 (quin, J = 7.0 Hz, 1H), 4.31-4.15 (m, 2H), 2.99-2.90 (m, 1H), 2.89-2.81 (m, 1H), 2.74 (td, J = 9.9, 5.8 Hz, 2H), 2.64 (dt, J = 11.3, 5.6 Hz, 1H), 2.51-2.44 (m, 1H), 2.32-2.07 (m, 4H) | 0.77 |
| 23 | 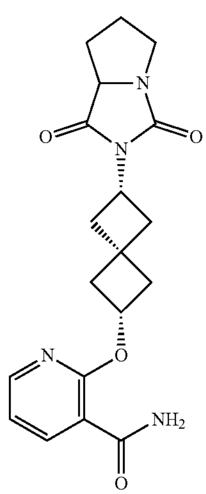 | 2-{[(αR)-6-{1,3-dioxo-hexahydro-1H-pyrrolo[1,2-c]imidazolidin-2-yl}spiro[3.3]heptan-2-yl]oxy}pyridine-3-carboxamide | 371.0 | 1H NMR (500 MHz, DMSO-d6) δ 8.27 (dd, J = 4.7, 1.7 Hz, 1H), 8.17 (dd, J = 7.3, 1.5 Hz, 1H), 7.77-7.53 (m, 2H), 7.11 (dd, J = 7.5, 5.0 Hz, 1H), 5.22 (quin, J = 7.1 Hz, 1H), 4.30 (quin, J = 8.8 Hz, 1H), 4.11 (t, J = 8.2 Hz, 1H), 3.55-3.42 (m, 1H), 3.18-3.07 (m, 1H), 2.90-2.72 (m, 2H), 2.68 (dt, J = 11.4, 5.9 Hz, 1H), 2.48 (br s, 1H), 2.38-2.30 (m, 1H), 2.28-2.18 (m, 3H), 2.14-2.05 (m, 1H), 2.03-1.87 (m, 2H), 1.71-1.57 (m, 1H) | 1.21 Chiralpak AD, 30x250 mm, 5 mm 60% CO2/40% methanol-ACN 50-50 Flow 100 mL/min: t$_R$ = 9.77 min |

TABLE 1-continued

| Ex. No. | Structure | Name | MS (ESI) (M + H) | $^1$H NMR | LC RT[a] (min) and chiral conditions when separated |
|---|---|---|---|---|---|
| 25 | 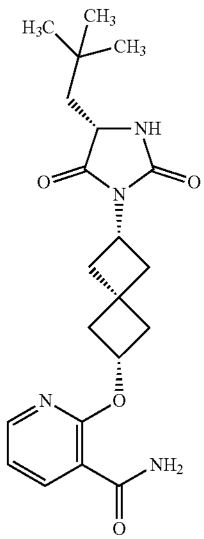 | 2-{[(αR)-6-[(4S)-4-(2,2-dimethylpropyl)-2,5-dioxoimidazolidin-1-yl]spiro[3.3]heptan-2-yl]oxy}pyridine-3-carboxamide | 401.2 | 1H NMR (500 MHz, DMSO-d6) δ 8.25 (dd, J = 4.8, 1.8 Hz, 1H), 8.17 (dd, J = 7.4, 1.8 Hz, 1H), 7.96 (s, 1H), 7.68-7.42 (m, 2H), 7.10 (dd, J = 7.5, 4.9 Hz, 1H), 5.23 (quin, J = 7.0 Hz, 1H), 4.33 (quin, J = 8.8 Hz, 1H), 3.95 (br d, J = 8.4 Hz, 1H), 3.19 (br d, J = 4.1 Hz, 1H), 2.89-2.77 (m, 2H), 2.72-2.63 (m, 1H), 2.38-2.28 (m, 1H), 2.28-2.18 (m, 2H), 1.73 (dd, J = 14.3, 2.7 Hz, 1H), 1.34 (dd, J = 14.3, 8.6 Hz, 1H), 0.92 (s, 9H)[b] | 1.60 |
| 26 | 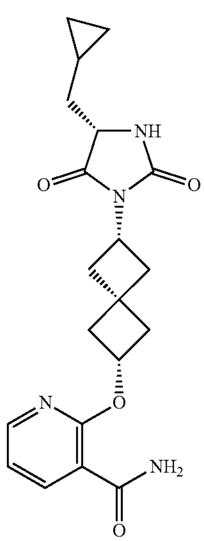 | 2-{[(αR)-6-[(4S)-4-(cyclopropylmethyl)-2,5-dioxoimidazolidin-1-yl]spiro[3.3]heptan-2-yl]oxy}pyridine-3-carboxamide | 385.0 | 1H NMR (500 MHz, DMSO-d6) δ 8.28-8.15 (m, 2H), 8.10 (dd, J = 7.5, 1.7 Hz, 1H), 7.67-7.46 (m, 2H), 7.04 (dd, J = 7.3, 5.2 Hz, 1H), 5.15 (quin, J = 7.1 Hz, 1H), 4.27 (quin, J = 8.8 Hz, 1H), 3.94 (t, J = 5.0 Hz, 1H), 2.78 (td, J = 10.1, 3.8 Hz, 2H), 2.61 (dt, J = 11.4, 5.8 Hz, 1H), 2.30-2.06 (m, 4H), 1.63-1.51 (m, 1H), 1.39 (dt, J = 14.0, 6.9 Hz, 1H), 0.73-0.56 (m, 1H), 0.40-0.23 (m, 2H), 0.12--0.08 (m, 2H).[b] | 1.33 |

TABLE 1-continued

| Ex. No. | Structure | Name | MS (ESI) (M + H) | ¹H NMR | LC RT[a] (min) and chiral conditions when separated |
|---|---|---|---|---|---|
| 27 | 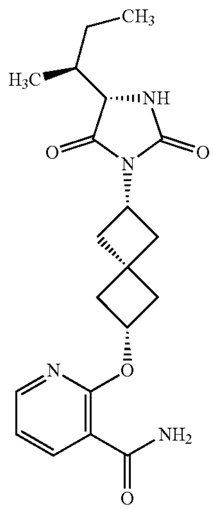 | 2-{[(αR)-6-[(4S)-4-[(2S)-butan-2-yl]-2,5-dioxoimidazolidin-1-yl]spiro[3.3]heptan-2-yl]oxy}pyridine-3-carboxamide | 386.8 | 1H NMR (500 MHz, DMSO-d6) δ 8.27 (dd, J = 4.8, 1.8 Hz, 1H), 8.23 (s, 1H), 8.16 (dd, J = 7.4, 1.8 Hz, 1H), 7.79-7.53 (m, 2H), 7.11 (dd, J = 7.4, 4.9 Hz, 1H), 5.21 (quin, J = 7.1 Hz, 1H), 4.33 (quin, J = 8.7 Hz, 1H), 4.00-3.85 (m, 1H), 2.90-2.78 (m, 2H), 2.67 (dt, J = 11.3, 5.9 Hz, 1H), 2.34-2.14 (m, 4H), 1.76 (br d, J = 2.7 Hz, 1H), 1.33-1.22 (m, 1H), 1.21-1.09 (m, 1H), 0.90 (d, J = 6.9 Hz, 3H), 0.84 (t, J = 7.4 Hz, 3H).[b] | 1.54 |
| 28 | 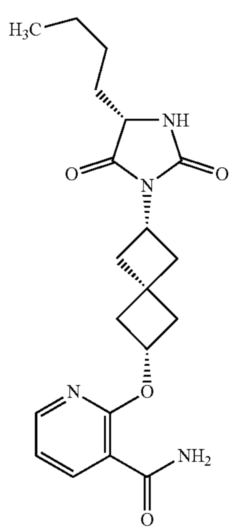 | 2-{[(αR)-6-[(4S)-4-butyl-2,5-dioxoimidazolidin-1-yl]spiro[3.3]heptan-2-yl]oxy}pyridine-3-carboxamide | 387.2 | 1H NMR (500 MHz, DMSO-d6) δ 8.27 (dd, J = 4.7, 1.8 Hz, 1H), 8.18 (dd, J = 7.4, 1.8 Hz, 1H), 8.09 (s, 1H), 7.53 (br s, 2H), 7.10 (dd, J = 7.4, 4.9 Hz, 1H), 5.25 (quin, J = 7.0 Hz, 1H), 4.34 (quin, J = 8.8 Hz, 1H), 3.94 (br t, J = 5.7 Hz, 1H), 2.85 (q, J = 10.3 Hz, 2H), 2.68 (dt, J = 11.6, 5.8 Hz, 1H), 2.39-2.29 (m, 1H), 2.29-2.18 (m, 3H), 1.75-1.62 (m, 1H), 1.58-1.46 (m, 1H), 1.38-1.21 (m, 4H), 0.88 (br t, J = 6.9 Hz, 3H).[b] | 1.44 |

TABLE 1-continued

| Ex. No. | Structure | Name | MS (ESI) (M + H) | ¹H NMR | LC RT[a] (min) and chiral conditions when separated |
|---|---|---|---|---|---|
| 29 | 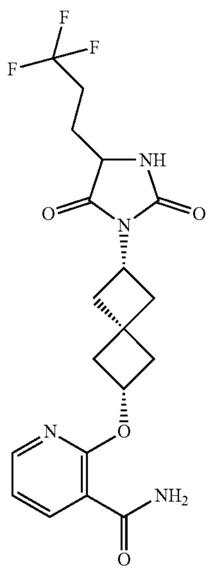 | 2-{[(αR)-6-[2,5-dioxo-4-(3,3,3-trifluoropropyl)imidazolidin-1-yl]spiro[3.3]heptan-2-yl]oxy}pyridine-3-carboxamide | 427.0 | 1H NMR (500 MHz, DMSO-d6) δ 8.37-8.25 (m, 2H), 8.17 (dd, J = 7.3, 1.8 Hz, 1H), 7.77-7.53 (m, 2H), 7.11 (dd, J = 7.3, 4.9 Hz, 1H), 5.22 (quin, J = 7.1 Hz, 1H), 4.33 (quin, J = 8.7 Hz, 1H), 4.13-4.02 (m, 1H), 3.18 (d, J = 4.9 Hz, 1H), 2.90-2.78 (m, 2H), 2.67 (dt, J = 11.7, 5.6 Hz, 1H), 2.46-2.13 (m, 6H), 1.98-1.84 (m, 1H), 1.82-1.61 (m, 1H) | 1.41 |
| 30 | 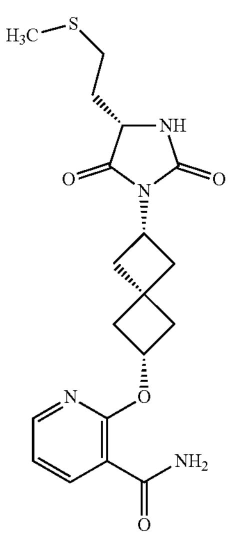 | 2-{[(αR)-6-[(4S)-4-[2-(methylsulfanyl)ethyl]-2,5-dioxoimidazolidin-1-yl]spiro[3.3]heptan-2-yl]oxy}pyridine-3-carboxamide | 405.2 | 1H NMR (500 MHz, DMSO-d6) δ 8.32-8.23 (m, 2H), 8.17 (dd, J = 7.5, 1.7 Hz, 1H), 7.75-7.51 (m, 2H), 7.11 (dd, J = 7.3, 4.9 Hz, 1H), 5.23 (quin, J = 7.2 Hz, 1H), 4.33 (quin, J = 8.8 Hz, 1H), 4.12-4.03 (m, 1H), 2.92-2.78 (m, 2H), 2.68 (dt, J = 11.4, 5.8 Hz, 1H), 2.36-2.15 (m, 4H), 2.05 (s, 3H), 1.99-1.88 (m, 1H), 1.78 (dq, J = 14.1, 7.2 Hz, 1H).[b] | 1.26 |

TABLE 1-continued

| Ex. No. | Structure | Name | MS (ESI) (M + H) | ¹H NMR | LC RT[a] (min) and chiral conditions when separated |
|---|---|---|---|---|---|
| 31 | 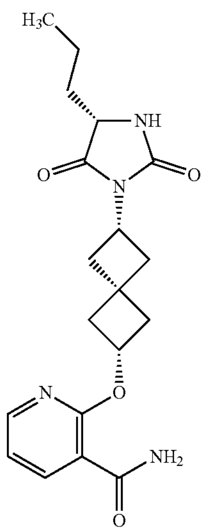 | 2-{[(αR)-6-[(4S)-2,5-dioxo-4-propylimidazolidin-1-yl]spiro[3.3]heptan-2-yl]oxy}pyridine-3-carboxamide | 373.1 | 1H NMR (500 MHz, DMSO-d6) δ 8.35-8.09 (m, 2H), 7.76-7.52 (m, 2H), 7.19-7.02 (m, 1H), 5.31-5.12 (m, 1H), 4.33 (br t, J = 8.5 Hz, 1H), 4.04-3.93 (m, 1H), 3.63-3.24 (m, 3H), 2.84 (q, J = 10.6 Hz, 1H), 2.73-2.61 (m, 1H), 2.35-2.14 (m, 3H), 1.73-1.57 (m, 1H), 1.54-1.40 (m, 1H), 1.38-1.20 (m, 2H), 0.88 (br t, J = 7.3 Hz, 3H) | 1.29 |
| 32 | 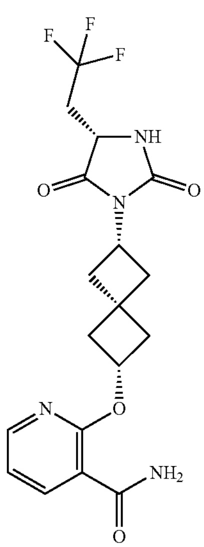 | 2-{[(αR)-6-[(4S)-2,5-dioxo-4-(2,2,2-trifluoroethyl)imidazolidin-1-yl]spiro[3.3]heptan-2-yl]oxy}pyridine-3-carboxamide | 413.2 | 1H NMR (500 MHz, DMSO-d6) δ 8.27 (dd, J = 4.8, 1.9 Hz, 1H), 8.18 (dd, J = 7.4, 1.8 Hz, 1H), 8.05 (s, 1H), 7.53 (br s, 2H), 7.10 (dd, J = 7.4, 4.8 Hz, 1H), 5.25 (quin, J = 7.0 Hz, 1H), 4.35 (quin, J = 8.8 Hz, 1H), 4.03 (br d, J = 1.6 Hz, 1H), 2.85 (q, J = 9.6 Hz, 2H), 2.69 (dt, J = 11.7, 5.8 Hz, 1H), 2.40-2.17 (m, 4H), 1.58 (br d, J = 4.3 Hz, 1H), 1.47-1.28 (m, 2H), 1.27-1.12 (m, 2H), 0.98-0.73 (m, 6H)[b] | 1.39 |

TABLE 1-continued

| Ex. No. | Structure | Name | MS (ESI) (M + H) | ¹H NMR | LC RT[a] (min) and chiral conditions when separated |
|---|---|---|---|---|---|
| 33 | 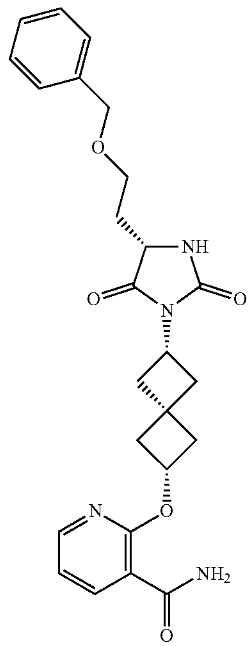 | 2-{[(αR)-6-[(4S)-4-[2-(benzyloxy)ethyl]-2,5-dioxoimidazolidin-1-yl]spiro[3.3]heptan-2-yl]oxy}pyridine-3-carboxamide | 465.2 | 1H NMR (500 MHz, DMSO-d6) δ 8.28 (br d, J = 4.6 Hz, 1H), 8.22-8.12 (m, 2H), 7.77-7.52 (m, 2H), 7.41-7.25 (m, 4H), 7.11 (dd, J = 7.0, 4.9 Hz, 1H), 5.20 (quin, J = 7.0 Hz, 1H), 4.52-4.35 (m, 2H), 4.29 (quin, J = 8.7 Hz, 1H), 4.06 (br t, J = 5.8 Hz, 1H), 2.89-2.74 (m, 2H), 2.71-2.60 (m, 1H), 2.50-2.44 (m, 1H), 2.30-2.17 (m, 3H), 2.15-2.06 (m, 1H), 2.03-1.82 (m, 2H).[b] | 1.50 |
| 34 | 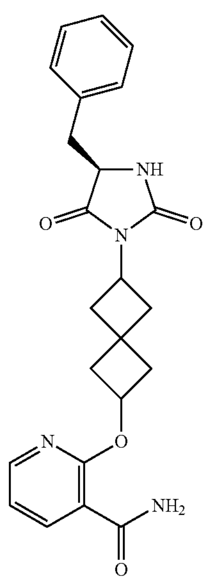 [SMILES: NC(=O)c1cccnc1OC1CC2(C1)CC(N1C(=O)N[C@H](Cc3ccccc3)C1=O)C2] | 2-({6-[(4R)-4-benzyl-2,5-dioxoimidazolidin-1-yl]spiro[3.3]heptan-2-yl}oxy)pyridine-3-carboxamide | 421.1 | 1H NMR (500 MHz, DMSO-d6) δ 8.25 (dd, J = 4.7, 1.7 Hz, 1H), 8.20-8.11 (m, 2H), 7.72-7.54 (m, 2H), 7.32-7.18 (m, 3H), 7.16-7.06 (m, 3H), 5.16 (quin, J = 7.2 Hz, 1H), 4.27 (br t, J = 4.4 Hz, 1H), 4.10 (quin, J = 8.6 Hz, 1H), 2.94 (br d, J = 4.6 Hz, 2H), 2.64-2.54 (m, 3H), 2.43 (dt, J = 11.7, 5.9 Hz, 1H), 2.22-2.08 (m, 3H), 2.03-1.91 (m, 1H) | 1.41 |

TABLE 1-continued

| Ex. No. | Structure | Name | MS (ESI) (M + H) | ¹H NMR | LC RT[a] (min) and chiral conditions when separated |
|---|---|---|---|---|---|
| 35 | 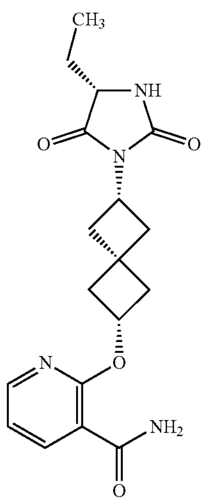 | 2-{[(αR)-6-[(4S)-4-ethyl-2,5-dioxoimidazolidin-1-yl]spiro[3.3]heptan-2-yl]oxy}pyridine-3-carboxamide | 359.0 | 1H NMR (500 MHz, DMSO-d6) δ 8.27 (dd, J = 4.7, 1.7 Hz, 1H), 8.21 (s, 1H), 8.17 (dd, J = 7.5, 1.7 Hz, 1H), 7.77-7.52 (m, 2H), 7.11 (dd, J = 7.5, 5.0 Hz, 1H), 5.22 (quin, J = 7.1 Hz, 1H), 4.33 (quin, J = 8.9 Hz, 1H), 3.94 (br t, J = 5.3 Hz, 1H), 2.84 (q, J = 10.7 Hz, 2H), 2.67 (dt, J = 11.4, 5.8 Hz, 1H), 2.37-2.15 (m, 4H), 1.78-1.64 (m, 1H), 1.55 (dt, J = 14.0, 7.0 Hz, 1H), 0.84 (t, J = 7.3 Hz, 3H). missing 1 H (under DMSO) | 1.14 |
| 36 | 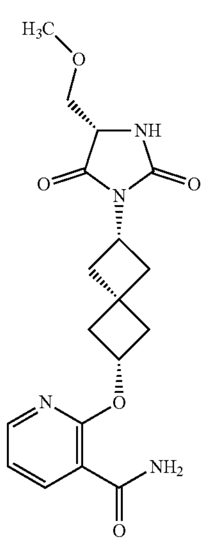 | 2-{[(αR)-6-[(4S)-4-(methoxymethyl)-2,5-dioxoimidazolidin-1-yl]spiro[3.3]heptan-2-yl]oxy}pyridine-3-carboxamide | 375.1 | 1H NMR (500 MHz, DMSO-d6) δ 8.27 (dd, J = 4.9, 1.8 Hz, 1H), 8.21 (s, 1H), 8.17 (dd, J = 7.3, 1.8 Hz, 1H), 7.77-7.52 (m, 2H), 7.11 (dd, J = 7.6, 4.9 Hz, 1H), 5.22 (quin, J = 7.2 Hz, 1H), 4.32 (quin, J = 8.8 Hz, 1H), 4.12 (br s, 1H), 3.58 (dd, J = 10.4, 4.0 Hz, 1H), 3.25 (s, 2H), 2.89-2.76 (m, 2H), 2.67 (dt, J = 11.5, 5.7 Hz, 1H), 2.36-2.13 (m, 4H).[b] | 1.18 |

TABLE 1-continued

| Ex. No. | Structure | Name | MS (ESI) (M + H) | ¹H NMR | LC RT$^a$ (min) and chiral conditions when separated |
|---|---|---|---|---|---|
| 38 | 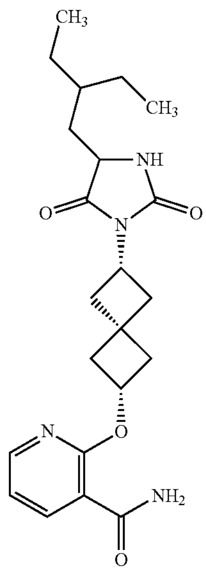 | 2-{[(αR)-6-[4-(2-ethylbutyl)-2,5-dioxoimidazolidin-1-yl]spiro[3.3]heptan-2-yl]oxy}pyridine-3-carboxamide | 415.3 | 1H NMR (500 MHz, DMSO-d6) δ 8.34-8.24 (m, 2H), 8.16 (br d, J = 7.3 Hz, 1H), 7.75-7.53 (m, 2H), 7.11 (dd, J = 7.2, 5.0 Hz, 1H), 5.22 (quin, J = 7.1 Hz, 1H), 4.33 (quin, J = 8.8 Hz, 1H), 3.98 (br d, J = 8.5 Hz, 1H), 2.92-2.75 (m, 2H), 2.67 (dt, J = 11.1, 5.6 Hz, 1H), 2.49-2.43 (m, 1H), 2.36-2.10 (m, 4H), 1.57 (td, J = 8.3, 4.1 Hz, 1H), 1.47-1.15 (m, 6H), 0.89-0.73 (m, 6H). | 1.70 Chiralpak IC, 21x250 mm, 5 mm 65% CO2/35% IPA-CAN 50-50 w/ 0.1% DEA Flow 60 mL/min: $t_R$ = 10.10 min |
| 39 | 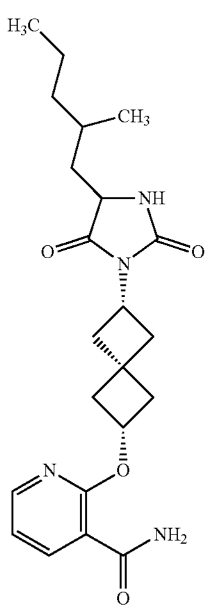 | 2-{[(αR)-6-[4-(2-methylpentyl)-2,5-dioxoimidazolidin-1-yl]spiro[3.3]heptan-2-yl]oxy}pyridine-3-carboxamide | 415.1 | 1H NMR (500 MHz, DMSO-d6) δ 8.33-8.23 (m, 2H), 8.16 (dd, J = 7.3, 1.8 Hz, 1H), 7.75-7.53 (m, 2H), 7.11 (dd, J = 7.5, 5.0 Hz, 1H), 5.22 (quin, J = 7.1 Hz, 1H), 4.33 (quin, J = 8.9 Hz, 1H), 3.99 (br dd, J = 7.8, 5.0 Hz, 1H), 2.83 (q, J = 9.9 Hz, 2H), 2.67 (dt, J = 11.2, 5.8 Hz, 1H), 2.50-2.44 (m, 1H), 2.35-2.12 (m, 4H), 1.74-1.56 (m, 1H), 1.49-1.38 (m, 1H), 1.36-1.18 (m, 4H), 1.17-1.00 (m, 1H), 0.91-0.80 (m, 6H) | 1.72 |

TABLE 1-continued

| Ex. No. | Structure | Name | MS (ESI) (M + H) | ¹H NMR | LC RT[a] (min) and chiral conditions when separated |
|---|---|---|---|---|---|
| 40 | 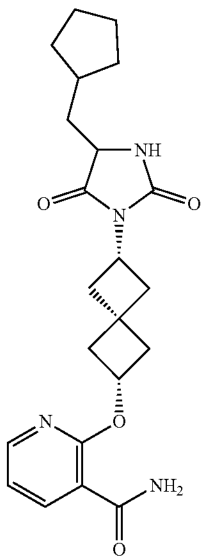 | 2-{[(αR)-6-[4-(cyclopentylmethyl)-2,5-dioxoimidazolidin-1-yl]spiro[3.3]heptan-2-yl]oxy}pyridine-3-carboxamide | 413.3 | 1H NMR (500 MHz, DMSO-d6) Shift 8.26 (dd, J = 4.8, 1.9 Hz, 1H), 8.18 (dd, J = 7.4, 1.9 Hz, 1H), 8.10 (s, 1H), 7.53 (br s, 2H), 7.10 (dd, J = 7.4, 4.9 Hz, 1H), 5.25 (quin, J = 7.1 Hz, 1H), 4.34 (quin, J = 8.8 Hz, 1H), 3.94 (br dd, J = 6.8, 5.2 Hz, 1H), 2.85 (td, J = 10.0, 5.8 Hz, 2H), 2.73-2.61 (m, 1H), 2.54 (br s, 1H), 2.40-2.16 (m, 4H), 1.93 (dt, J = 15.3, 7.7 Hz, 1H), 1.81-1.65 (m, 3H), 1.64-1.41 (m, 5H), 1.18-1.00 (m, 2H) | 1.60 Chiralpak AD, 30x250 mm, 5 mm 65% CO2/35% IPA-ACN 50-50 Flow 100 mL/min: $t_R$ = 15.45 min |
| 41 | 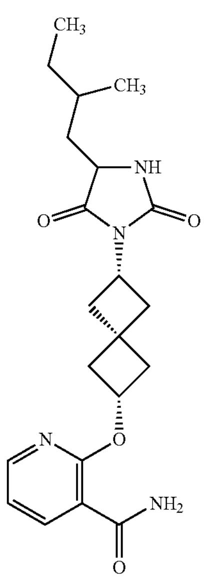 | 2-{[(αR)-6-[4-(2-methylbutyl)-2,5-dioxoimidazolidin-1-yl]spiro[3.3]heptan-2-yl]oxy}pyridine-3-carboxamide | 401.1 | 1H NMR (500 MHz, DMSO-d6) δ 8.26 (dd, J = 4.7, 1.8 Hz, 1H), 8.21-8.08 (m, 2H), 7.53 (br s, 2H), 7.10 (dd, J = 7.4, 4.9 Hz, 1H), 5.25 (quin, J = 6.9 Hz, 1H), 4.34 (quin, J = 8.6 Hz, 1H), 4.03-3.91 (m, 1H), 2.85 (q, J = 9.2 Hz, 2H), 2.68 (dt, J = 11.5, 5.8 Hz, 1H), 2.38-2.15 (m, 4H), 1.74-1.05 (m, 5H), 0.95-0.78 (m, 6H).[b] | 1.56 |

TABLE 1-continued

| Ex. No. | Structure | Name | MS (ESI) (M + H) | ¹H NMR | LC RT[a] (min) and chiral conditions when separated |
|---|---|---|---|---|---|
| 42 | 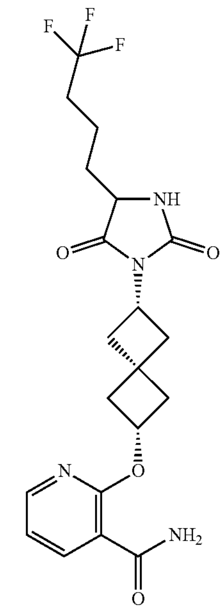 | 2-{[(αR)-6-[2,5-dioxo-4-(4,4,4-trifluorobutyl)imidazolidin-1-yl]spiro[3.3]heptan-2-yl]oxy}pyridine-3-carboxamide | 441.1 | 1H NMR (500 MHz, DMSO-d6) δ 8.34-8.22 (m, 2H), 8.16 (dd, J = 7.3, 1.8 Hz, 1H), 7.78-7.53 (m, 2H), 7.11 (dd, J = 7.6, 4.9 Hz, 1H), 5.22 (quin, J = 7.2 Hz, 1H), 4.33 (quin, J = 8.9 Hz, 1H), 4.08-3.95 (m, 1H), 2.83 (q, J = 10.2 Hz, 2H), 2.67 (dt, J = 11.2, 5.8 Hz, 1H), 2.50-2.46 (m, 1H), 2.36-2.13 (m, 6H), 1.89-1.69 (m, 1H), 1.65-1.46 (m, 3H) | 1.49 Chiralpak AD, 30x250 mm, 5 mm 75% CO2/25% methanol w/ 0.1% DEA Flow 100 mL/min: t$_R$ = 6.97 min |
| 43 | 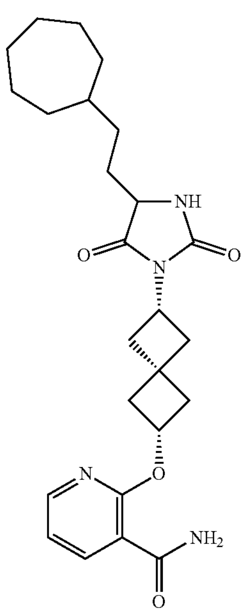 | 2-{[(αR)-6-[4-(2-cycloheptylethyl)-2,5-dioxoimidazolidin-1-yl]spiro[3.3]heptan-2-yl]oxy}pyridine-3-carboxamide | 455.3 | 1H NMR (500 MHz, DMSO-d6) δ 8.26 (dd, J = 4.8, 1.8 Hz, 1H), 8.18 (dd, J = 7.4, 1.8 Hz, 1H), 8.08 (s, 1H), 7.53 (br s, 2H), 7.10 (dd, J = 7.4, 4.9 Hz, 1H), 5.25 (quin, J = 7.0 Hz, 1H), 4.33 (quin, J = 8.7 Hz, 1H), 3.94 (br t, J = 5.6 Hz, 1H), 2.92-2.78 (m, 2H), 2.68 (dt, J = 11.5, 5.8 Hz, 1H), 2.41-2.16 (m, 4H), 1.84-1.64 (m, 4H), 1.63-1.43 (m, 5H), 1.40-1.23 (m, 6H), 1.06 (br s, 2H).[b] | 2.07 Chiralpak AD, 30x250 mm, 5 mm 75% CO2/25% IPA w/ 0.1% DEA Flow 100 mL/min: t$_R$ = 15.19 min |

TABLE 1-continued

| Ex. No. | Structure | Name | MS (ESI) (M + H) | ¹H NMR | LC RT$^a$ (min) and chiral conditions when separated |
|---|---|---|---|---|---|
| 44 | 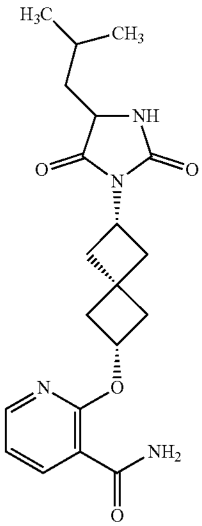 | 2-{[(αR)-6-[4-(2-methylpropyl)-2,5-dioxoimidazolidin-1-yl]spiro[3.3]heptan-2-yl]oxy}pyridine-3-carboxamide | 387.1 | 1H NMR (500 MHz, DMSO-d6) Shift 8.35-8.23 (m, 2H), 8.17 (dd, J = 7.3, 1.5 Hz, 1H), 7.76-7.50 (m, 2H), 7.11 (dd, J = 7.3, 5.2 Hz, 1H), 5.23 (quin, J = 7.2 Hz, 1H), 4.34 (quin, J = 8.9 Hz, 1H), 3.99 (br dd, J = 8.9, 4.0 Hz, 1H), 2.84 (q, J = 9.7 Hz, 2H), 2.71-2.64 (m, 1H), 2.48 (br s, 1H), 2.36-2.13 (m, 4H), 1.77 (dt, J = 13.8, 6.7 Hz, 1H), 1.51 (ddd, J = 13.4, 9.0, 4.1 Hz, 1H), 1.38 (ddd, J = 13.9, 8.9, 5.3 Hz, 1H), 0.88 (d, J = 6.4 Hz, 6H) | 1.47 |
| 45 | 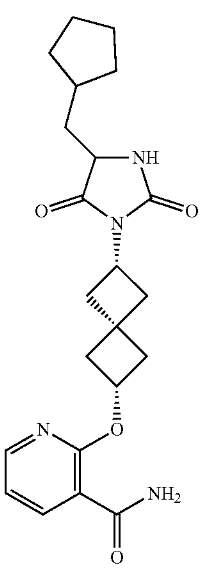 | 2-{[(αR)-6-[4-(cyclopentylmethyl)-2,5-dioxoimidazolidin-1-yl]spiro[3.3]heptan-2-yl]oxy}pyridine-3-carboxamide | 413.3 | 1H NMR (500 MHz, DMSO-d6) δ 8.27 (dd, J = 5.5, 3.7 Hz, 2H), 8.19-8.13 (m, 1H), 7.74-7.53 (m, 2H), 7.11 (dd, J = 7.3, 4.9 Hz, 1H), 5.22 (quin, J = 7.1 Hz, 1H), 4.33 (quin, J = 8.8 Hz, 1H), 3.96 (br dd, J = 7.3, 4.6 Hz, 1H), 2.92-2.79 (m, 2H), 2.67 (br dd, J = 11.1, 5.6 Hz, 1H), 2.50-2.47 (m, 1H), 2.36-2.14 (m, 4H), 1.91 (dt, J = 15.4, 7.9 Hz, 1H), 1.80-1.63 (m, 3H), 1.61-1.41 (m, 5H), 1.16-0.99 (m, 2H) | 1.62 |

TABLE 1-continued

| Ex. No. | Structure | Name | MS (ESI) (M + H) | ¹H NMR | LC RT[a] (min) and chiral conditions when separated |
|---|---|---|---|---|---|
| 46 | 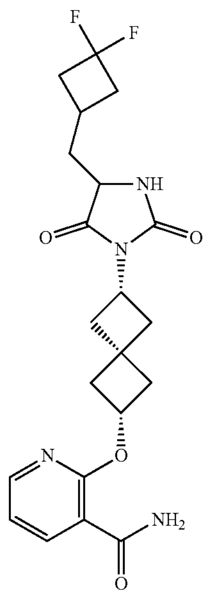 | 2-{[(αR)-6-{4-[(3,3-difluorocyclobutyl)methyl]-2,5-dioxoimidazolidin-1-yl}spiro[3.3]heptan-2-yl]oxy}pyridine-3-carboxamide | 435.1 | 1H NMR (500 MHz, DMSO-d6) δ 8.27 (dd, J = 4.7, 1.7 Hz, 1H), 8.22 (s, 1H), 8.16 (dd, J = 7.5, 1.7 Hz, 1H), 7.75-7.50 (m, 2H), 7.11 (dd, J = 7.6, 4.9 Hz, 1H), 5.22 (quin, J = 7.1 Hz, 1H), 4.33 (quin, J = 8.9 Hz, 1H), 3.98 (br t, J = 5.8 Hz, 1H), 2.83 (td, J = 10.1, 4.6 Hz, 2H), 2.74-2.58 (m, 3H), 2.48 (br s, 1H), 2.38-2.13 (m, 6H), 1.88 (dt, J = 12.9, 6.5 Hz, 1H), 1.76 (dt, J = 13.7, 6.9 Hz, 1H).[b] | 1.43 |
| 47 | 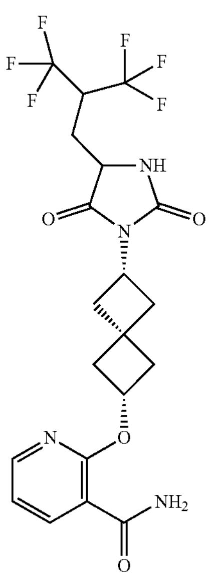 | 2-{[(αR)-6-{4-[(3,3,3,3',3',3'-hexafluoroisobutyl]-2,5-dioxoimidazolidin-1-yl}spiro[3.3]heptan-2-yl]oxy}pyridine-3-carboxamide | 495.1 | 1H NMR (500 MHz, DMSO-d6) δ 8.34-8.21 (m, 2H), 8.17 (br d, J = 7.3 Hz, 1H), 7.79-7.52 (m, 2H), 7.12 (dd, J = 7.3, 4.9 Hz, 1H), 5.23 (quin, J = 7.1 Hz, 1H), 4.33 (quin, J = 8.8 Hz, 1H), 4.21-4.11 (m, 1H), 4.02 (br d, J = 2.7 Hz, 1H), 2.94 (q, J = 7.3 Hz, 1H), 2.88-2.77 (m, 2H), 2.68 (br dd, J = 11.4, 6.6 Hz, 1H), 2.50-2.44 (m, 1H), 2.33 (br s, 1H), 2.29-2.16 (m, 3H), 2.15-2.04 (m, 1H) | 1.65 |

TABLE 1-continued

| Ex. No. | Structure | Name | MS (ESI) (M + H) | ¹H NMR | LC RT[a] (min) and chiral conditions when separated |
|---|---|---|---|---|---|
| 48 | 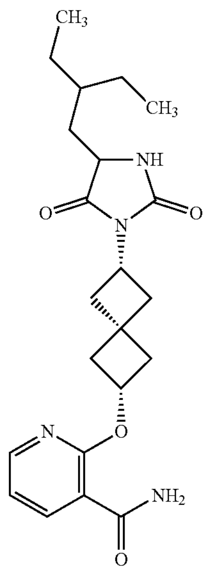 | 2-{[(αR)-6-[4-(2-ethylbutyl)-2,5-dioxoimidazolidin-1-yl]spiro[3.3]heptan-2-yl]oxy}pyridine-3-carboxamide | 415.1 | 1H NMR (500 MHz, DMSO-d6) δ 8.33-8.22 (m, 2H), 8.19-8.09 (m, 1H), 7.75-7.51 (m, 2H), 7.11 (dd, J = 7.3, 4.9 Hz, 1H), 5.22 (quin, J = 7.0 Hz, 1H), 4.33 (quin, J = 8.9 Hz, 1H), 4.03-3.92 (m, 1H), 2.84 (q, J = 10.4 Hz, 2H), 2.67 (dt, J = 11.1, 5.7 Hz, 1H), 2.50-2.42 (m, 1H), 2.35-2.12 (m, 4H), 1.66-1.52 (m, 1H), 1.48-1.13 (m, 6H), 0.90-0.70 (m, 6H) | 1.69 Chiralpak IC, 21x250 mm, 5 mm 65% CO2/35% IPA-CAN 50-50 w/ 0.1% DEA Flow 60 mL/min: $t_R$ = 12.54 min |
| 49 | 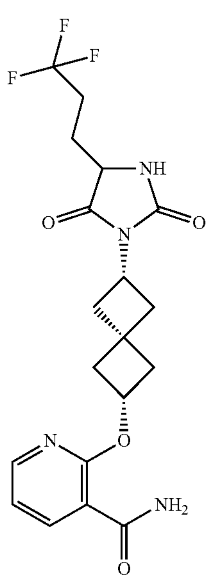 | 2-{[(αR)-6-[2,5-dioxo-4-(3,3,3-trifluoropropyl)imidazolidin-1-yl]spiro[3.3]heptan-2-yl]oxy}pyridine-3-carboxamide | 427.0 | 1H NMR (500 MHz, DMSO-d6) δ 8.34-8.23 (m, 2H), 8.17 (br d, J = 7.3 Hz, 1H), 7.75-7.52 (m, 2H), 7.11 (dd, J = 7.2, 5.0 Hz, 1H), 5.23 (quin, J = 7.1 Hz, 1H), 4.33 (quin, J = 8.8 Hz, 1H), 4.07 (br t, J = 6.4 Hz, 1H), 2.90-2.79 (m, 2H), 2.74-2.62 (m, 1H), 2.46-2.37 (m, 1H), 2.36-2.28 (m, 2H), 2.28-2.16 (m, 3H), 1.97-1.86 (m, 1H), 1.81-1.67 (m, 1H)[b] | 1.37 |

TABLE 1-continued

| Ex. No. | Structure | Name | MS (ESI) (M + H) | ¹H NMR | LC RT[a] (min) and chiral conditions when separated |
|---|---|---|---|---|---|
| 50 | 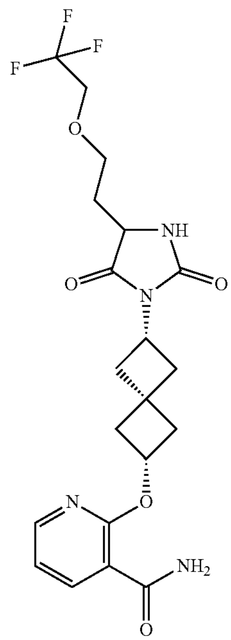 | 2-{[(αR)-6-{2,5-dioxo-4-[2-(2,2,2-trifluoroethoxy)ethyl]imidazolidin-1-yl}spiro[3.3]heptan-2-yl]oxy}pyridine-3-carboxamide | 457.2 | 1H NMR (500 MHz, DMSO-d6) δ 8.26 (dd, J = 4.8, 1.8 Hz, 1H), 8.18 (dd, J = 7.4, 1.9 Hz, 1H), 8.07 (s, 1H), 7.53 (br s, 2H), 7.10 (dd, J = 7.4, 4.9 Hz, 1H), 5.25 (quin, J = 7.0 Hz, 1H), 4.33 (quin, J = 8.7 Hz, 1H), 4.10-3.93 (m, 3H), 3.81-3.60 (m, 2H), 2.85 (q, J = 9.6 Hz, 2H), 2.68 (dt, J = 11.6, 5.8 Hz, 1H), 2.36-2.15 (m, 4H), 2.02-1.92 (m, 1H), 1.91-1.80 (m, 1H).[b] | 1.36 Chiralpak AD, 30x250 mm, 5 mm 80% CO2/20% IPA w/0.1% DEA Flow 100 mL/min: t_R = 8.34 min |
| 51 | 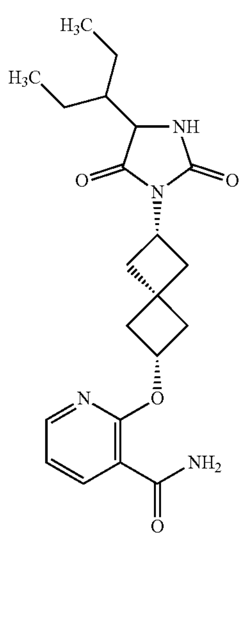 | 2-{[(αR)-6-[2,5-dioxo-4-(pentan-3-yl)imidazolidin-1-yl]spiro[3.3]heptan-2-yl]oxy}pyridine-3-carboxamide | 401.3 | 1H NMR (500 MHz, DMSO-d6) δ 8.27 (dd, J = 4.8, 1.9 Hz, 1H), 8.18 (dd, J = 7.4, 1.8 Hz, 1H), 8.05 (s, 1H), 7.53 (br s, 2H), 7.10 (dd, J = 7.4, 4.8 Hz, 1H), 5.25 (quin, J = 7.0 Hz, 1H), 4.35 (quin, J = 8.8 Hz, 1H), 4.03 (br d, J = 1.6 Hz, 1H), 2.85 (q, J = 9.6 Hz, 2H), 2.69 (dt, J = 11.7, 5.8 Hz, 1H), 2.40-2.17 (m, 4H), 1.58 (br d, J = 4.3 Hz, 1H), 1.47-1.28 (m, 2H), 1.27-1.12 (m, 2H), 0.98-0.73 (m, 6H)[b] | 1.53 |

TABLE 1-continued

| Ex. No. | Structure | Name | MS (ESI) (M + H) | ¹H NMR | LC RT[a] (min) and chiral conditions when separated |
|---|---|---|---|---|---|
| 52 | 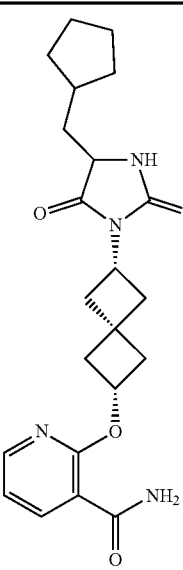 | 2-{[((R)-6-[4-(cyclopentylmethyl)-2,5-dioxoimidazolidin-1-yl]spiro[3.3]heptan-2-yl]oxy}pyridine-3-carboxamide | 413.2 | 1H NMR (500 MHz, DMSO-d6) δ 8.27 (dd, J = 4.8, 1.9 Hz, 1H), 8.18 (dd, J = 7.4, 1.9 Hz, 1H), 8.10 (s, 1H), 7.53 (br s, 2H), 7.10 (dd, J = 7.5, 4.9 Hz, 1H), 5.25 (quin, J = 7.1 Hz, 1H), 4.34 (quin, J = 8.8 Hz, 1H), 3.94 (br dd, J = 6.7, 5.1 Hz, 1H), 2.85 (td, J = 9.9, 6.1 Hz, 2H), 2.74-2.64 (m, 1H), 2.41-2.29 (m, 1H), 2.29-2.17 (m, 3H), 2.01-1.87 (m, 1H), 1.81-1.65 (m, 3H), 1.63-1.42 (m, 5H), 1.17-0.99 (m, 2H).[b] | 1.59 Chiralpak AD, 30x250 mm, 5 mm 65% CO2/35% IPA-ACN 50-50 Flow 100 mL/min: $t_R$ = 12.96 min |
| 53 | 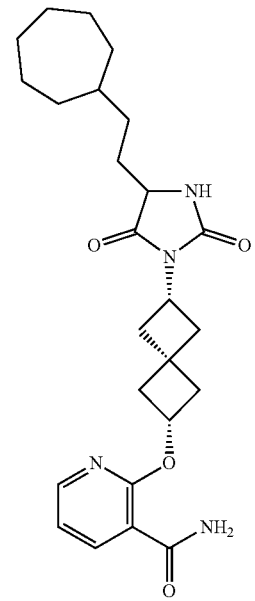 | 2-{[(αR)-6-[4-(2-cycloheptylethyl)-2,5-dioxoimidazolidin-1-yl]spiro[3.3]heptan-2-yl]oxy}pyridine-3-carboxamide | 455.2 | 1H NMR (500 MHz, DMSO-d6) δ 8.26 (dd, J = 4.8, 1.9 Hz, 1H), 8.18 (dd, J = 7.4, 1.9 Hz, 1H), 8.08 (s, 1H), 7.53 (br s, 2H), 7.10 (dd, J = 7.4, 4.9 Hz, 1H), 5.25 (quin, J = 7.0 Hz, 1H), 4.33 (quin, J = 8.7 Hz, 1H), 3.94 (br t, J = 5.6 Hz, 1H), 2.94-2.78 (m, 2H), 2.68 (dt, J = 11.5, 5.8 Hz, 1H), 2.40-2.16 (m, 4H), 1.81-1.63 (m, 4H), 1.62-1.42 (m, 5H), 1.39-1.21 (m, 6H), 1.06 (br s, 2H).[b] | 2.06 Chiralpak AD, 30x250 mm, 5 mm 75% CO2/25% IPA w/ 0.1% DEA Flow 100 mL/min: $t_R$ = 10.34 min |

TABLE 1-continued

| Ex. No. | Structure | Name | MS (ESI) (M + H) | ¹H NMR | LC RT[a] (min) and chiral conditions when separated |
|---|---|---|---|---|---|
| 54 | 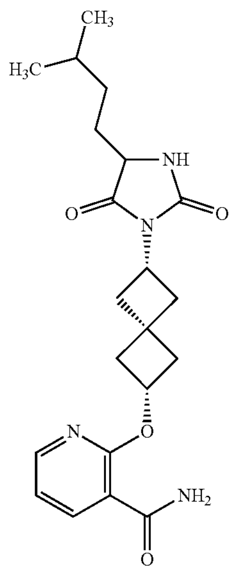 | 2-{[(αR)-6-[4-(3-methylbutyl)-2,5-dioxoimidazolidin-1-yl]spiro[3.3]heptan-2-yl]oxy}pyridine-3-carboxamide | 401.2 | 1H NMR (500 MHz, DMSO-d6) δ 8.27 (dd, J = 4.8, 1.7 Hz, 1H), 8.18 (dd, J = 7.5, 1.7 Hz, 1H), 8.08 (s, 1H), 7.53 (br s, 2H), 7.10 (dd, J = 7.4, 4.9 Hz, 1H), 5.25 (quin, J = 7.0 Hz, 1H), 4.33 (quin, J = 8.8 Hz, 1H), 2.85 (q, J = 11.0 Hz, 2H), 2.68 (dt, J = 11.7, 5.7 Hz, 1H), 2.39-2.16 (m, 5H), 1.77-1.63 (m, 1H), 1.60-1.45 (m, 2H), 1.33-1.08 (m, 3H), 0.87 (dd, J = 6.5, 3.8 Hz, 6H) | 1.67 Chiralpak AD, 30x250 mm, 5 mm 65% CO2/35% IPA-ACN 50-50 w/0.1% DEA Flow 100 mL/min: $t_R$ = 5.29 min |
| 55 | 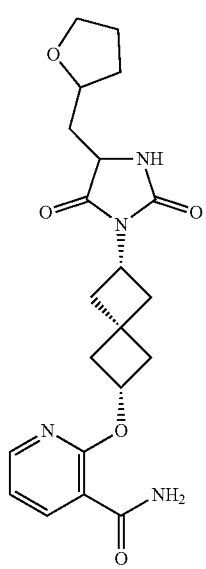 | 2-{[(αR)-6-{2,5-dioxo-4-[(oxolan-2-yl)methyl]imidazolidin-1-yl}spiro[3.3]heptan-2-yl]oxy}pyridine-3-carboxamide | 415.0 | 1H NMR (500 MHz, DMSO-d6) δ 8.46-8.31 (m, 1H), 8.27 (br d, J = 3.1 Hz, 1H), 8.16 (br d, J = 7.3 Hz, 1H), 7.73-7.52 (m, 2H), 7.11 (dd, J = 7.2, 5.0 Hz, 1H), 5.22 (quin, J = 7.1 Hz, 1H), 4.42-4.24 (m, 1H), 4.01 (br d, J = 7.3 Hz, 1H), 3.94-3.84 (m, 1H), 3.75 (q, J = 7.2 Hz, 1H), 3.66-3.57 (m, 1H), 2.89-2.74 (m, 2H), 2.66 (br dd, J = 11.3, 5.5 Hz, 1H), 2.49-2.43 (m, 1H), 2.35-2.13 (m, 4H), 2.01-1.90 (m, 1H), 1.89-1.75 (m, 2H), 1.57 (ddd, J = 13.8, 9.8, 3.8 Hz, 1H), 1.49-1.37 (m, 1H) | 1.23 |

| Ex. No. | Structure | Name | MS (ESI) (M + H) | ¹H NMR | LC RT$^a$ (min) and chiral conditions when separated |
|---|---|---|---|---|---|
| 56 | 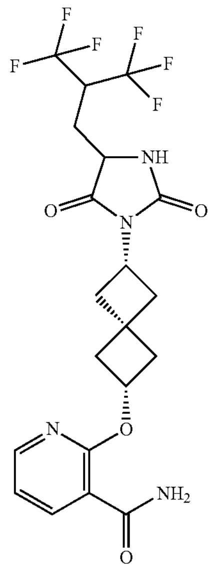 | 2-{[(αR)-6-{2,5-dioxo-4-[3,3,3-trifluoro-2-(trifluoromethyl)propyl]imidazolidin-1-yl}spiro[3.3]heptan-2-yl]oxy}pyridine-3-carboxamide | 495.1 | 1H NMR (500 MHz, DMSO-d6) δ 8.34-8.22 (m, 1H), 8.16 (br d, J = 7.3 Hz, 1H), 7.64 (br s, 2H), 7.11 (dd, J = 7.3, 5.2 Hz, 1H), 5.21 (quin, J = 7.0 Hz, 1H), 4.45-4.24 (m, 2H), 3.98 (s, 1H), 3.84 (br d, J = 5.8 Hz, 1H), 3.68 (br s, 1H), 2.81 (br t, J = 10.2 Hz, 2H), 2.67 (dt, J = 11.3, 5.3 Hz, 1H), 2.51-2.45 (m, 1H), 2.35-2.28 (m, 1H), 2.27-2.15 (m, 3H) | 1.67 |
| 57 | 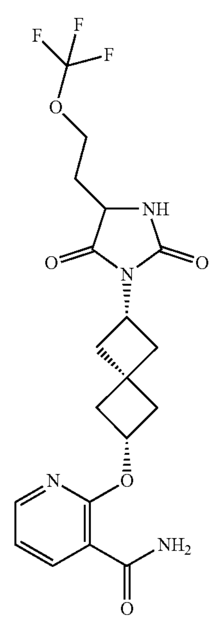 | 2-{[(αR)-6-{2,5-dioxo-4-[2-(trifluoromethoxy)ethyl]imidazolidin-1-yl}spiro[3.3]heptan-2-yl]oxy}pyridine-3-carboxamide | 443.2 | 1H NMR (500 MHz, DMSO-d6) δ 8.28 (br s, 2H), 8.17 (dd, J = 7.5, 1.7 Hz, 1H), 7.77-7.52 (m, 2H), 7.11 (dd, J = 7.3, 4.9 Hz, 1H), 5.23 (quin, J = 7.1 Hz, 1H), 4.33 (quin, J = 8.8 Hz, 1H), 4.24-4.14 (m, 2H), 4.10 (br t, J = 5.6 Hz, 1H), 2.91-2.79 (m, 2H), 2.73-2.62 (m, 1H), 2.51-2.46 (m, 1H), 2.36-2.14 (m, 4H), 2.13-1.97 (m, 2H) | 1.35 Chiralpak AD, 30x250 mm, 5 mm 60% CO2/40% methanol w/0.1% DEA Flow 100 mL/min: $t_R$ = 5.97 min |

TABLE 1-continued

| Ex. No. | Structure | Name | MS (ESI) (M + H) | ¹H NMR | LC RT[a] (min) and chiral conditions when separated |
|---|---|---|---|---|---|
| 58 | 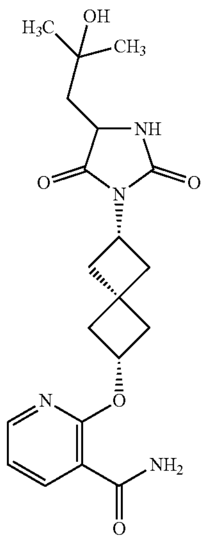 | 2-{[(αR)-6-[4-(2-hydroxy-2-methylpropyl)-2,5-dioxoimidazolidin-1-yl]spiro[3.3]heptan-2-yl]oxy}pyridine-3-carboxamide | 403.3 | 1H NMR (500 MHz, DMSO-d6) δ 8.26 (dd, J = 4.7, 1.6 Hz, 1H), 8.18 (dd, J = 7.4, 1.6 Hz, 1H), 7.53 (br s, 2H), 7.10 (dd, J = 7.4, 4.9 Hz, 1H), 5.25 (quin, J = 7.1 Hz, 1H), 4.35 (quin, J = 8.7 Hz, 1H), 4.07 (dd, J = 9.3, 2.4 Hz, 1H), 2.85 (q, J = 9.6 Hz, 2H), 2.75-2.63 (m, 1H), 2.40-2.30 (m, 1H), 2.28-2.16 (m, 3H), 1.90 (dd, J = 14.1, 2.2 Hz, 1H), 1.53 (dd, J = 14.1, 9.3 Hz, 1H), 1.17 (s, 6H).[b] | 1.06 |
| 59 | 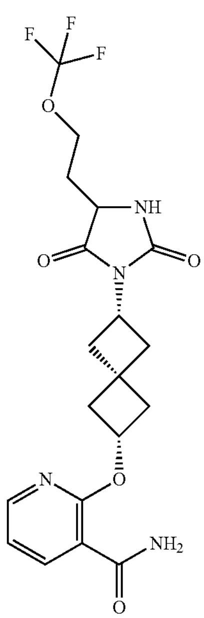 | 2-{[(αR)-6-{2,5-dioxo-4-[2-(trifluoromethoxy)ethyl]imidazolidin-1-yl}spiro[3.3]heptan-2-yl]oxy}pyridine-3-carboxamide | 443.1 | 1H NMR (500 MHz, DMSO-d6) δ 8.28 (br s, 2H), 8.17 (dd, J = 7.5, 1.7 Hz, 1H), 7.75-7.52 (m, 2H), 7.11 (dd, J = 7.5, 5.0 Hz, 1H), 5.23 (quin, J = 7.1 Hz, 1H), 4.33 (quin, J = 8.8 Hz, 1H), 4.26-4.14 (m, 2H), 4.10 (br t, J = 5.6 Hz, 1H), 2.91-2.79 (m, 2H), 2.68 (dt, J = 11.3, 5.6 Hz, 1H), 2.50-2.44 (m, 1H), 2.35-2.15 (m, 4H), 2.13-1.93 (m, 2H) | 1.36 Chiralpak AD, 30x250 mm, 5 mm 60% CO2/40% methanol w/0.1% DEA Flow 100 mL/min: $t_R$ = 3.04 min |

TABLE 1-continued

| Ex. No. | Structure | Name | MS (ESI) (M + H) | ¹H NMR | LC RT[a] (min) and chiral conditions when separated |
|---|---|---|---|---|---|
| 60 | 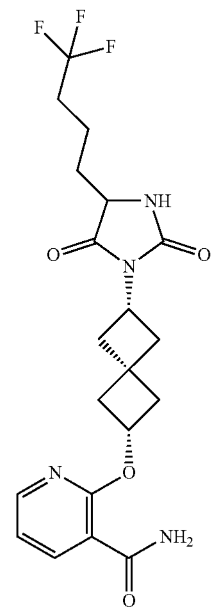 | 2-{[(αR)-6-[2,5-dioxo-4-(4,4,4-trifluorobutyl)imidazolidin-1-yl]spiro[3.3]heptan-2-yl]oxy}pyridine-3-carboxamide | 441.3 | 1H NMR (500 MHz, DMSO-d6) δ 8.36-8.23 (m, 2H), 8.17 (dd, J = 7.6, 1.8 Hz, 1H), 7.77-7.52 (m, 2H), 7.11 (dd, J = 7.3, 4.9 Hz, 1H), 5.22 (quin, J = 7.1 Hz, 1H), 4.34 (quin, J = 8.8 Hz, 1H), 4.08-3.97 (m, 1H), 2.90-2.77 (m, 2H), 2.72-2.63 (m, 1H), 2.50-2.45 (m, 1H), 2.38-2.15 (m, 6H), 1.88-1.71 (m, 1H), 1.65-1.48 (m, 3H) | 1.48 Chiralpak AD, 30x250 mm, 5 mm 75% CO2/25% methanol w/ 0.1% DEA Flow 100 mL/min: $t_R$ = 12.97 min |
| 61 | 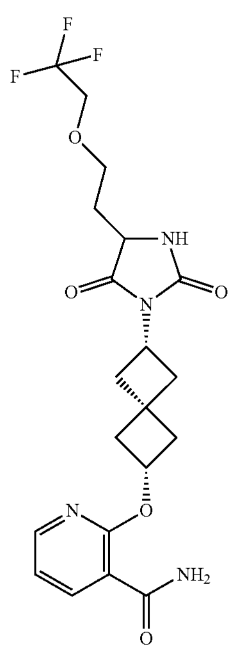 | 2-{[(αR)-6-{2,5-dioxo-4-[2-(2,2,2-trifluoroethoxy)ethyl]imidazolidin-1-yl}spiro[3.3]heptan-2-yl]oxy}pyridine-3-carboxamide | 457.0 | 1H NMR (500 MHz, DMSO-d6) δ 8.26 (dd, J = 4.8, 1.9 Hz, 1H), 8.18 (dd, J = 7.5, 1.9 Hz, 1H), 8.07 (s, 1H), 7.53 (br s, 2H), 7.10 (dd, J = 7.4, 4.9 Hz, 1H), 5.25 (quin, J = 7.1 Hz, 1H), 4.32 (quin, J = 8.8 Hz, 1H), 4.10-3.91 (m, 3H), 3.74 (dt, J = 10.0, 6.4 Hz, 1H), 3.70-3.62 (m, 1H), 2.90-2.78 (m, 2H), 2.68 (dt, J = 11.5, 5.8 Hz, 1H), 2.37-2.15 (m, 4H), 2.02-1.92 (m, 1H), 1.91-1.80 (m, 1H)[b] | 1.36 Chiralpak AD, 30x250 mm, 5 mm 80% CO2/20% IPA w/0.1% DEA Flow 100 mL/min: $t_R$ = 12.31 min |

TABLE 1-continued

| Ex. No. | Structure | Name | MS (ESI) (M + H) | ¹H NMR | LC RT[a] (min) and chiral conditions when separated |
|---|---|---|---|---|---|
| 62 | 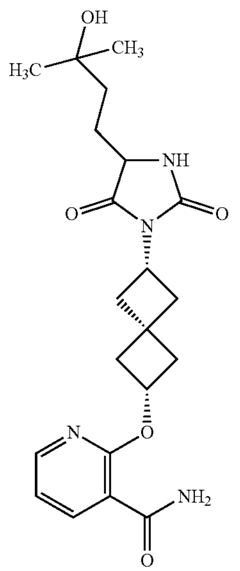 | 2-{[(αR)-6-[4-(3-hydroxy-3-methylbutyl)-2,5-dioxoimidazolidin-1-yl]spiro[3.3]heptan-2-yl]oxy}pyridine-3-carboxamide | 417.3 | 1H NMR (500 MHz, DMSO-d6) δ 8.27 (dd, J = 4.8, 1.7 Hz, 1H), 8.18 (dd, J = 7.4, 1.8 Hz, 1H), 8.08 (s, 1H), 7.55 (br s, 2H), 7.10 (dd, J = 7.4, 4.9 Hz, 1H), 5.25 (quin, J = 7.0 Hz, 1H), 4.34 (quin, J = 8.7 Hz, 1H), 3.94 (br t, J = 5.6 Hz, 1H), 2.94-2.76 (m, 2H), 2.69 (dt, J = 11.4, 5.8 Hz, 1H), 2.43-2.18 (m, 4H), 1.83-1.69 (m, 1H), 1.62-1.51 (m, 1H), 1.46-1.22 (m, 2H), 1.08 (s, 6H)[b] | 1.09 |
| 63 | 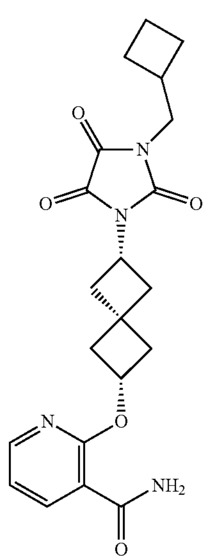 | 2-{[(αR)-6-[3-(cyclobutylmethyl)-2,4,5-trioxoimidazolidin-1-yl]spiro[3.3]heptan-2-yl]oxy}pyridine-3-carboxamide | 413.0 | 1H NMR (500 MHz, DMSO-d6) δ 8.34-8.23 (m, 1H), 8.17 (dd, J = 7.3, 1.5 Hz, 1H), 7.77-7.52 (m, 2H), 7.12 (dd, J = 7.3, 4.9 Hz, 1H), 5.23 (quin, J = 7.1 Hz, 1H), 4.42 (quin, J = 8.6 Hz, 1H), 3.48 (br d, J = 7.0 Hz, 1H), 2.85-2.75 (m, 2H), 2.70 (dt, J = 11.2, 5.8 Hz, 1H), 2.46-2.38 (m, 1H), 2.36-2.22 (m, 3H), 2.03-1.90 (m, 2H), 1.86-1.67 (m, 4H)[b] | 1.81 |

TABLE 1-continued

| Ex. No. | Structure | Name | MS (ESI) (M + H) | ¹H NMR | LC RT[a] (min) and chiral conditions when separated |
|---|---|---|---|---|---|
| 64 | 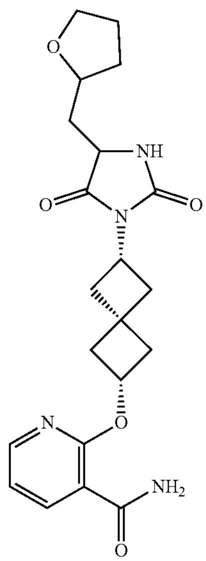 | 2-{[(αR)-6-{2,5-dioxo-4-[(oxolan-2-yl)methyl]imidazolidin-1-yl}spiro[3.3]heptan-2-yl]oxy}pyridine-3-carboxamide | 415.0 | 1H NMR (500 MHz, DMSO-d6) δ 8.27 (dd, J = 4.9, 1.8 Hz, 1H), 8.16 (dd, J = 7.3, 1.5 Hz, 1H), 8.04 (s, 1H), 7.76-7.54 (m, 2H), 7.11 (dd, J = 7.3, 4.9 Hz, 1H), 5.22 (quin, J = 7.2 Hz, 1H), 4.31 (quin, J = 8.9 Hz, 1H), 4.05-3.91 (m, 2H), 3.72-3.61 (m, 1H), 3.59-3.47 (m, 1H), 2.90-2.77 (m, 2H), 2.71-2.60 (m, 1H), 2.47 (br s, 1H), 2.36-2.11 (m, 3H), 1.99-1.88 (m, 1H), 1.87-1.70 (m, 3H), 1.50-1.36 (m, 1H) | 1.21 |
| 65 | 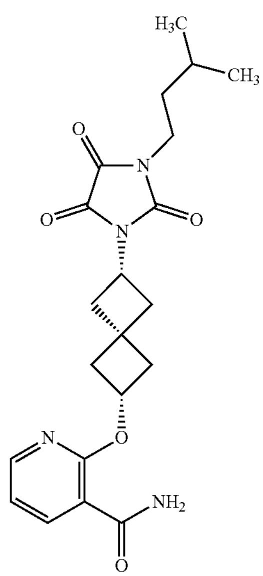 | 2-{[(αR)-6-[3-(3-methylbutyl)-2,4,5-trioxoimidazolidin-1-yl]spiro[3.3]heptan-2-yl]oxy}pyridine-3-carboxamide | 415.1 | 1H NMR (500 MHz, DMSO-d6) δ 8.33-8.24 (m, 1H), 8.17 (dd, J = 7.3, 1.5 Hz, 1H), 7.82-7.52 (m, 2H), 7.12 (dd, J = 7.3, 4.9 Hz, 1H), 5.23 (quin, J = 7.1 Hz, 1H), 4.41 (quin, J = 8.6 Hz, 1H), 2.85-2.74 (m, 2H), 2.72-2.66 (m, 1H), 2.46-2.39 (m, 1H), 2.36-2.22 (m, 3H), 1.86 (s, 1H), 1.59 (dt, J = 13.4, 6.6 Hz, 1H), 1.44 (q, J = 7.0 Hz, 2H), 0.90 (d, J = 6.7 Hz, 5H). | 1.84 |

TABLE 1-continued

| Ex. No. | Structure | Name | MS (ESI) (M + H) | ¹H NMR | LC RT[a] (min) and chiral conditions when separated |
|---|---|---|---|---|---|
| 66 | 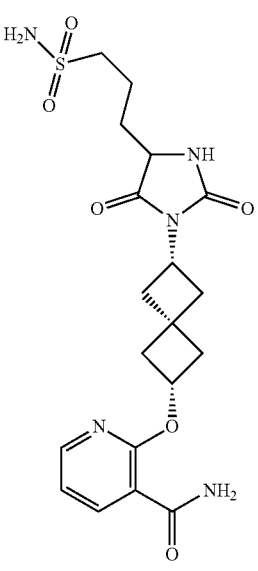 | 2-{[(αR)-6-[2,5-dioxo-4-(3-sulfamoylpropyl)imidazolidin-1-yl]spiro[3.3]heptan-2-yl]oxy}pyridine-3-carboxamide | 452.1 | 1H NMR (500 MHz, DMSO-d6) δ 8.27 (dd, J = 4.7, 1.7 Hz, 1H), 8.18 (dd, J = 7.4, 1.6 Hz, 1H), 8.13 (s, 1H), 7.53 (br s, 2H), 7.10 (dd, J = 7.4, 5.0 Hz, 1H), 6.68 (br s, 1H), 5.25 (quin, J = 7.0 Hz, 1H), 4.34 (quin, J = 8.7 Hz, 1H), 4.01 (br t, J = 5.2 Hz, 1H), 3.00 (br t, J = 7.3 Hz, 2H), 2.85 (q, J = 10.5 Hz, 2H), 2.74-2.64 (m, 1H), 2.37-2.19 (m, 4H), 1.93-1.59 (m, 4H).[b] | 0.89 |
| 67 | 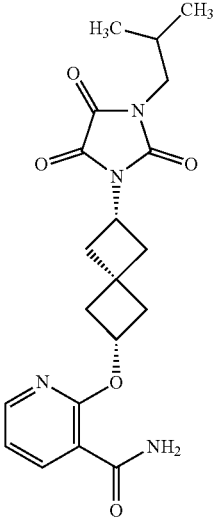 | 2-{[(αR)-6-[3-(2-methylpropyl)-2,4,5-trioxoimidazolidin-1-yl]spiro[3.3]heptan-2-yl]oxy}pyridine-3-carboxamide | 400.9 | 1H NMR (500 MHz, DMSO-d6) δ 8.28 (dd, J = 4.7, 1.7 Hz, 1H), 8.18 (dd, J = 7.5, 1.7 Hz, 1H), 7.82-7.48 (m, 2H), 7.12 (dd, J = 7.3, 4.9 Hz, 1H), 5.24 (quin, J = 7.1 Hz, 1H), 4.42 (quin, J = 8.7 Hz, 1H), 2.87-2.76 (m, 2H), 2.71 (dt, J = 11.4, 5.8 Hz, 1H), 2.47-2.39 (m, 1H), 2.36-2.21 (m, 3H), 1.92 (dt, J = 13.5, 6.8 Hz, 1H), 1.77 (s, 2H), 0.89 (d, J = 6.7 Hz, 6H)[b] | 1.69 |

TABLE 1-continued

| Ex. No. | Structure | Name | MS (ESI) (M + H) | ¹H NMR | LC RT[a] (min) and chiral conditions when separated |
|---|---|---|---|---|---|
| 69 | 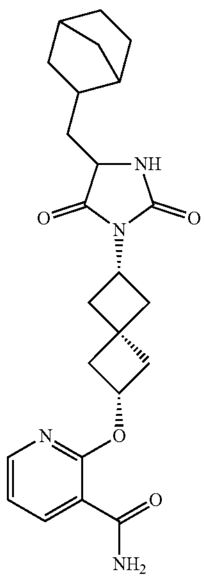 | 2-{[(αR)-6-[4-({bicyclo[2.2.1]heptan-2-yl}methyl)-2,5-dioxoimidazolidin-1-yl]spiro[3.3]heptan-2-yl]oxy}pyridine-3-carboxamide | 439.1 | 1H NMR (500 MHz, DMSO-d6) Shift 8.34-8.21 (m, 2H), 8.16 (dd, J = 7.4, 1.7 Hz, 1H), 7.81-7.53 (m, 2H), 7.11 (dd, J = 7.4, 4.9 Hz, 1H), 5.21 (quin, J = 7.0 Hz, 1H), 4.40-4.26 (m, 1H), 4.05-3.80 (m, 1H), 2.91-2.76 (m, 2H), 2.66 (dt, J = 11.3, 5.7 Hz, 1H), 2.39-2.05 (m, 6H), 1.79-1.61 (m, 1H), 1.60-0.88 (m, 11H) | 1.86 |
| 70 | 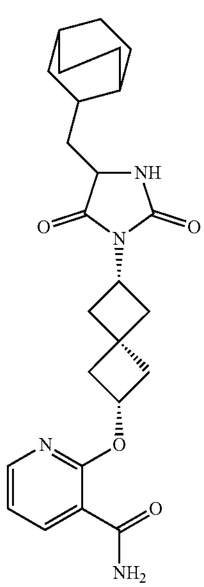 | 2-{[(αR)-6-[4-({bicyclo[2.2.2]octan-2-yl}methyl)-2,5-dioxoimidazolidin-1-yl]spiro[3.3]heptan-2-yl]oxy}pyridine-3-carboxamide | 453.2 | 1H NMR (500 MHz, DMSO-d6) Shift 8.31-8.10 (m, 3H), 7.73-7.54 (m, 2H), 7.10 (dd, J = 7.3, 4.9 Hz, 1H), 5.21 (quin, J = 6.9 Hz, 1H), 4.32 (quin, J = 8.8 Hz, 1H), 4.00-3.92 (m, 1H), 3.42 (s, 1H), 2.83 (q, J = 9.6 Hz, 2H), 2.66 (br dd, J = 11.3, 5.8 Hz, 1H), 2.35-2.11 (m, 4H), 1.86-1.18 (m, 14H), 0.98 (br t, J = 11.6 Hz, 1H) | 1.98 |

TABLE 1-continued

| Ex. No. | Structure | Name | MS (ESI) (M + H) | ¹H NMR | LC RT$^a$ (min) and chiral conditions when separated |
|---|---|---|---|---|---|
| 71 | 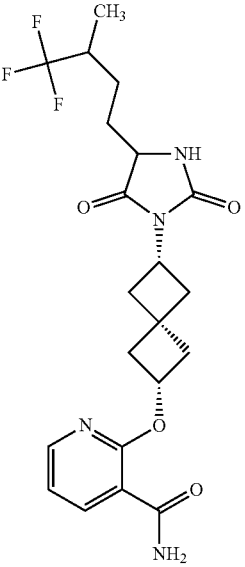 | 2-{[(αR)-6-[2,5-dioxo-4-(4,4,4-trifluoro-3-methylbutyl)imidazolidin-1-yl]spiro[3.3]heptan-2-yl]oxy}pyridine-3-carboxamide | 455.2 | 1H NMR (500 MHz, METHANOL-d4) Shift 8.34 (dd, J = 7.6, 2.1 Hz, 1H), 8.29 (dd, J = 4.8, 2.1 Hz, 1H), 7.11 (dd, J = 7.6, 4.8 Hz, 1H), 5.34 (quin, J = 7.1 Hz, 1H), 4.48 (quin, J = 8.8 Hz, 1H), 4.03 (dt, J = 6.3, 4.8 Hz, 1H), 3.03-2.94 (m, 2H), 2.79 (dt, J = 11.6, 5.9 Hz, 1H), 2.66 (dt, J = 12.1, 6.1 Hz, 1H), 2.45-2.38 (m, 1H), 2.35-2.25 (m, 4H), 2.04-1.61 (m, 3H), 1.52-1.26 (m, 2H), 1.14 (dd, J = 6.9, 3.6 Hz, 3H) | 0.85 |
| 72 | 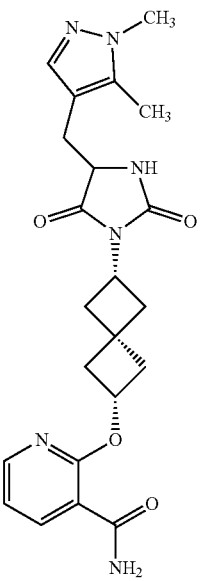 | 2-{[(αR)-6-{4-[(1,5-dimethyl-1H-pyrazol-4-yl)methyl]-2,5-dioxoimidazolidin-1-yl}spiro[3.3]heptan-2-yl]oxy}pyridine-3-carboxamide | 439.0 | 1H NMR (500 MHz, DMSO-d6) Shift 8.27 (br d, J = 3.4 Hz, 1H), 8.20-8.10 (m, 2H), 7.74-7.55 (m, 2H), 7.16-7.02 (m, 2H), 5.20 (br t, J = 7.2 Hz, 1H), 4.24-4.09 (m, 2H), 3.91 (s, 1H), 2.83-2.59 (m, 4H), 2.56 (s, 3H), 2.49-2.42 (m, 1H), 2.26-2.16 (m, 3H), 2.12 (d, J = 1.8 Hz, 3H), 2.09-1.97 (m, 1H) | 1.02 |

| Ex. No. | Structure | Name | MS (ESI) (M + H) | ¹H NMR | LC RT[a] (min) and chiral conditions when separated |
|---|---|---|---|---|---|
| 73 | 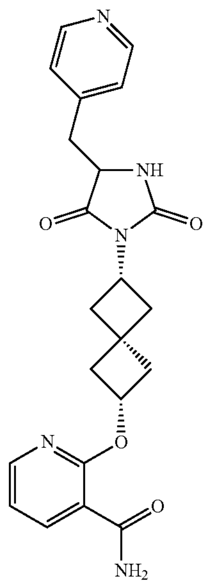 | 2-{[(αR)-6-{2,5-dioxo-4-[(pyridin-4-yl)methyl]imidazolidin-1-yl}spiro[3.3]heptan-2-yl]oxy}pyridine-3-carboxamide | 421.9 | 1H NMR (500 MHz, DMSO-d6) Shift 8.47 (br d, J = 4.6 Hz, 2H), 8.34-8.23 (m, 2H), 8.17 (br d, J = 6.4 Hz, 1H), 7.77-7.53 (m, 2H), 7.19 (br d, J = 4.9 Hz, 2H), 7.11 (dd, J = 7.3, 5.2 Hz, 1H), 5.20 (br t, J = 7.0 Hz, 1H), 4.38 (br t, J = 5.0 Hz, 1H), 4.18 (br t, J = 8.7 Hz, 1H), 3.07-2.92 (m, 2H), 2.70-2.59 (m, 3H), 2.49-2.39 (m, 1H), 2.21 (br dd, J = 10.5, 8.1 Hz, 4H) | 0.81 |
| 75 | 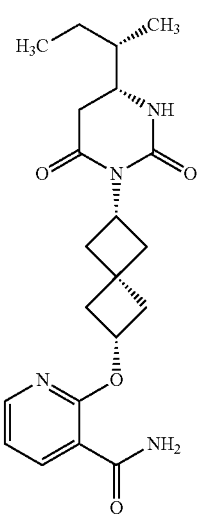 | 2-{[(αR)-6-[(4R)-4-[(2S)-butan-2-yl]-2,6-dioxo-1,3-diazinan-1-yl]spiro[3.3]heptan-2-yl]oxy}pyridine-3-carboxamide | 401.1 | 1H NMR (500 MHz, DMSO-d6) Shift 8.25 (dd, J = 4.7, 1.6 Hz, 1H), 8.17 (dd, J = 7.4, 1.6 Hz, 1H), 7.62-7.44 (m, 3H), 7.10 (dd, J = 7.4, 4.9 Hz, 1H), 5.22 (quin, J = 7.0 Hz, 1H), 4.68 (quin, J = 8.8 Hz, 1H), 3.48 (br d, J = 15.9 Hz, 1H), 3.31 (br d, J = 5.6 Hz, 1H), 2.71 (br t, J = 10.0 Hz, 2H), 2.67-2.59 (m, 1H), 2.46-2.37 (m, 1H), 2.36-2.28 (m, 1H), 2.27-2.13 (m, 3H), 1.56-1.45 (m, 1H), 1.43-1.33 (m, 1H), 1.17-1.03 (m, 1H), 0.85 (t, J = 7.4 Hz, 3H), 0.80 (d, J = 6.7 Hz, 3H) | 1.44 |

TABLE 1-continued

| Ex. No. | Structure | Name | MS (ESI) (M + H) | ¹H NMR | LC RT[a] (min) and chiral conditions when separated |
|---|---|---|---|---|---|
| 76 | 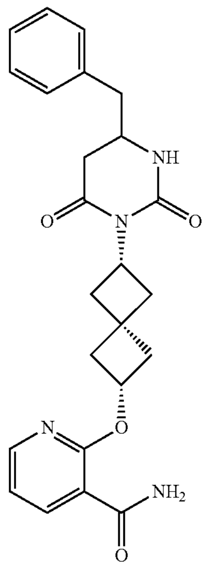 | 2-{[(αR)-6-(4-benzyl-2,6-dioxo-1,3-diazinan-1-yl)spiro[3.3]heptan-2-yl]oxy}pyridine-3-carboxamide | 457.1 | 1H NMR (500 MHz, DMSO-d6) Shift 8.28 (br d, J = 3.4 Hz, 1H), 8.17 (br d, J = 7.3 Hz, 1H), 7.79-7.54 (m, 3H), 7.37-7.05 (m, 6H), 5.22 (br t, J = 6.9 Hz, 1H), 4.75-4.58 (m, 1H), 3.27-3.03 (m, 2H), 2.92 (br d, J = 5.2 Hz, 2H), 2.85-2.76 (m, 1H), 2.73-2.56 (m, 4H), 2.37 (br d, J = 7.9 Hz, 1H), 2.31-2.15 (m, 3H) | 1.59 |
| 77 | 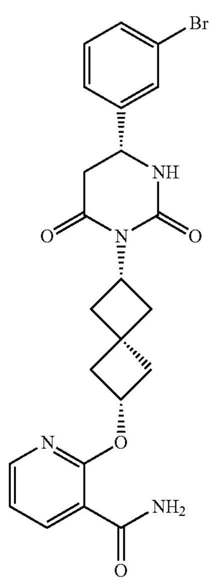 | 2-{[(αR)-6-[(4R)-4-(3-bromophenyl)-2,6-dioxo-1,3-diazinan-1-yl]spiro[3.3]heptan-2-yl]oxy}pyridine-3-carboxamide | 499.0 | 1H NMR (500 MHz, DMSO-d6) Shift 8.26 (br d, J = 2.7 Hz, 2H), 8.21-8.09 (m, 1H), 7.74-7.58 (m, 2H), 7.50 (s, 2H), 7.34 (br d, J = 11.0 Hz, 2H), 7.10 (dd, J = 7.3, 4.9 Hz, 1H), 5.20 (br t, J = 7.2 Hz, 1H), 4.80-4.56 (m, 2H), 2.96 (dd, J = 16.5, 5.5 Hz, 1H), 2.76 (dd, J = 16.5, 6.7 Hz, 1H), 2.73-2.57 (m, 3H), 2.49-2.42 (m, 1H), 2.39-2.28 (m, 1H), 2.27-2.11 (m, 3H) | 1.61 |

TABLE 1-continued

| Ex. No. | Structure | Name | MS (ESI) (M + H) | ¹H NMR | LC RT[a] (min) and chiral conditions when separated |
|---|---|---|---|---|---|
| 78 | 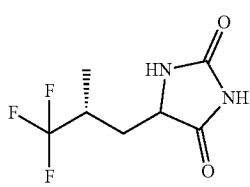 (structure shown in row) | 2-{[(αR)-6-[(4R)-2,6-dioxo-4-(prop-2-en-1-yl)-1,3-diazinan-1-yl]spiro[3.3]heptan-2-yl]oxy}pyridine-3-carboxamide | 385.2 | 1H NMR (500 MHz, DMSO-d6) Shift 8.30-8.24 (m, 1H), 8.16 (dd, J = 7.5, 1.7 Hz, 1H), 7.80-7.53 (m, 3H), 7.10 (dd, J = 7.3, 5.2 Hz, 1H), 5.83-5.67 (m, 1H), 5.20 (t, J = 7.2 Hz, 1H), 5.14-5.04 (m, 2H), 4.67 (br t, J = 8.7 Hz, 1H), 2.92 (s, 1H), 2.80-2.57 (m, 4H), 2.49-2.43 (m, 1H), 2.43-2.29 (m, 2H), 2.29-2.10 (m, 5H) | 1.26 |

[a]All LC retention times are based on Method A unless otherwise specified.
[b]1-3 protons were not accounted for in these samples due to overlap with solvent residue and/or artifacts of water suppression.

Intermediates 92a & 93a. 5-((R)-3,3,3-trifluoro-2-methylpropyl)imidazolidine-2,4-dione and N-1 5-((S)-3,3,3-trifluoro-2-methylpropyl)imidazolidine-2,4-dione

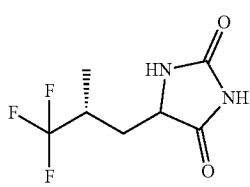

92a

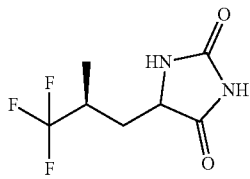

93a

To a 3 necked flask fitted with condenser, nitrogen inlet, and sparge line attached to a bleach scrubber was added 4,4,4-trifluoro-3-methylbutanal (5.0 g, 18 mmol) dissolved in ethanol:water 1:1 (60 mL), ammonium carbonate (8.6 g, 89 mmol) and KCN (2.3 g, 36 mmol). The reaction mixture was heated to 90° C. for 2 hours. The reaction mixture was concentrated under reduced pressure and the residual aqueous was neutralized 7.4 mL of 12 M HCl while taking care to capture evolving gases via bleach scrubber. The precipitate formed was filtered, washed with water, and dried for 12 h on high vacuum to afford 5-(3,3,3-trifluoro-2-methylpropyl)imidazolidine-2,4-dione (3.8 g, 18 mmol, 100% yield) as a mixture of diastereomers.

Diastereomers of 5-(-3,3,3-trifluoro-2-methylpropyl)imidazolidine-2,4-dione were separated via preparative SFC with the following conditions: Column: Chiralpak AD-H, 4.6× 250 mm, 5 micron, 10% MeOH/90% $CO_2$, 2.0 mL/min, 150 Bar. 40° C. to furnish peak 1 (92a): ¹H NMR (500 MHz, CDCl₃) δ 5.31 (br t, J=5.2 Hz, 1H), 4.27-4.14 (m, 1H), 2.58-2.45 (m, 1H), 2.09-1.97 (m, 2H), 1.24 (d, J=6.9 Hz, 3H), $t_R$=4.30 min and peak 3 (93a): ¹H NMR (500 MHz, CDCl₃) δ 5.31 (br s, 1H), 4.26-4.15 (m, 1H), 2.58-2.44 (m, 1H), 2.09-1.99 (m, 2H), 1.24 (d, J=6.9 Hz, 3H) $t_R$=7.57.

Intermediate 92b.
(4R)-2-amino-5,5,5-trifluoro-4-methylpentanoic acid

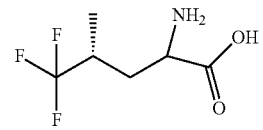

To a microwave vessel containing Intermediate 92a (0.63 g, 3.0 mmol) was added a 2M solution of sodium hydroxide (7.5 mL) and heated to 150° C. in microwave for 30 m. The reaction was neutralized with 1M HCl to obtain a suspension of pH 4-6 material that was filtered, washed, and dried overnight to furnish Intermediate 92b (260 mg, 1.4 mmol, 49% yield) as a mixture of diastereomers: MS (ESI) m/z 186.0 (M+H)⁺, ¹H NMR (500 MHz, CD₃OD) δ 3.61 (br dd, J=8.8, 5.2 Hz, 1H), 2.75 (br dd, J=5.4, 2.6 Hz, 0.5H), 2.58 (br dd, J=6.3, 3.6 Hz, 0.5H), 2.21 (ddd, J=13.5, 9.5, 3.7 Hz, 0.5H), 2.12-1.94 (m, 1H), 1.79-1.67 (m, 0.5H), 1.24 (dd, J=10.5, 6.9 Hz, 3H).

Intermediate 92c.
(4R)-2-amino-5,5,5-trifluoro-4-methylpentanoate hydrogen chloride Salt

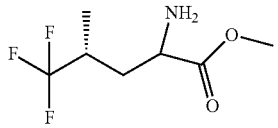

To a solution of Intermediate 92b (0.26 g, 1.4 mmol) dissolved in MeOH (11 mL) was added thionyl chloride (0.21 mL, 2.8 mmol) and heated to 35° C. for 60 hours. The reaction solution was concentrated under reduced pressure to dryness to afford Intermediate 92c which was used without further purification. MS (ESI) m/z 200.0 (M+H)$^+$

Intermediate 93b.
(4S)-2-amino-5,5,5-trifluoro-4-methylpentanoic acid

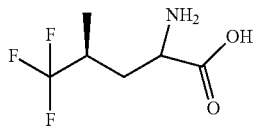

To a microwave vessel containing Intermediate 93a (0.63 g, 3.0 mmol) was added a 2M solution of sodium hydroxide (7.5 mL) and heated to 150° C. in microwave for 30 m. The reaction mixture was neutralized with 1M HCl to obtain a suspension of pH 4-6 material that was filtered, washed, dried for 12 h to furnish Intermediate 93b (220 mg, 1.2 mmol, 40% yield) as a mixture of diastereomers: MS (ESI) m/z 186.0 (M+H)$^+$, $^1$H NMR (500 MHz, METHANOL-$d_4$) δ 3.61 (br dd, J=9.1, 5.2 Hz, 1H), 2.83-2.69 (m, 0.5H), 2.58 (br d, J=2.2 Hz, 0.5H), 2.21 (ddd, J=13.3, 9.6, 3.4 Hz, 0.5H), 2.13-1.94 (m, 1H), 1.72 (ddd, J=13.8, 9.4, 5.0 Hz, 0.5H), 1.24 (br dd, J=10.5, 6.9 Hz, 3H).

Intermediate 93c.
(4S)-2-amino-5,5,5-trifluoro-4-methylpentanoate hydrogen chloride Salt

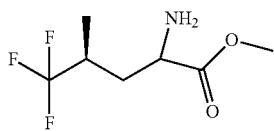

To a solution of Intermediate 93b (0.22 g, 1.2 mmol) dissolved in MeOH (10 mL) was added thionyl chloride (0.17 mL, 2.4 mmol) and heated to 35° C. for 60 hours. The reaction solution was concentrated under reduced pressure to dryness to afford Intermediate 93c which was used without further purification. MS (ESI) m/z 200.0 (M+H)$^+$

Example 80. Preparation of 2-(((aR)-6-(3-(3-chlorophenyl)-2,5-dioxoimidazolidin-1-yl)spiro[3.3]heptan-2-yl)oxy)nicotinamide

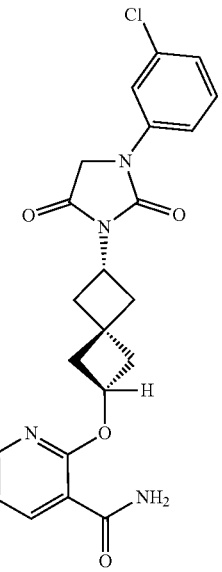

Intermediate 80a. Preparation of 2-(((aR)-6-amino-spiro[3.3]heptan-2-yl)oxy)nicotinonitrile

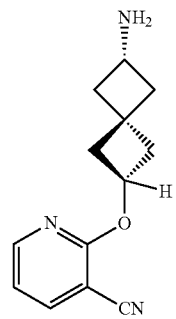

To a solution of Intermediate 1-3 (5.4 g, 15 mmol) dissolved in EtOH (150 mL) was added 10% Pd-C (0.79 g, 0.74 mmol) and the atmosphere replaced hydrogen under atmospheric pressure. The reaction mixture was stirred for 16 h after which the reaction mixture was filtered and concentrated under reduced pressure to afford Intermediate 80a (3.4 g, 15 mmol, 100% yield) which was used without further purification. MS (ESI) m/z 230.2 (M+H)$^+$.

Intermediate 80b. Preparation of 4-nitrophenyl ((aR)-6-((3-cyanopyridin-2-yl)oxy)spiro[3.3]heptan-2-yl)carbamate

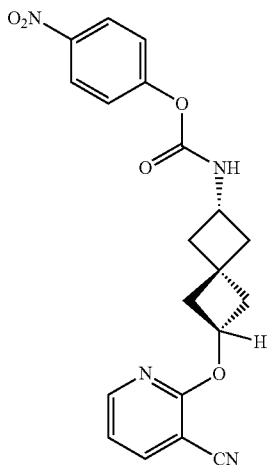

To a solution of Intermediate 80a (3.4 g, 15 mmol) dissolved in THF (390 mL) was added DIEA (3.9 mL, 22 mmol) followed by 4-nitrophenyl chloroformate (3.6 g, 18 mmol) in one portion. The reaction mixture was allowed to stir for 16 h and was used without further purification in the subsequent urea formation step. MS (ESI) m/z 394.9 (M+H)$^+$.

Intermediate 80c. Preparation of methyl (((aR)-6-((3-cyanopyridin-2-yl)oxy)spiro[3.3]heptan-2-yl)carbamoyl)glycinate

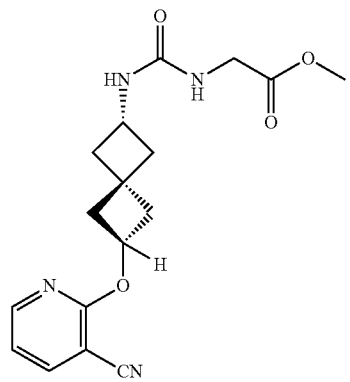

A mixture of Intermediate 80b (1.5 g, 12 mmol) and DIEA (8.4 mL, 48 mmol) was dissolved in anhydrous THF (60 mL), and a solution of methyl glycinate hydrogen chloride salt (320 mL, 12 mmol) was added and then heated to 50° C. for 16 h. The reaction mixture was cooled to rt and the resulting solution was partitioned between EtOAc and 1 M ph 7 phosphate buffer and the organic layer was concentrated under reduced pressure to furnish Intermediate 80c (4.1 g, 12 mmol, 100% yield) which was used without further purification. MS (ESI) m/z 345.2 (M+H)$^+$.

Intermediate 80d. Preparation of 2-(((aR)-6-(2,5-dioxoimidazolidin-1-yl)spiro[3.3]heptan-2-yl)oxy)nicotinonitrile

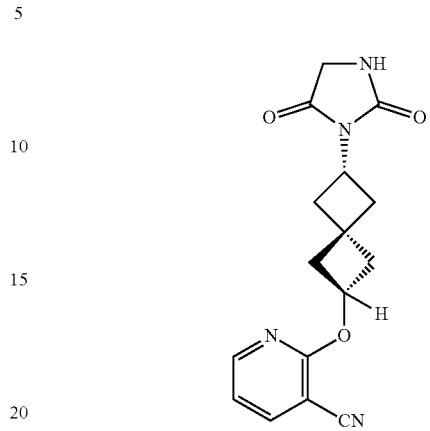

To a solution of Intermediate 80c (4.1 g, 12 mmol) dissolved in MeOH (40 mL) was added sodium methoxide (1.4 mL, 6.0 mmol) and the reaction mixture heated to 50° C. for 2 h. The reaction mixture was diluted with EtOAc, and washed 3× with water, 1× with brine and the resultant organic solution dried over MgSO$_4$. The solution was filtered and concentrated under reduced pressure to furnish Intermediate 80d (2.3 g, 7.4 mmol, 61% yield) which was used without further purification: $^1$H NMR (500 MHz, chloroform-d) δ 8.33 (dd, J=5.1, 2.1 Hz, 1H), 7.87 (dd, J=7.7, 1.9 Hz, 1H), 6.97 (dd, J=7.4, 5.0 Hz, 1H), 5.33-5.20 (m, 2H), 4.62-4.46 (m, 1H), 3.91 (d, J=1.1 Hz, 2H), 3.02 (td, J=10.2, 5.0 Hz, 2H), 2.78-2.69 (m, 1H), 2.68-2.59 (m, 1H), 2.44-2.26 (m, 4H). MS (ESI) m/z 313.1 (M+H)$^+$.

Intermediate 80e. Preparation of 2-(((aR)-6-(3-(3-chlorophenyl)-2,5-dioxoimidazolidin-1-yl)spiro[3.3]heptan-2-yl)oxy)nicotinonitrile

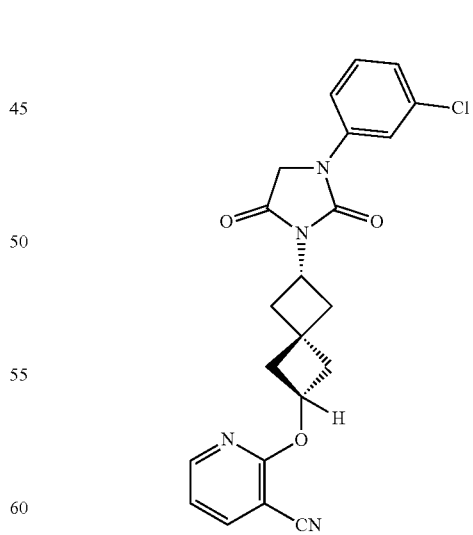

To a mixture of Cs$_2$CO$_3$ (0.066 g, 0.20 mmol) and 1-chloro-3-iodobenzene (0.024 g, 0.10 mmol) was added a pre-prepared slurry of Intermediate 80d (0.047 g, 0.15 mmol), N1,N2-dimethylethane-1,2-diamine (11 μL, 0.10 mmol), and copper(I) iodide (10 mg, 0.05 mmol) suspended in dioxane (0.40 mL). The reaction mixture was heated in a sealed vessel to 80° C. for 16 h. The reaction mixture was partitioned between sat. aq. NH₄Cl and EtOAc, and the organic layer was concentrated to furnish Intermediate 80e which was used without further purification. MS (ESI) m/z 423.2 (M+H)⁺.

Example 80. Preparation of 2-(((aR)-6-(3-(3-chlorophenyl)-2,5-dioxoimidazolidin-1-yl)spiro[3.3]heptan-2-yl)oxy)nicotinamide

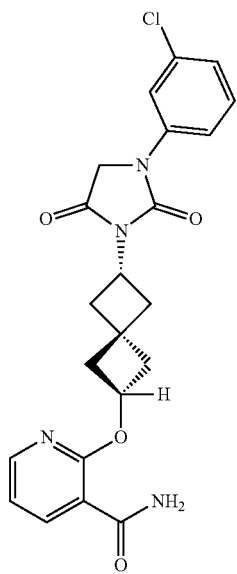

To a solution of Intermediate 80e (43 mg, 0.10 mmol) dissolved in DMSO (0.4 mL) was added K₂CO₃ (14 mg, 0.10 mmol), H₂O₂ (0.031 mL, 0.35 mmol), and 0.050 mL H₂O. The reaction mixture was stirred 16 h at room temperature. The resulting material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 30% B, 30-70% B over 20 minutes, then a 4-minute hold at 100% B; Flow Rate: 20 mL/min; Column Temperature: 25 C. Fractions containing the desired product were combined and dried via centrifugal evaporation to furnish Example 80 (14 mg, 0.031 mmol, 31% yield). MS (ESI) m/z 441.0 (M+H)⁺. ¹H NMR (500 MHz, DMSO-d₆) δ 8.34-8.23 (m, 1H), 8.17 (dd, J=7.5, 1.7 Hz, 1H), 7.78 (s, 1H), 7.72-7.57 (m, 2H), 7.51 (br d, J=8.2 Hz, 1H), 7.41 (t, J=8.1 Hz, 1H), 7.19 (br d, J=7.9 Hz, 1H), 7.12 (dd, J=7.3, 4.9 Hz, 1H), 5.24 (quin, J=7.0 Hz, 1H), 4.54-4.34 (m, 3H), 2.90 (br t, J=10.1 Hz, 2H), 2.70 (dt, J=11.0, 5.8 Hz, 1H), 2.59-2.53 (m, 1H), 2.44-2.35 (m, 1H), 2.33-2.21 (m, 3H). Analytical HPLC RT=1.851 min (Method A) and 1.887 min (Method B), purity=100%.

Examples 81-89 were prepared were prepared from commercially available aryl iodides analogously to the procedure outlined above for Example 80.

Example 90 was prepared using the general methods described for Example 37 from the commercially available allyl chloride with Example 91 prepared from Example 90 via the following method:

Example 91. Preparation of 2-(((aR)-6-(4-(2-methyl-3-phenylpropyl)-2,5-dioxoimidazolidin-1-yl)spiro[3.3]heptan-2-yl)oxy)nicotinamide

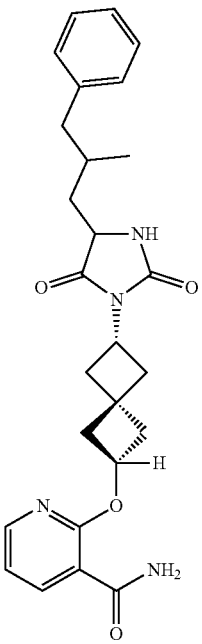

To a solution of Example 90 (47 mg, 0.10 mmol) dissolved in EtOH (1 mL) was added Pd/C 10% wt. (5 mg, 5 μmol) and the atmosphere was flushed with nitrogen and subsequently replaced with hydrogen at 55 (psig) for 2 days. The reaction solution was filtered and was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 30% B, 30-70% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to furnish Example 91: MS (ESI) m/z 463.4 (M+H)⁺. ¹H NMR (500 MHz, DMSO-d₆) δ 8.25 (br d, J=4.7 Hz, 1H), 8.17 (br d, J=7.4 Hz, 1H), 7.65-7.41 (m, 2H), 7.26 (q, J=7.2 Hz, 2H), 7.21-7.13 (m, 3H), 7.10 (dd, J=7.3, 5.0 Hz, 1H), 5.23 (br t, J=6.9 Hz, 1H), 4.32 (quin, J=8.8 Hz, 1H), 4.09-3.96 (m, 1H), 3.88-3.72 (m, 1H), 3.29-3.06 (m, 1H), 2.92-2.77 (m, 2H), 2.75-2.59 (m, 2H), 2.44-2.16 (m, 5H), 2.13-1.88 (m, 1H), 1.74-1.37 (m, 1H), 0.90-0.73 (m, 3H)ᵇ. Analytical HPLC RT=1.84 min, 1.86 min (Method A) and 1.86 min, 1.89 min (Method B), purity=97.5%.

Intermediate 102a: Preparation of benzyl ((αR)-6-((3-carbamoyl-6-methoxypyridin-2-yl)oxy)spiro[3.3]heptan-2-yl)carbamate

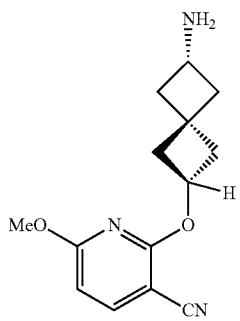

Benzyl ((αR)-6-hydroxyspiro[3.3]heptan-2-yl)carbamate (1.21 g, 4.60 mmol) was added to THF (15 mL) and the solution was cooled (0° C.). To the solution was added KOtBu (0.62 g, 4.6 mmol) and the reaction mixture was stirred at this temperature for 0.5 h, followed by the addition of 2-chloro-6-methoxynicotinonitrile (0.78 g, 4.60 mmol). The reaction mixture was stirred at 0° C. and allowed to warm to rt over 12 h. The reaction mixture was treated with water (20 mL) and the organic portions were extracted with EtOAc (2×25 mL), dried (MgSO$_4$), filtered and concentrated under reduced pressure. LCMS m/z=394.08 (M+H)$^+$. The residue was re-dissolved in DMSO (2 mL) and to this solution was added K$_2$CO$_3$ (3.18 g, 23 mmol) followed by the addition of H$_2$O$_2$ (35%, 0.41 mL) and the solution was stirred at rt for 12 h. The reaction mixture was quenched by the addition of water (25 mL) and extracted the organic portion with EtOAc (2×25 mL), dried (MgSO$_4$), filtered and evaporated under reduced pressure to an oil. The residue was purified by silica gel chromatography (12 g) and eluted with hexane/ethylacetate to afford intermediate 102a as a white solid (1.0 g, 54%). LCMS m/z=412.08 (M+H)$^+$. $^1$H NMR (400 MHz, CDCl$_3$) δ 8.46-8.32 (d, 1H), 7.57 (br d, J=9.5 Hz, 1H), 7.46-7.30 (m, 5H), 6.51-6.37 (d, 1H), 5.25 (quin, J=7.2 Hz, 1H), 5.17-5.03 (m, 2H), 3.96 (s, 3H), 2.34-2.19 (m, 1H), 2.12-1.96 (m, 2H), 1.60 (s, 5H)

Intermediate 102b: Preparation of 2-(((αR)-6-aminospiro[3.3]heptan-2-yl)oxy)-6-methoxynicotinamide

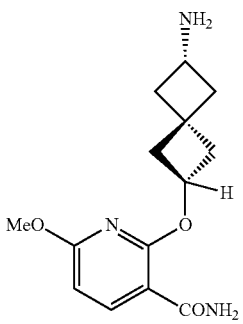

Intermediate 102a was dissolved in solution of methanol (10 mL) EtOAc (2 mL) and transferred to a Parr bottle. Palladium on carbon (10 wt %, 0.1 g) was added and the reaction mixture was subjected to hydrogenation at 60 psi for 4 h. The reaction mixture was filtered through a celite pad and the celite washed with excess EtOAc. Evaporation of the solvents under reduced pressure afforded intermediate 102b as a solid. LCMS m/z=278.08 (M+H)$^+$. 1H NMR (400 MHz, CD$_3$OD) Shift 8.27 (d, J=8.4 Hz, 1H), 6.47 (d, J=8.4 Hz, 1H), 5.39-5.21 (m, 1H), 3.98 (s, 2H), 3.48-3.37 (m, 1H), 2.78-2.14 (m, 6H), 2.03-1.91 (m, 2H)

Example 102 Preparation of 2-(((αR)-6-((3R)-2,5-dioxo-3-(3,3,3-trifluoro-2-methylpropyl)pyrrolidin-1-yl)spiro[3.3]heptan-2-yl)oxy)-6-methoxynicotinamide

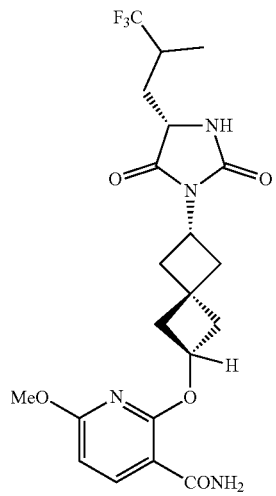

2-(((αR)-6-aminospiro[3.3]heptan-2-yl)oxy)-6-methoxynicotinamide (28 mg, 0.10 mmol) was stirred in THF (2 mL). To this solution was added sequentially 4-nitrophenyl chloroformate (20 mg, 0.10 mg) followed by Hünig's base (13 mg, 0.10 mmol) and the reaction mixture was stirred at rt for 0.5 h. A THF (1 mL) solution of methyl (2S)-2-amino-5,5,5-trifluoro-4-methylpentanoate (intermediate 91c, 20 mg, 0.10 mmol) was added and the resulting reaction mixture stirred at rt for 0.5 h. LCMS m/z=503 ((M+H)$^+$). The reaction mixture was concentrated and the residue dissolved in MeOH (3 mL) followed by the addition of NaOMe (0.5 mL, 25%) and heated for 45 min. at 40° C. The reaction mixture was quenched by the addition of HCl (5 mL, 1N) and the organic portions were extracted with EtOAc (2×20 mL), dried (MgSO$_4$), filtered and evaporated under reduced pressure to an oil. The residue was purified by chiral SFC (Column: Chiralpak IA SFC, 21×250 mm, 5 micron. Mobile Phase: 25% MeOH/75% CO$_2$. Flow Conditions: 45 mL/min 150 Bar, 40 C. Detector Wavelength: 285 nm. Injection Details: 1.0 ml of 54 mg in 2 ml MeOH) to afford Example 92.

Diastereomer A (6.0 mg, 12%): HPLC purity 95% (Sunfire C18 3.5 um, 3.0×150 mm; Solvent A=0.05% TFA in H$_2$O:CH$_3$CN (95:5). Solvent B=0.05% TFA in CH$_3$CN:H$_2$O (95:5)). LCMS m/z=471.08 (M+H)$^+$. $^1$H NMR (400 MHz, CD$_3$OD) δ 8.27 (d, J=8.6 Hz, 1H), 6.47 (d, J=8.4 Hz, 1H), 5.31 (quin, J=7.1 Hz, 1H), 4.50 (quin, J=8.8 Hz, 1H), 4.17-4.08 (m, 1H), 3.99 (s, 3H), 3.00 (t, J=10.3 Hz, 2H), 2.88-2.78 (m, 1H), 2.70 (dt, J=12.2, 5.9 Hz, 1H), 2.57-2.29 (m, 5H), 1.92-1.81 (m, 2H), 1.21 (d, J=6.8 Hz, 3H).

Diasteromer B, Example 92 (6.1 mg, 13%). HPLC purity 95% (Sunfire C18 3.5 um, 3.0×150 mm; Solvent A=0.05% TFA in H$_2$O:CH$_3$CN (95:5). Solvent B=0.05% TFA in CH$_3$CN:H$_2$O (95:5)). LCMS m/z=471.08 (M+H)$^+$. $^1$H NMR (500 MHz, CD$_3$OD) δ 8.27 (d, J=8.3 Hz, 1H), 6.46 (d, J=8.3 Hz, 1H), 5.31 (quin, J=7.2 Hz, 1H), 4.49 (quin, J=8.8 Hz, 1H), 4.14-4.09 (m, 1H), 3.99-3.96 (m, 3H), 3.02-2.94 (m, 2H), 2.85-2.75 (m, 1H), 2.72-2.49 (m, 2H), 2.45-2.23 (m, 5H), 2.14 (dt, J=14.3, 6.1 Hz, 1H), 1.74-1.60 (m, 1H), 1.18 (d, J=6.9 Hz, 3H).

Examples 93-98 were prepared as a roughly 1:1 mixture of diastereomers from commercially available aldehydes analogously to the procedure outlined above for Example 68. Where the isolates were separable by reverse phase HPLC the difference in retention times are indicated in Table 1. Examples 99 & 100 were prepared from Examples 96 & 97 according to the methods outlined below for the conversion Example 96 to Example 99.

Example 100. Preparation of 2-(((αR)-6-(2,5-dioxo-4-((trans-4-benzylaminocyclohex-1-yl)methylene)-2,5-dioxoimidazolidin-1-yl)spiro[3.3]heptan-2-yl)oxy)nicotinamide

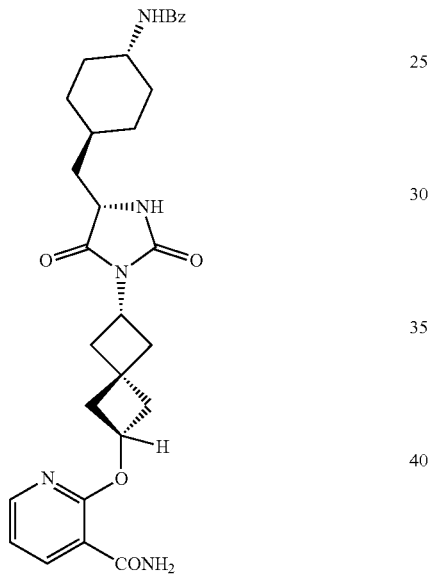

A slurry of Example 97 (0.115 g, 0.200 mmol), 10 wt % Pd/C (0.021 g, 0.020 mmol), and EtOH (2.0 ml) was blanketed under H$_2$ (balloon) and allowed to stir overnight. The mixture was then filtered through celited, and concentrated. The residue was dissolved in 2 mL of DCM and used as a 0.1 M solution. A 1 mL portion of this solution was then treated with Hünig's Base (50 µl, 0.30 mmol) and benzoyl chloride (12 µl, 0.10 mmol) and allowed to stir overnight. The resulting mixture was then concentrated and purified by preparative HPLC to furnish 2-(((αR)-6-(2,5-dioxo-4-((trans-4-benzylaminocyclohex-1-yl)methylene)-2,5-dioxoimidazolidin-1-yl)spiro[3.3]heptan-2-yl)oxy)nicotinamide (2.0 mg, 3.6 mmol, 4%) as a 1:1 mixture of diastereomers. MS (ESI) m/z: 546.4 (M+H)+. $^1$H NMR (500 MHz, DMSO-d$_6$) δ 8.31 (s, 1H), 8.28-8.24 (m, 1H), 8.22 (br d, J=7.9 Hz, 1H), 8.16 (dd, J=7.5, 1.7 Hz, 1H), 7.82 (br d, J=7.3 Hz, 2H), 7.69-7.58 (m, 2H), 7.54-7.42 (m, 4H), 7.11 (dd, J=7.3, 4.9 Hz, 1H), 5.21 (quin, J=7.1 Hz, 1H), 4.33 (quin, J=8.6 Hz, 1H), 4.05-3.99 (m, 1H), 3.81-3.66 (m, 1H), 2.91-2.77 (m, 2H), 2.67 (dt, J=11.4, 5.9 Hz, 1H), 2.34-2.12 (m, 5H), 1.90-1.77 (m, 3H), 1.69 (br d, J=12.8 Hz, 2H), 1.56 (br d, J=4.9 Hz, 2H), 1.45-1.29 (m, 1H), 1.15-0.87 (m, 2H). Analytical HPLC RT=1.492 min (Method A) and 1.526 min (Method B), purity=99%.

TABLE 2

| Ex. No. | Structure | Name | MS (ESI) (M + H) | ¹H NMR | LC RT$^a$ (min) and chiral conditions when separated |
|---|---|---|---|---|---|
| 81 | 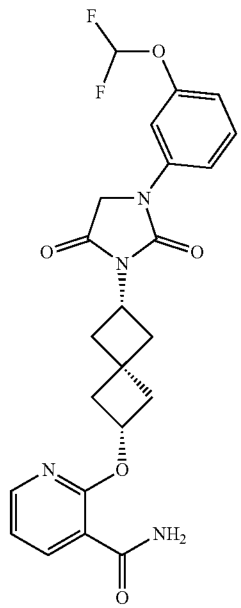 | 2-(((aR)-6-(3-(2-(difluoromethoxy)phenyl)-2,5-dioxoimidazolidin-1-yl)spiro[3.3]heptan-2-yl)oxy)nicotinamide | 473.2 | ¹H NMR (500 MHz, DMSO-d6) δ 8.26 (br d, J = 3.1 Hz, 1H), 8.16 (br d, J = 7.3 Hz, 1H), 7.64 (br d, J = 10.4 Hz, 2H), 7.55 (br d, J = 7.6 Hz, 1H), 7.47-7.38 (m, 1H), 7.36-7.27 (m, 2H), 7.26-6.92 (m, 2H), 5.22 (quin, J = 7.0 Hz, 1H), 4.44 (quin, J = 8.9 Hz, 1H), 4.31 (s, 2H), 2.88 (br t, J = 10.1 Hz, 2H), 2.69 (dt, J = 11.1, 5.7 Hz, 1H), 2.44-2.33 (m, 1H), 2.32-2.20 (m, 3H)$^b$ | 1.66 |
| 82 | 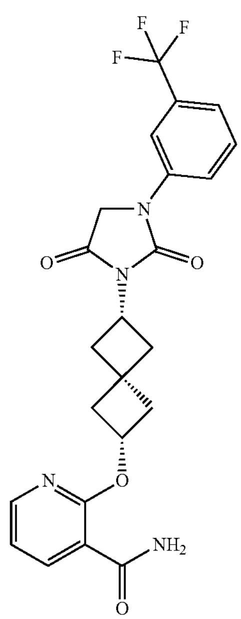 | 2-(((aR)-6-(2,5-dioxo-3-(3-(trifluoromethyl)phenyl)imidazolidin-1-yl)spiro[3.3]heptan-2-yl)oxy)nicotinamide | 475.2 | ¹H NMR (500 MHz, DMSO-d₆) δ 8.31-8.24 (m, 1H), 8.17 (dd, J = 7.3, 1.8 Hz, 1H), 8.11 (s, 1H), 7.75 (br d, J = 7.9 Hz, 1H), 7.70-7.57 (m, 3H), 7.48 (br d, J = 7.6 Hz, 1H), 7.11 (dd, J = 7.3, 4.9 Hz, 1H), 5.23 (quin, J = 7.1 Hz, 1H), 4.51-4.39 (m, 3H), 2.90 (br t, J = 10.2 Hz, 2H), 2.70 (dt, J = 11.2, 5.8 Hz, 1H), 2.60-2.53 (m, 1H), 2.45-2.34 (m, 1H), 2.32-2.21 (m, 3H) | 1.96 |

TABLE 2-continued

| Ex. No. | Structure | Name | MS (ESI) (M + H) | ¹H NMR | LC RT[a] (min) and chiral conditions when separated |
|---|---|---|---|---|---|
| 83 | 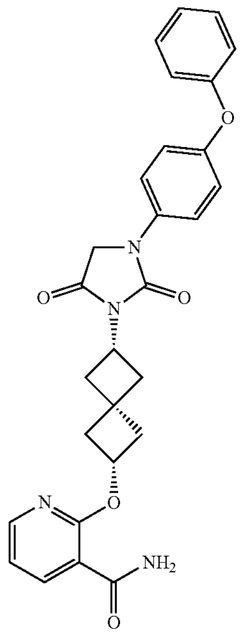 | 2-(((aR)-6-(2,5-dioxo-3-(4-phenoxyphenyl)imidazolidin-1-yl)spiro[3.3]heptan-2-yl)oxy)nicotinamide | 499.1 | ¹H NMR (500 MHz, DMSO-d$_6$) δ 8.31-8.22 (m, 1H), 8.17 (dd, J = 7.5, 1.7 Hz, 1H), 7.72-7.57 (m, 4H), 7.44-7.33 (m, 2H), 7.19-7.08 (m, 2H), 7.05 (br d, J = 9.2 Hz, 2H), 6.98 (br d, J = 7.9 Hz, 2H), 5.23 (quin, J = 6.9 Hz, 1H), 4.52-4.34 (m, 3H), 2.91 (br t, J = 10.1 Hz, 2H), 2.70 (dt, J = 11.2, 5.8 Hz, 1H), 2.44-2.34 (m, 1H), 2.32-2.21 (m, 3H)[b] | 2.04 |
| 84 | 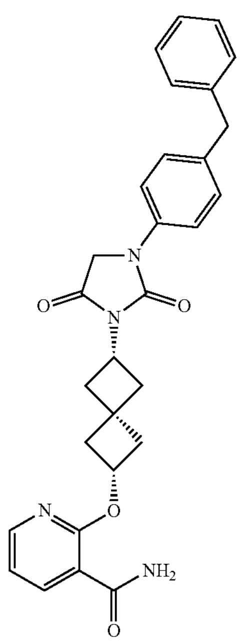 | 2-(((aR)-6-(3-(4-benzylphenyl)-2,5-dioxoimidazolidin-1-yl)spiro[3.3]heptan-2-yl)oxy)nicotinamide | 497.3 | ¹H NMR (500 MHz, DMSO-d$_6$) δ 8.26 (br d, J = 3.6 Hz, 1H), 8.18 (br d, J = 7.4 Hz, 1H), 7.65-7.43 (m, 4H), 7.32-7.25 (m, 2H), 7.25-7.15 (m, 5H), 7.10 (dd, J = 7.4, 4.9 Hz, 1H), 5.25 (quin, J = 7.1 Hz, 1H), 4.44 (quin, J = 8.7 Hz, 1H), 4.36 (s, 2H), 3.92 (s, 2H), 2.90 (br t, J = 10.1 Hz, 2H), 2.70 (dt, J = 11.5, 5.8 Hz, 1H), 2.60-2.53 (m, 1H), 2.44-2.34 (m, 1H), 2.33-2.20 (m, 3H) | 2.15 |

TABLE 2-continued

| Ex. No. | Structure | Name | MS (ESI) (M + H) | ¹H NMR | LC RT[a] (min) and chiral conditions when separated |
|---|---|---|---|---|---|
| 85 | 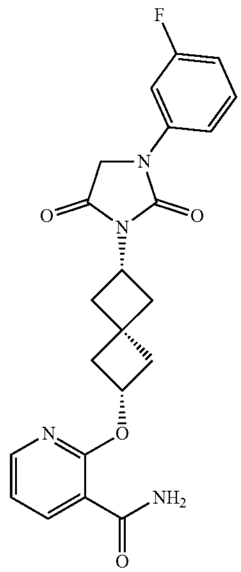 | 2-(((aR)-6-(3-(3-fluorophenyl)-2,5-dioxoimidazolidin-1-yl)spiro[3.3]heptan-2-yl)oxy)nicotinamide | 425.1 | ¹H NMR (500 MHz, DMSO-d$_6$) δ 8.26 (br d, J = 3.4 Hz, 1H), 8.16 (br d, J = 7.3 Hz, 1H), 7.65 (br d, J = 9.5 Hz, 2H), 7.54 (br d, J = 11.6 Hz, 1H), 7.46-7.31 (m, 2H), 7.11 (dd, J = 7.2, 5.0 Hz, 1H), 6.96 (br t, J = 7.8 Hz, 1H), 5.23 (quin, J = 7.0 Hz, 1H), 4.52-4.32 (m, 3H), 2.89 (br t, J = 10.1 Hz, 2H), 2.70 (dt, J = 11.5, 5.7 Hz, 1H), 2.58-2.52 (m, 1H), 2.44-2.33 (m, 1H), 2.26 (dq, J = 11.8, 5.9 Hz, 3H) | 1.79 |
| 86 | 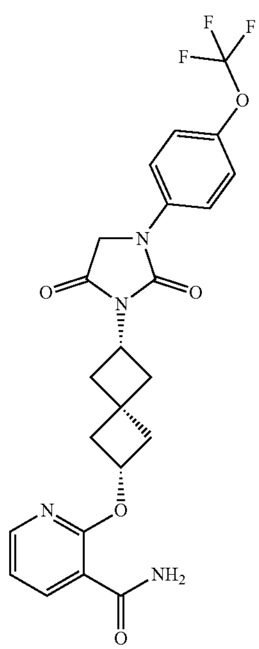 | 2-(((aR)-6-(2,5-dioxo-3-(4-(trifluoromethoxy)phenyl)imidazolidin-1-yl)spiro[3.3]heptan-2-yl)oxy)nicotinamide | 497.3 | ¹H NMR (500 MHz, DMSO-d$_6$) δ 8.26 (br d, J = 3.1 Hz, 1H), 8.19-8.11 (m, 1H), 7.77-7.56 (m, 4H), 7.39 (br d, J = 8.9 Hz, 2H), 7.11 (dd, J = 7.3, 4.9 Hz, 1H), 5.29-5.15 (m, 1H), 4.51-4.35 (m, 3H), 2.89 (br t, J = 10.2 Hz, 2H), 2.76-2.65 (m, 1H), 2.44-2.33 (m, 1H), 2.31-2.19 (m, 3H)[b] | 1.95 |

| Ex. No. | Structure | Name | MS (ESI) (M + H) | ¹H NMR | LC RT[a] (min) and chiral conditions when separated |
|---|---|---|---|---|---|
| 87 | 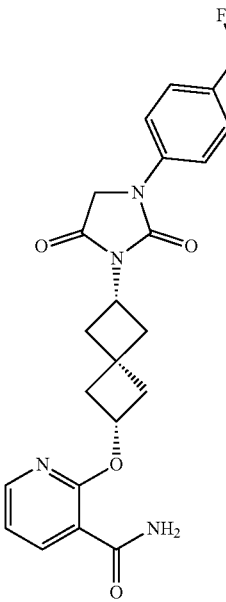 | 2-(((aR)-6-(2,5-dioxo-3-(4-(trifluoromethyl)phenyl)imidazolidin-1-yl)spiro[3.3]heptan-2-yl)oxy)nicotinamide | 475.0 | ¹H NMR (500 MHz, DMSO-$d_6$) δ 8.30-8.21 (m, 1H), 8.16 (dd, J = 7.5, 1.4 Hz, 1H), 7.85-7.77 (m, 2H), 7.75-7.65 (m, 3H), 7.61 (br s, 1H), 7.11 (dd, J = 7.3, 5.2 Hz, 1H), 5.21 (quin, J = 7.1 Hz, 1H), 4.49-4.36 (m, 3H), 2.88 (br t, J = 10.2 Hz, 2H), 2.69 (dt, J = 11.3, 5.6 Hz, 1H), 2.43-2.34 (m, 1H), 2.32-2.19 (m, 3H)[b] | 1.84 |
| 88 | 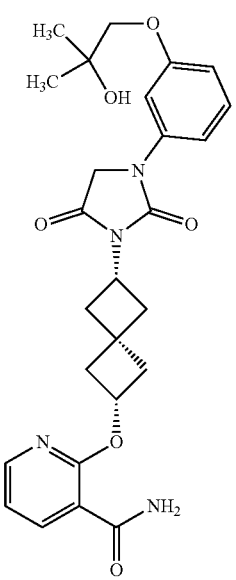 | 2-(((aR)-6-(3-(3-(2-hydroxy-2-methylpropoxy)phenyl)-2,5-dioxoimidazolidin-1-yl)spiro[3.3]heptan-2-yl)oxy)nicotinamide | 495.2 | ¹H NMR (500 MHz, DMSO-$d_6$) δ 8.28 (br d, J = 3.4 Hz, 1H), 8.17 (br d, J = 7.3 Hz, 1H), 7.74-7.54 (m, 2H), 7.34-7.24 (m, 2H), 7.14-7.05 (m, 2H), 6.72 (br d, J = 8.2 Hz, 1H), 5.24 (quin, J = 7.1 Hz, 1H), 4.53-4.36 (m, 3H), 3.71 (s, 2H), 2.92 (br t, J = 9.9 Hz, 2H), 2.75-2.67 (m, 1H), 2.59-2.53 (m, 1H), 2.45-2.36 (m, 1H), 2.33-2.20 (m, 3H), 1.27-1.19 (m, 6H)[b] | 1.56 |

TABLE 2-continued

| Ex. No. | Structure | Name | MS (ESI) (M + H) | ¹H NMR | LC RT[a] (min) and chiral conditions when separated |
|---|---|---|---|---|---|
| 89 | 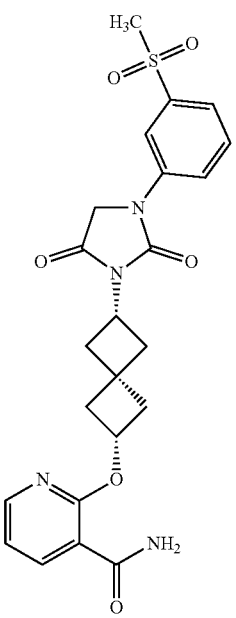 | 2-(((aR)-6-(3-(3-(methylsulfonyl)phenyl)-2,5-dioxoimidazolidin-1-yl)spiro[3.3]heptan-2-yl)oxy)nicotinamide | 485.0 | ¹H NMR (500 MHz, DMSO-$d_6$) δ 8.30 (s, 1H), 8.26 (dd, J = 4.7, 1.7 Hz, 1H), 8.16 (dd, J = 7.5, 1.7 Hz, 1H), 7.77 (br d, J = 3.4 Hz, 1H), 7.71-7.58 (m, 4H), 7.11 (dd, J = 7.5, 5.0 Hz, 1H), 5.23 (quin, J = 7.0 Hz, 1H), 4.53-4.38 (m, 3H), 3.20 (s, 3H), 2.90 (br t, J = 10.2 Hz, 2H), 2.70 (dt, J = 11.4, 5.8 Hz, 1H), 2.60-2.53 (m, 1H), 2.43-2.35 (m, 1H), 2.32-2.19 (m, 3H) | 1.42 |
| 90 | 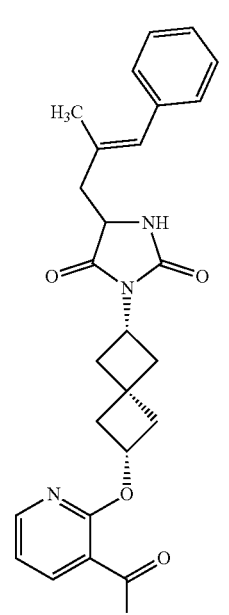 | 2-(((aR)-6-(4-((E)-2-methyl-3-phenylallyl)-2,5-dioxoimidazolidin-1-yl)spiro[3.3]heptan-2-yl)oxy)nicotinamide | 461.3 | ¹H NMR (500 MHz, DMSO-$d_6$) δ 8.34-8.23 (m, 2H), 8.16 (dd, J = 7.5, 1.7 Hz, 1H), 7.75-7.54 (m, 2H), 7.40-7.29 (m, 2H), 7.28-7.17 (m, 3H), 7.11 (dd, J = 7.3, 4.9 Hz, 1H), 6.32 (s, 1H), 5.21 (quin, J = 6.9 Hz, 1H), 4.34 (quin, J = 8.8 Hz, 1H), 4.24 (br dd, J = 7.3, 4.3 Hz, 1H), 2.83 (q, J = 9.1 Hz, 2H), 2.67 (dt, J = 11.6, 5.8 Hz, 1H), 2.59 (br dd, J = 13.6, 3.8 Hz, 1H), 2.38 (br dd, J = 13.7, 7.9 Hz, 1H), 2.33-2.13 (m, 4H), 1.81 (s, 3H)[b] | 1.76 |

TABLE 2-continued

| Ex. No. | Structure | Name | MS (ESI) (M + H) | 1H NMR | LC RT[a] (min) and chiral conditions when separated |
|---|---|---|---|---|---|
| 92 | 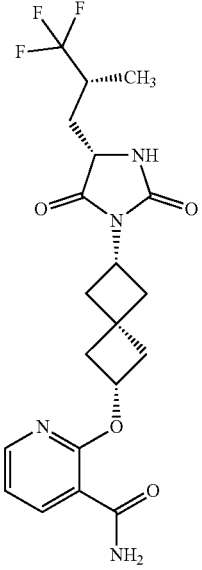 | 2-(((aR)-6-((S)-2,5-dioxo-4-((R)-3,3,3-trifluoro-2-methylpropyl)imidazolidin-1-yl)spiro[3.3]heptan-2-yl)oxy)nicotinamide | 441.1 | $^1$H NMR (500 MHz, CDCl$_3$) δ 8.52 (dd, J = 7.4, 1.9 Hz, 1H), 8.28 (dd, J = 4.8, 2.1 Hz, 1H), 7.79 (br s, 1H), 7.06 (dd, J = 7.6, 4.8 Hz, 1H), 5.78 (br s, 1H), 5.35 (dd, J = 14.4, 7.3 Hz, 2H), 4.63-4.45 (m, 1H), 4.14-4.03 (m, 1H), 3.08-2.96 (m, 2H), 2.80 (dt, J = 11.6, 5.8 Hz, 1H), 2.72 (dt, J = 12.2, 6.0 Hz, 1H), 2.66-2.49 (m, 1H), 2.47-2.38 (m, 1H), 2.35-2.18 (m, 4H), 1.84-1.70 (m, 1H), 1.22 (d, J = 6.9 Hz, 3H) | 1.50 Chiralpak IC, 4.6 x 250 mm, 5 micron, 25% MeOH/75% CO$_2$, 2.0 mL/min, 150 Bar, t$_R$ = 3.40 min |
| 93 | 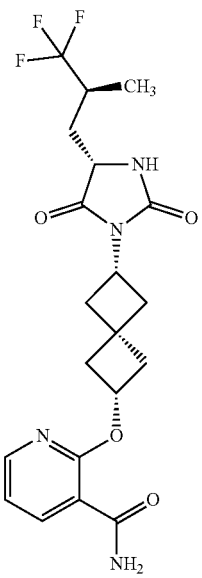 | 2-(((aR)-6-((S)-2,5-dioxo-4-((S)-3,3,3-trifluoro-2-methylpropyl)imidazolidin-1-yl)spiro[3.3]heptan-2-yl)oxy)nicotinamide | 441.1 | $^1$H NMR (500 MHz, CDCl$_3$) δ 8.52 (dd, J = 7.7, 1.9 Hz, 1H), 8.28 (dd, J = 4.8, 2.1 Hz, 1H), 7.80 (br s, 1H), 7.06 (dd, J = 7.6, 4.8 Hz, 1H), 5.85 (br s, 1H), 5.63 (s, 1H), 5.41-5.28 (m, 1H), 4.62-4.45 (m, 1H), 4.10-3.98 (m, 1H), 3.08-2.95 (m, 2H), 2.80 (dt, J = 11.7, 6.0 Hz, 1H), 2.71 (dt, J = 12.1, 6.1 Hz, 1H), 2.53-2.38 (m, 2H), 2.34-2.17 (m, 3H), 2.09-1.87 (m, 2H), 1.23 (d, J = 6.9 Hz, 3H) | 1.50 Chiralpack IC 4.6 x 250 mm, 5 micron, 15% MeOH/85% CO$_2$, 2.0 mL/min, 150 Bar, t$_R$ = 13.74 min |

TABLE 2-continued

| Ex. No. | Structure | Name | MS (ESI) (M + H) | ¹H NMR | LC RT[a] (min) and chiral conditions when separated |
|---|---|---|---|---|---|
| 94 | 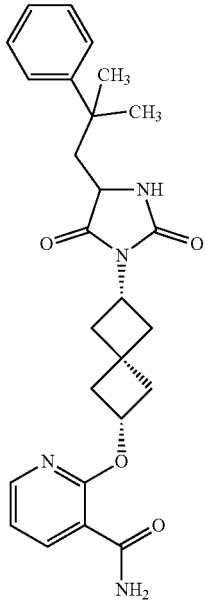 | 2-(((aR)-6-(2,5-dioxo-4-(2-phenyl-2-methylpropyl)imidazolidin-1-yl)spiro[3.3]heptan-2-yl)oxy)nicotinamide | 463.3 | ¹H NMR (500 MHz, DMSO-$d_6$) δ 8.27 (br d, J = 3.1 Hz, 1H), 8.17 (br d, J = 7.0 Hz, 1H), 7.90 (s, 1H), 7.74-7.57 (m, 2H), 7.45-7.30 (m, 4H), 7.24-7.07 (m, 2H), 5.21 (br t, J = 7.0 Hz, 1H), 4.29 (br t, J = 8.7 Hz, 1H), 3.61 (br d, J = 8.5 Hz, 1H), 3.43 (br s, 1H), 2.85-2.72 (m, 2H), 2.66 (dt, J = 11.1, 5.7 Hz, 1H), 2.48 (br d, J = 5.8 Hz, 1H), 2.34-2.11 (m, 5H), 1.70 (br dd, J = 14.3, 9.2 Hz, 1H), 1.42-1.27 (m, 6H) | 1.83 |
| 95 | 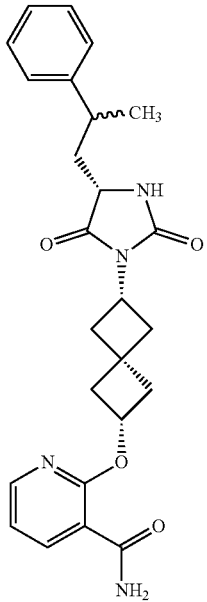 | 2-(((aR)-6-((S)-2,5-dioxo-4-(2-phenyl-propyl)imidazolidin-1-yl)spiro[3.3]heptan-2-yl)oxy)nicotinamide | 449.1 | ¹H NMR (500 MHz, DMSO-$d_6$) δ 8.42 (s, 1H), 8.25 (dd, J = 4.9, 1.8 Hz, 1H), 8.16 (dd, J = 7.5, 2.0 Hz, 1H), 7.63 (br d, J = 18.6 Hz, 2H), 7.35-7.25 (m, 4H), 7.24-7.16 (m, 1H), 7.10 (dd, J = 7.6, 4.9 Hz, 1H), 5.20 (quin, J = 7.1 Hz, 1H), 4.34-4.24 (m, 1H), 3.17 (d, J = 4.9 Hz, 1H), 2.95-2.87 (m, 1H), 2.79 (br t, J = 10.1 Hz, 2H), 2.69-2.60 (m, 1H), 2.47 (br d, J = 5.8 Hz, 1H), 2.28-2.13 (m, 4H), 2.02-1.91 (m, 1H), 1.72-1.62 (m, 1H), 1.21 (d, J = 7.0 Hz, 3H) | 1.81 |

TABLE 2-continued

| Ex. No. | Structure | Name | MS (ESI) (M + H) | ¹H NMR | LC RT[a] (min) and chiral conditions when separated |
|---|---|---|---|---|---|
| 96 | 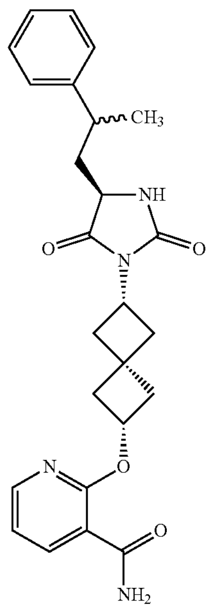 | 2-(((aR)-6-((R)-2,5-dioxo-4-(2-phenyl-propyl)imidazolidin-1-yl)spiro[3.3]heptan-2-yl)oxy)nicotinamide | 449.1 | 1H NMR (500 MHz, DMSO-d6) δ 8.31-8.22 (m, 2H), 8.16 (dd, J = 7.5, 1.7 Hz, 1H), 7.70-7.57 (m, 2H), 7.31-7.23 (m, 2H), 7.21-7.15 (m, 3H), 7.10 (dd, J = 7.3, 5.2 Hz, 1H), 5.19 (quin, J = 7.1 Hz, 1H), 4.25-4.11 (m, 1H), 3.89 (br t, J = 6.4 Hz, 1H), 3.02-2.92 (m, 1H), 2.78-2.58 (m, 3H), 2.48-2.41 (m, 1H), 2.29-2.15 (m, 3H), 2.13-2.02 (m, 1H), 1.92 (dt, J = 13.9, 6.8 Hz, 1H), 1.80 (dt, J = 13.9, 7.1 Hz, 1H), 1.19 (d, J = 6.7 Hz, 3H) | 1.73 |
| 97 | 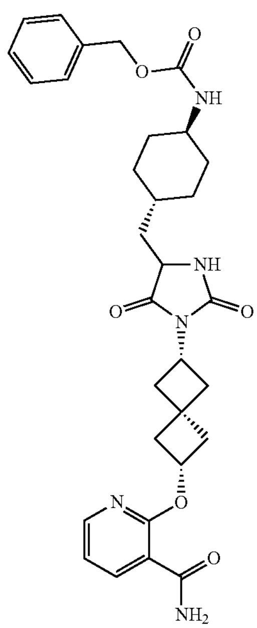 | 2-(((aR)-6-((R)-2,5-dioxo-4-(trans-4-(beznylcarbamoyl)-cyclohex-1-ylmethyl)imidazolidin-1-yl)spiro[3.3]heptan-2-yl)oxy)nicotinamide | 575.9 | 1H NMR (500 MHz, DMSO-d6) δ 8.35-8.24 (m, 2H), 8.16 (dd, J = 7.5, 1.7 Hz, 1H), 7.63 (br d, J = 18.9 Hz, 2H), 7.43-7.25 (m, 5H), 7.22-7.05 (m, 2H), 5.21 (br t, J = 7.0 Hz, 1H), 5.05-4.92 (m, 2H), 4.31 (br t, J = 8.9 Hz, 1H), 3.99 (br d, J = 8.5 Hz, 1H), 3.21 (br d, J = 4.0 Hz, 1H), 2.82 (q, J = 9.4 Hz, 2H), 2.66 (dt, J = 11.1, 5.4 Hz, 1H), 2.34-2.08 (m, 4H), 1.85-1.71 (m, 2H), 1.68-1.29 (m, 6H), 1.20-1.09 (m, 2H), 1.02-0.81 (m, 2H) | 1.78 |

TABLE 2-continued

| Ex. No. | Structure | Name | MS (ESI) (M + H) | ¹H NMR | LC RT$^a$ (min) and chiral conditions when separated |
|---|---|---|---|---|---|
| 98 | 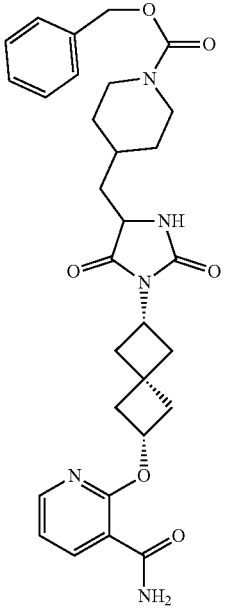 | 2-(((aR)-6-(2,5-dioxo-4-(N-benzyloxycarbonyl-piperidin-4-ylmethyl)imidazolidin-1-yl)spiro[3.3]heptan-2-yl)oxy)nicotinamide | 562.4 | 1H NMR (500 MHz, DMSO-d6) δ 8.32-8.23 (m, 2H), 8.16 (dd, J = 7.5, 1.7 Hz, 1H), 7.63 (br d, J = 17.7 Hz, 2H), 7.43-7.29 (m, 5H), 7.10 (dd, J = 7.3, 5.2 Hz, 1H), 5.21 (quin, J = 7.0 Hz, 1H), 5.05 (s, 2H), 4.32 (br t, J = 8.7 Hz, 1H), 4.10-3.92 (m, 3H), 2.88-2.76 (m, 3H), 2.65 (br d, J = 5.5 Hz, 2H), 2.48 (br s, 1H), 2.33-2.12 (m, 4H), 1.73-1.53 (m, 4H), 1.47-1.35 (m, 1H), 1.10-0.91 (m, 2H) | 1.78 |
| 99 | 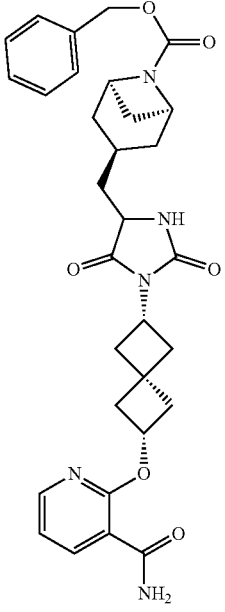 | benzyl 3-((1-((aR)-6-((3-carbamoylpyridin-2-yl)oxy)spiro[3.3]heptan-2-yl)-2,5-dioxoimidazolidin-4-yl)methyl)-8-azabicyclo[3.2.1]octane-8-carboxylate | 588.5 | 1H NMR (500 MHz, DMSO-d6) δ 8.34 (s, 1H), 8.26 (dd, J = 4.7, 1.7 Hz, 1H), 8.16 (dd, J = 7.5, 1.7 Hz, 1H), 7.64 (br d, J = 12.8 Hz, 2H), 7.43-7.26 (m, 5H), 7.11 (dd, J = 7.5, 5.0 Hz, 1H), 5.21 (quin, J = 7.0 Hz, 1H), 5.07 (br d, J = 5.5 Hz, 2H), 4.31 (br t, J = 8.7 Hz, 1H), 4.13 (br s, 2H), 3.95 (br d, J = 5.2 Hz, 1H), 3.65-3.58 (m, 2H), 2.88-2.75 (m, 2H), 2.66 (dt, J = 11.4, 5.8 Hz, 1H), 2.50-2.45 (m, 1H), 2.36-2.15 (m, 4H), 2.02 (br s, 1H), 1.92-1.70 (m, 3H), 1.53-1.42 (m, 2H), 1.38-1.29 (m, 1H), 1.28-1.05 (m, 2H) | 1.81 |

TABLE 2-continued

| Ex. No. | Structure | Name | MS (ESI) (M + H) | $^1$H NMR | LC RT$^a$ (min) and chiral conditions when separated |
|---|---|---|---|---|---|
| 101 | 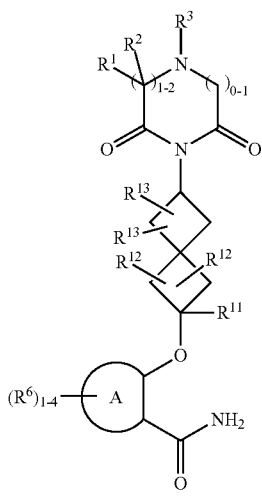 | 2-(((aR)-6-(2,5-dioxo-4-(N-benzoylpiperidin-4-ylmethyl)imidazolidin-1-yl)spiro[3.3]heptan-2-yl)oxy)nicotinamide | 532.5 | 1H NMR (500 MHz, DMSO-d6) δ 8.34-8.23 (m, 2H), 8.16 (br d, J = 7.3 Hz, 1H), 7.76-7.56 (m, 2H), 7.44 (br d, J = 3.1 Hz, 3H), 7.37 (br d, J = 3.7 Hz, 2H), 7.11 (dd, J = 7.3, 4.9 Hz, 1H), 5.22 (br t, J = 7.2 Hz, 1H), 4.33 (quin, J = 8.8 Hz, 1H), 4.04 (br s, 1H), 2.87-2.79 (m, 2H), 2.71-2.62 (m, 1H), 2.51-2.46 (m, 2H), 2.36-2.15 (m, 4H), 1.84-1.39 (m, 5H), 1.24 (s, 2H), 1.18-1.02 (m, 2H) | 1.44 |

What is claimed is:

1. A compound of Formula (I):

(I)

or a pharmaceutically acceptable salt thereof, wherein:

Ring A is 6-membered heteroaryl comprising carbon and 1-2 nitrogen atoms;

$R^1$ is selected from H, $C_{1-7}$ alkyl, $C_{2-7}$ alkenyl, $C_{2-7}$ alkynyl, —$(CR^4R^4)_n NR^5R^5$, —$(CR^4R^4)_n C_{3-10}$ carbocycle and —$(CR^4R^4)_n$-4- to 15-membered heterocycle comprising carbon atoms and 1-4 heteroatoms selected from N, $NR^8$, O, and $S(O)_p$, wherein said alkyl, alkenyl, alkynyl, carbocycle, and heterocycle are substituted with 1-4 $R^7$;

$R^2$ is H; or $R^1$ and $R^2$ are taken together to form =O; or $R^1$ and $R^2$ are taken together with the carbon atom, to which they are both attached, to form a carbocycle or heterocycle wherein said carbocycle, and heterocycle are substituted with 1-4 $R^7$;

$R^3$ is selected from H, $C_{1-4}$ alkyl, $C_{2-4}$ alkenyl, —$(CR^4R^4)_{1-4}$—$NR^5R^5$, —$(CR^4R^4)_n C_{3-10}$ carbocycle and —$(CR^4R^4)_n$-4- to 15-membered heterocycle comprising carbon atoms and 1-4 heteroatoms selected from N, $NR^8$, O, and $S(O)_p$, wherein said alkyl, alkenyl, carbocycle, and heterocycle are substituted with 1-4 $R^7$; provided that $R^1$, $R^2$, and $R^3$ are not all H;

alternatively, $R^1$ and $R^3$ together form a fused ring;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$ and $R^5$ are taken together with the nitrogen atom to which they are attached to form a 4- to 15-membered heterocycle substituted with 1-4 $R^7$;

$R^6$, at each occurrence, is independently selected from H, halogen, $C_{1-6}$ alkyl, $C_{2-6}$ alkenyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —$C(=NH)NH_2$, a carbocycle, and a heterocycle, wherein said alkyl, alkenyl, alkoxy, alkylthio, haloalkyl, carbocycle, and heterocycle are substituted with 0-4 $R^9$;

R⁷, at each occurrence, is independently selected from H, =O, NO₂, halogen, $C_{1-7}$ alkyl, $C_{2-4}$ alkenyl, $C_{2-4}$ alkynyl, $C_{1-4}$ alkoxy, CN, OH, CHF₂, CF₃, —(CH₂)ₙ—CO₂H, —(CH₂)ₙ—CO₂($C_{1-4}$ alkyl), —(CH₂)ₙ—NR⁸R⁸, —NHCOH, —NHCO($C_{1-4}$ alkyl), —NHCOCF₃, —NHCO₂($C_{1-4}$ alkyl), —NHCO₂(CH₂)₂O($C_{1-4}$ alkyl), —NHCO₂(CH₂)₃O($C_{1-4}$ alkyl), —NHCO₂(CH₂)₂OH, —NHCO₂(CH₂)₂NH₂, —NHCO₂(CH₂)₂N($C_{1-4}$ alkyl)₂, —NHCO₂CH₂CO₂H, —CH₂NHCO₂($C_{1-4}$ alkyl), —NHC(O)NR⁸R⁸, —NHSO₂($C_{1-4}$ alkyl), —S(O)ₚ($C_{1-4}$ alkyl), —SO₂NH₂, —SO₂NH($C_{1-4}$ alkyl), —SO₂N($C_{1-4}$ alkyl)₂, —SO₂NH(CH₂)₂OH, —SO₂NH(CH₂)₂O($C_{1-4}$ alkyl), —(CH₂)ₙ—CONR⁸R⁸, —O(CH₂)ₙ-carbocycle, —O(CH₂)ₙ-heterocycle, —S(O)₂-carbocycle, —S(O)₂-heterocycle, —NHCO-carbocycle, —NHCO-heterocycle, —NHCOO(CH₂)ₙcarbocycle, —NHCOO(CH₂)ₙ-heterocycle, —CONH-carbocycle, —CONH-heterocycle, —(CH₂)ₙ-carbocycle, and —(CH₂)ₙ-heterocycle comprising carbon atoms and 1-4 heteroatoms selected from N, NR⁸, O, and S(O)ₚ, wherein said alkyl, alkenyl, alkynyl, alkoxy, carbocycle, and heterocycle are substituted with 0-4 R⁹;

R⁸, at each occurrence, is independently selected from H, $C_{1-6}$ alkyl, $C_{2-4}$ alkenyl, $C_{2-4}$ alkynyl, —(CH₂)ₙ—C(O)$C_{1-4}$alkyl, —(CH₂)ₙ—C(O)carbocycle, —(CH₂)ₙ—C(O)heterocycle, —(CH₂)ₙ—C(O)NRᵃRᵃ, —(CH₂)ₙ—NRC(O)$C_{1-4}$alkyl, —(CH₂)ₙ—C(O)OC$_{1-4}$alkyl, —(CH₂)ₙ—C(O)$C_{1-4}$alkyl, —(CH₂)ₙ—C(O)O(CH₂)ₙcarbocycle, —(CH₂)ₙ—C(O)O(CH₂)ₙ-heterocycle, —(CH₂)ₙ—SO₂alkyl, —(CH₂)ₙ SO₂carbocycle, —(CH₂)ₙ—SO₂heterocycle, —(CH₂)ₙ—SO₂NRᵃRᵃ, —(CH₂)ₙ-carbocycle, and —(CH₂)ₙ-heterocycle, wherein said alkyl, carbocycle, and heterocycle are substituted with 0-4 R⁹;

alternatively, R⁸ and R⁸ are taken together with the nitrogen atom to which they are attached to form a 4- to 10-membered heterocycle substituted with 0-4 R⁹;

R⁹, at each occurrence, is independently selected from halogen, OH, =O, CN, NO₂, $C_{1-4}$ alkyl, $C_{1-4}$ alkoxy, CO($C_{1-4}$ alkyl), CO₂H, CO₂($C_{1-4}$ alkyl), —(CHR¹⁰)ₙNRᵃRᵃ, S(O)ₚ($C_{1-4}$ alkyl), —(CHR¹⁰)ₙCONRᵃRᵃ, —(CHR¹⁰)ₙNRᵃCO($C_{1-4}$ alkyl), —(CHR¹⁰)ₙOCONRᵃ(CH₂)ₙCO₂R, S(O)ₚ$C_{1-4}$alkyl, S(O)ₚNRᵃRᵃ, —O(CHR¹⁰)ₙcarbocycle, —O(CHR¹⁰)ₙheterocycle, —O(CHR¹⁰)ₙNRᵃRᵃ, and —(CR¹⁰R¹⁰)ₙ-4- to 10-membered heterocycle, wherein said alkyl, alkoxy, carbocycle, and heterocycle are substituted with 0-4 $R^b$;

R¹⁰, at each occurrence, is independently selected from H and $C_{1-4}$ alkyl;

R¹¹ is independently selected from H and $C_{1-3}$ alkyl optionally substituted with halogen, $C_{1-4}$ alkoxy, —OH, CN, —CO₂H, —CO₂($C_{1-4}$ alkyl), —CO($C_{1-4}$ alkyl), —CONH₂, —CONH($C_{1-4}$ alkyl), and —CON($C_{1-4}$ alkyl)₂;

R¹² and R¹³ are independently selected from H, OH, —OC$_{1-3}$ alkyl substituted with 0-4 $R^d$, and $C_{1-3}$ alkyl with substituted with 0-4 $R^d$;

Rᵃ, at each occurrence, is independently selected from H, $C_{1-4}$ alkyl, —(CH₂)ₙOH, CO($C_{1-4}$ alkyl), COCF₃, CO₂($C_{1-4}$ alkyl), —CONH₂, —CONH—$C_{1-4}$ alkylene-CO₂($C_{1-4}$ alkyl), $C_{1-4}$ alkylene-CO₂($C_{1-4}$ alkyl), $R^c$, CO₂$R^c$, and CONH$R^c$; alternatively, Rᵃ and Rᵃ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, OCF₃, OC(O)$C_{1-4}$ alkyl, NH₂, NO₂, N($C_{1-4}$ alkyl)₂, CO($C_{1-4}$ alkyl), CO($C_{1-4}$ haloalkyl), CO₂H, CO₂($C_{1-4}$ alkyl), CONH₂, —CONH($C_{1-4}$ alkyl), —CON($C_{1-4}$ alkyl)₂, —CONH—$C_{1-4}$ alkylene-O($C_{1-4}$ alkyl), —CONH—$C_{1-4}$ alkylene-NH($C_{1-4}$ alkyl), —CONH—$C_{1-4}$ alkylene-N($C_{1-4}$ alkyl)₂, —$C_{1-4}$ alkylene-O—P(O)(OH)₂, —NHCO₂($C_{1-4}$ alkyl), —$R^c$, COR$^c$, CO₂$R^c$, and CONHR$^c$, wherein said alkyl and alkoxy are substituted with $R^d$;

$R^c$, at each occurrence, is independently selected from —(CH₂)ₙ—$C_{3-6}$ cycloalkyl, —(CH₂)ₙ-phenyl, and —(CH₂)ₙ-5- to 6-membered heterocycle containing carbon atoms and 1-4 heteroatoms selected from the group consisting of: N, NH, N($C_{1-4}$ alkyl), O, and S(O)ₚ, wherein each ring moiety is substituted with 0-2 $R^d$;

$R^d$, at each occurrence, is independently selected from =O, halogen, —OH, $C_{1-4}$ alkyl, NH₂, NH($C_{1-4}$ alkyl), N($C_{1-4}$ alkyl)₂, $C_{1-4}$ alkoxy, and —NHCO($C_{1-4}$ alkyl);

n, at each occurrence, is independently selected from 0, 1, 2, 3, and 4; and p, at each occurrence, is independently selected from 0, 1, and 2.

2. The compound of claim 1, having Formula (II):

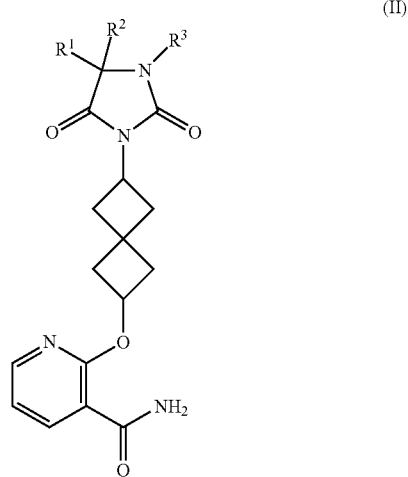

(II)

or a pharmaceutically acceptable salt thereof, wherein
R¹ is selected from H, $C_{1-7}$ alkyl, $C_{2-7}$ alkenyl, $C_{2-7}$ alkynyl, —(CR⁴R⁴)ₙNR⁵R⁵, —(CR⁴R⁴)ₙ$C_{3-10}$ carbocycle and —(CR⁴R⁴)ₙ-4- to 15-membered heterocycle comprising carbon atoms and 1-4 heteroatoms selected from N, NR⁸, O, and S(O)ₚ, wherein said alkyl, alkenyl, carbocycle, and heterocycle are substituted with 1-4 R⁷;

R² is H; or R¹ and R² are taken together to form =O; or R¹ and R² together with the carbon atom, to which they are both attached, to form $C_{3-6}$ cycloalkyl substituted with 1-4 R⁷;

R³ is H;

R⁴, at each occurrence, is independently selected from H and $C_{1-4}$ alkyl substituted with 0-4 R⁹;

$R^5$ and $R^5$ are taken together with the nitrogen atom to which they are attached to form a 4- to 15-membered heterocycle substituted with 1-4 $R^7$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, $-(CH_2)_n-CO_2H$, $-(CH_2)_n-CO_2(C_{1-4}$ alkyl), $-(CH_2)_n-NR^8R^8$, $-NHCOH$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-CH_2NHCO_2(C_{1-4}$ alkyl), $-NHC(O)NR^8R^8$, $-NHSO_2(C_{1-4}$ alkyl), $-S(O)_p(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-S(O)_2$-carbocycle, $S(O)_2$-heterocycle, $-NHCO$-carbocycle, $-NHCO$-heterocycle, $-CONH$-carbocycle, $-CONH$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, $-(CH_2)_n-C(O)C_{1-4}$alkyl, $-(CH_2)_n-C(O)$carbocycle, $-(CH_2)_n-C(O)$heterocycle, $-(CH_2)_n-C(O)NR^aR^a$, $-(CH_2)_n-NR^aC(O)C_{1-4}$alkyl, $-(CH_2)_n-C(O)OC_{1-4}$alkyl, $-(CH_2)_n-C(O)C_{1-4}$alkyl, $-(CH_2)_n-C(O)O$-carbocycle, $-(CH_2)_n-C(O)O$-heterocycle, $-(CH_2)_n-SO_2$alkyl, $-(CH_2)_n$ $SO_2$carbocycle, $-(CH_2)_n-SO_2$heterocycle, $-(CH_2)_n-SO_2NR^aR^a$, $-(CH_2)_n$-carbocycle, and $-(CH_2)_n$-heterocycle, wherein said alkyl, carbocycle, and heterocycle are substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), $-(CHR^{10})_n-NR^aR^a$, $S(O)_p(C_{1-4}$ alkyl), $-(CHR^{10})_n CONR^aR^a$, $-(CHR^{10})_n NR^aCO(C_{1-4}$ alkyl), $-(CHR^{10})_n OCONR^a(CH_2)_n CO_2R^a$, $S(O)_p C_{1-4}$alkyl, $S(O)_p NR^aR^a$, $-O(CHR^{10})_n$ carbocycle, $-O(CHR^{10})_n$ heterocycle, $-O(CHR^{10})_n NR^aR^a$, and $-(CR^{10}R^{10})_n$-4- to 10-membered heterocycle, wherein said alkyl, alkoxy, carbocycle, and alkyl are substituted with 0-4 $R^b$;

$R^{10}$, at each occurrence, is independently selected from H and $C_{1-4}$ alkyl;

$R^a$, at each occurrence, is independently selected from H, $C_{1-4}$ alkyl, $-(CH_2)_nOH$, $CO(C_{1-4}$ alkyl), $COCF_3$, $CO_2(C_{1-4}$ alkyl), $-CONH_2$, $-CONH-C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2H$, $CO_2(C_{1-4}$ alkyl), $CONH_2$, $-CONH(C_{1-4}$ alkyl), $-CON(C_{1-4}$ alkyl)$_2$, $-CONH-C_{1-4}$ alkylene-$O(C_{1-4}$ alkyl), $-CONH-C_{1-4}$ alkylene-$NH(C_{1-4}$ alkyl), $-CONH-C_{1-4}$ alkylene-$N(C_{1-4}$ alkyl)$_2$, $-C_{1-4}$ alkylene-$O-P(O)(OH)_2$, $-NHCO_2(C_{1-4}$ alkyl), $-R^c$, $COR^c$, $CO_2R^c$, and $CONHR^c$, wherein said alkyl and alkoxy are substituted with $R^d$;

$R^c$, at each occurrence, is independently selected from $-(CH_2)_n-C_{3-6}$ cycloalkyl, $-(CH_2)_n$-phenyl, and $-(CH_2)_n$-5- to 6-membered heterocycle containing carbon atoms and 1-4 heteroatoms selected from the group consisting of: N, NH, $N(C_{1-4}$ alkyl), O, and $S(O)_p$, wherein each ring moiety is substituted with 0-2 $R^d$;

$R^d$, at each occurrence, is independently selected from =O, halogen, $-OH$, $C_{1-4}$ alkyl, $NH_2$, $NH(C_{1-4}$ alkyl), $N(C_{1-4}$ alkyl)$_2$, $C_{1-4}$ alkoxy, and $-NHCO(C_{1-4}$ alkyl);

n, at each occurrence, is independently selected from 0, 1, 2, 3, and 4; and p, at each occurrence, is independently selected from 0, 1, and 2.

3. The compound of claim 2, having Formula (III):

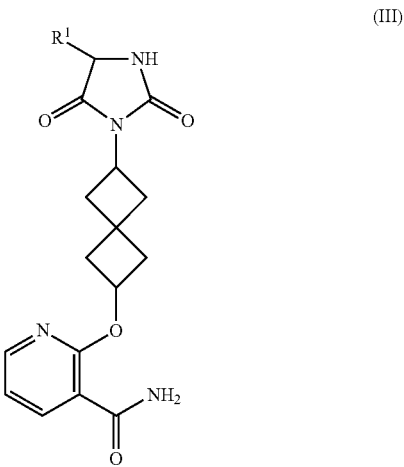

(III)

or a pharmaceutically acceptable salt thereof, wherein
$R^1$ is $-(CH_2)_{1-4}-C_{3-8}$ carbocycle wherein said carbocycle is selected from

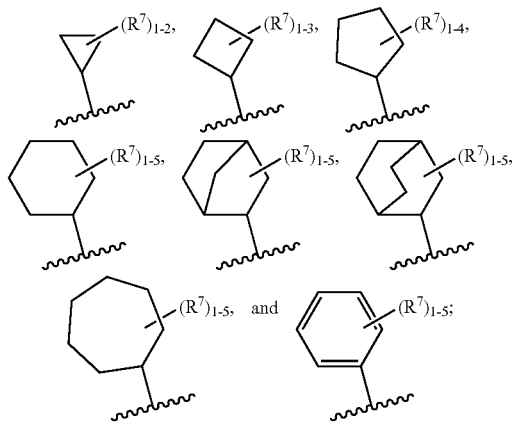

$R^7$, at each occurrence, is independently selected from H, =O, halogen, $C_{1-7}$ alkyl, $C_{1-4}$ alkoxy, CN, OH, $CHF_2$, $CF_3$, $-(CH_2)_n-CO_2H$, $-(CH_2)_n-CO_2(C_{1-4}$ alkyl), wherein said alkyl, alkoxy, are substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, and $CO_2(C_{1-4}$ alkyl); and n, at each occurrence, is independently selected from 0, 1, 2, 3, and 4.

4. The compound of claim 2, having Formula (III):

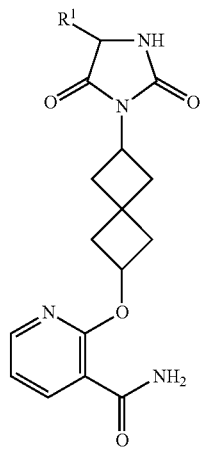

(III)

or a pharmaceutically acceptable salt thereof, wherein
R$^1$ is —(CH$_2$)$_{1-4}$-4- to 15-membered heterocycle selected from

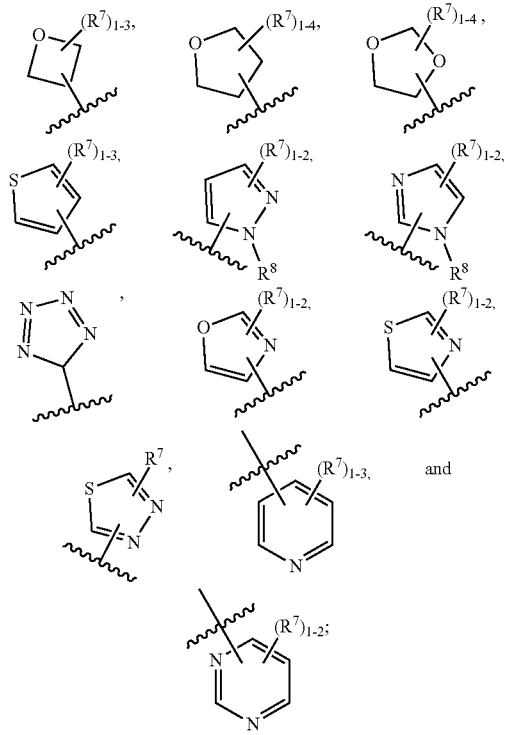

R$^7$, at each occurrence, is independently selected from H, =O, halogen, C$_{1-7}$ alkyl, C$_{2-4}$ alkenyl, C$_{2-4}$ alkynyl, C$_{1-4}$ alkoxy, CN, OH, CHF$_2$, CF$_3$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H and C$_{1-6}$ alkyl substituted with 0-4 R$^9$;

R$^9$, at each occurrence, is independently selected from halogen, OH, —O, CN, NO$_2$, C$_{1-4}$ alkyl, C$_{1-4}$ alkoxy, CO(C$_{1-4}$ alkyl), CO$_2$H, and CO$_2$(C$_{1-4}$ alkyl); and n, at each occurrence, is independently selected from 0, 1, 2, 3, and 4.

5. The compound of claim 2, having Formula (III):

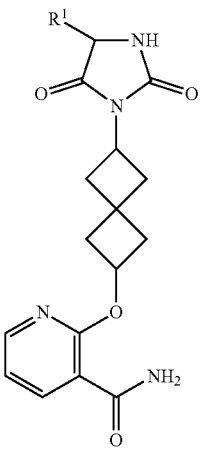

(III)

or a pharmaceutically acceptable salt thereof, wherein
R$^1$ is —(CH$_2$)$_{1-4}$NR$^5$R$^5$;
R$^5$ and R$^5$ are taken together with the nitrogen atom to which they are attached to form a 4- to 15-membered heterocycle selected from

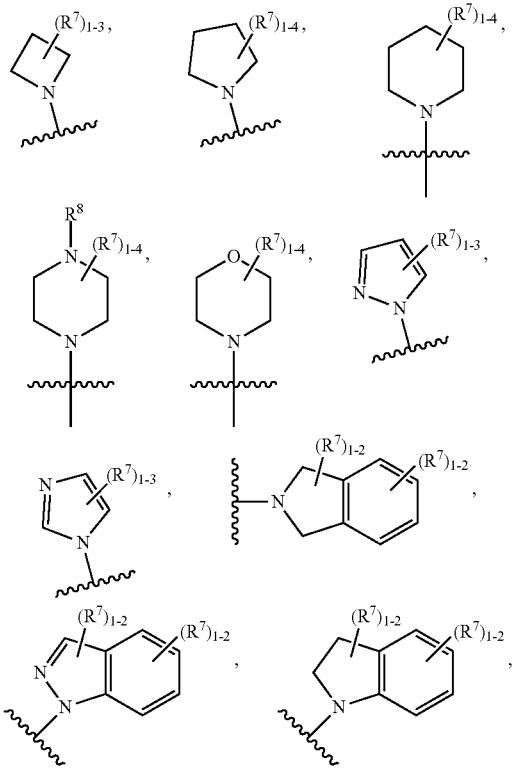

-continued

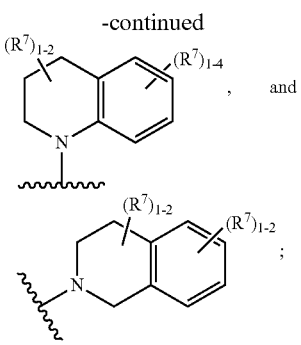
, and

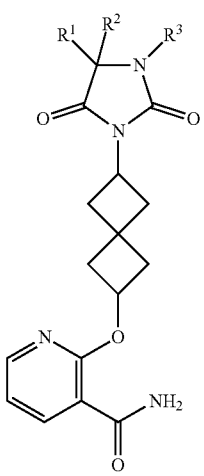
;

R⁷, at each occurrence, is independently selected from H, =O, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), wherein said alkyl, alkenyl, alkynyl, alkoxy, carbocycle, and heterocycle are substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, and $CO_2(C_{1-4}$ alkyl); and n, at each occurrence, is independently selected from 1, 2, 3, and 4.

6. The compound of claim 1, having Formula (II):

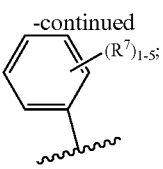

(II)

or a pharmaceutically acceptable salt thereof, wherein
$R^1$ is selected from H and —$(CH_2)_{1-4}$-phenyl;
$R^2$ is H; alternatively, $R^1$ and $R^2$ are taken together to form =O;
$R^3$ is selected from $C_{1-7}$ alkyl, —$(CH_2)_{1-4}NR^5R^5$, —$(CH_2)_nC_{3-8}$ carbocycle selected from

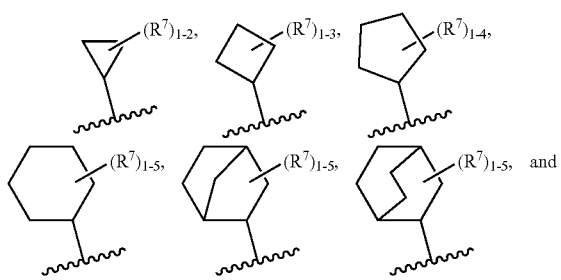

$R^5$ and $R^5$ are taken together with the nitrogen atom to which they are attached to form a 4- to 15-membered heterocycle selected from

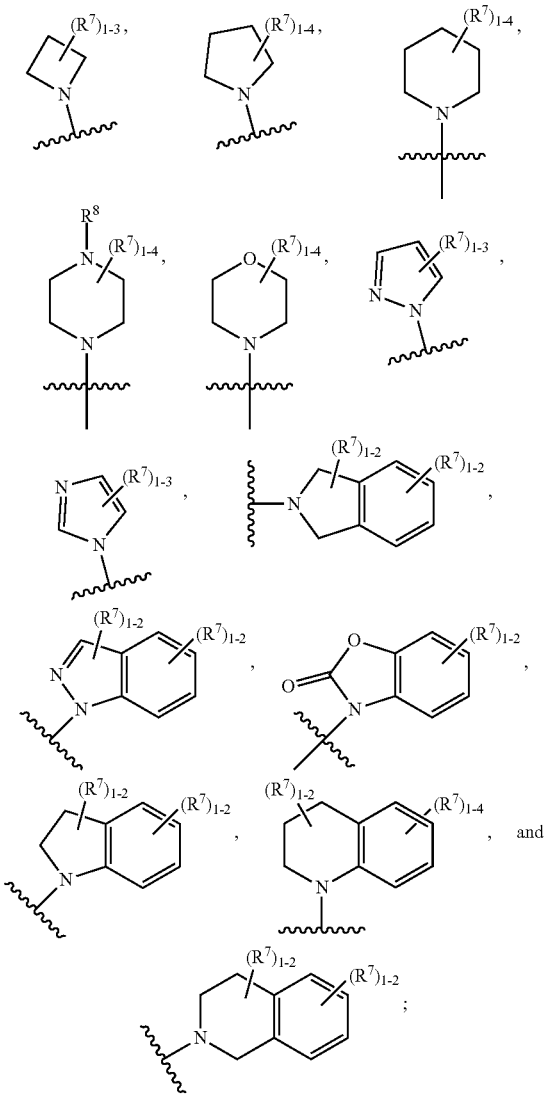

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$NHCO(C_{1-4}$ alkyl), —$NHCO_2(C_{1-4}$ alkyl), —$NHSO_2(C_{1-4}$ alkyl), —$S(O)_p$ $(C_{1-4}$ alkyl), —$SO_2NH_2$, —$SO_2NH(C_{1-4}$ alkyl), —$SO_2N(C_{1-4}$ alkyl)$_2$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

R⁹, at each occurrence, is independently selected from halogen, OH, =O, CN, $C_{1-4}$ alkyl, and $C_{1-4}$ alkoxy;

n, at each occurrence, is independently selected from 0, 1, 2, 3, and 4; and p, at each occurrence, is independently selected from 0, 1, and 2.

7. The compound of claim 1, having Formula (IV):

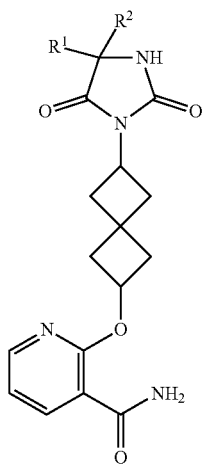

(IV)

or a pharmaceutically acceptable salt thereof, wherein $R^1$ and $R^2$ are taken together with the carbon atom they are both attached to form cyclobutyl, cyclopentyl, and cyclohexyl, wherein said cyclobutyl, cyclopentyl, and cyclohexyl are substituted with 1-4 $R^7$;

$R^7$, at each occurrence, is independently selected from H, =O, halogen, phenyl substituted with 0-4 $R^9$; and $R^9$, at each occurrence, is independently selected from halogen, OH, CN, $C_{1-4}$ alkyl, and $C_{1-4}$ alkoxy.

8. The compound of claim 1, having Formula (V):

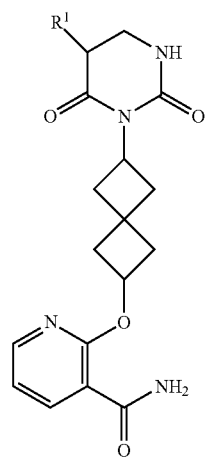

(V)

or a pharmaceutically acceptable salt thereof, wherein $R^1$ is $C_{1-7}$ alkyl substituted with 1-4 $R^7$;

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —NHCO($C_{1-4}$ alkyl), —NHCO₂($C_{1-4}$ alkyl), —NHSO₂($C_{1-4}$ alkyl), —S(O)$_p$($C_{1-4}$ alkyl), —SO₂NH₂, —SO₂NH($C_{1-4}$ alkyl), —SO₂N($C_{1-4}$ alkyl)₂, wherein said alkyl, alkenyl, alkynyl, and alkoxy are substituted with 0-4 $R^9$; and $R^9$, at each occurrence, is independently selected from halogen, OH, CN, $C_{1-4}$ alkyl, and $C_{1-4}$ alkoxy.

9. The compound of claim 1, having Formula (VI):

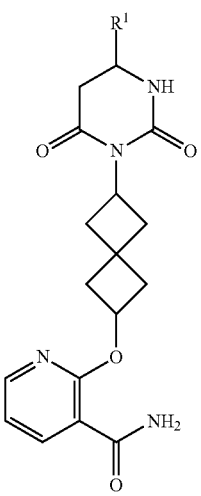

(VI)

or a pharmaceutically acceptable salt thereof, wherein $R^1$ is selected from $C_{1-7}$ alkyl, and —(CH₂)$_n$$C_{3-10}$ carbocycle and —(CH₂)$_n$-4- to 15-membered heterocycle comprising carbon atoms and 1-4 heteroatoms selected from N, $NR^8$, O, and S(O)$_p$, wherein said alkyl, alkenyl, carbocycle, and heterocycle are substituted with 1-4 $R^7$;

$R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —NHCO($C_{1-4}$ alkyl), —NHCO₂($C_{1-4}$ alkyl), —NHSO₂($C_{1-4}$ alkyl), —S(O)$_p$($C_{1-4}$ alkyl), —SO₂NH₂, —SO₂NH($C_{1-4}$ alkyl), —SO₂N($C_{1-4}$ alkyl)₂, —O(CH₂)$_n$-carbocycle, —O(CH₂)$_n$-heterocycle, —NHCO-carbocycle, —NHCO-heterocycle, —(CH₂)$_n$-carbocycle, and —(CH₂)$_n$-heterocycle comprising carbon atoms and 1-4 heteroatoms selected from N, $NR^8$, O, and S(O)$_p$, wherein said alkyl, alkenyl, alkynyl, alkoxy, carbocycle, and heterocycle are substituted with 0-4 $R^9$;

$R^9$, at each occurrence, is independently selected from halogen, OH, =O, CN, $C_{1-4}$ alkyl, and $C_{1-4}$ alkoxy;

n, at each occurrence, is independently selected from 0, 1, 2, 3, and 4; and p, at each occurrence, is independently selected from 0, 1, and 2.

10. The compound of claim 1, having Formula (VII):

(VII)

or a pharmaceutically acceptable salt thereof, wherein $R^3$ is selected from $C_{1-7}$ alkyl substituted with 1-4 $R^7$ and —$(CH_2)_n C_{3-8}$ carbocycle selected from $R^7$, at each occurrence, is independently selected from H, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$NHCO(C_{1-4}$ alkyl), —$NHCO_2(C_{1-4}$ alkyl), —$NHSO_2(C_{1-4}$ alkyl), —$S(O)_p$ $(C_{1-4}$ alkyl), —$SO_2NH_2$, —$SO_2NH(C_{1-4}$ alkyl), —$SO_2N(C_{1-4}$ alkyl$)_2$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^9$, at each occurrence, is independently selected from halogen, OH, =O, CN, and $C_{1-4}$ alkyl, $C_{1-4}$ alkoxy;

n, at each occurrence, is independently selected from 0, 1, 2, 3, and 4; and p, at each occurrence, is independently selected from 0, 1, and 2.

11. The compound of claim 1, having Formula (VIII):

(VIII)

or a pharmaceutically acceptable salt thereof, wherein $R^1$ and $R^3$ form a fused 5- to 6-membered ring.

12. The compound of claim 6, or a pharmaceutically acceptable salt thereof, wherein $R^3$ is $R^7$, at each occurrence, is independently selected from H, halogen, $C_{1-7}$ alkyl, $C_{1-4}$ alkoxy, CN, OH, $CHF_2$, $CF_3$, —$S(O)_p(C_{1-4}$ alkyl), —$SO_2NH_2$, —$SO_2NH(C_{1-4}$ alkyl), —$SO_2N(C_{1-4}$ alkyl$)_2$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkoxy, carbocycle, and heterocycle are substituted with 0-4 $R^9$;

$R^9$, at each occurrence, is independently selected from halogen, OH, =O, CN, $C_{1-4}$ alkyl, and $C_{1-4}$ alkoxy;

n, at each occurrence, is independently selected from 0, 1, 2, 3, and 4; and p, at each occurrence, is independently selected from 0, 1, and 2.

13. A pharmaceutical composition comprising one or more compounds according to claim 1 and a pharmaceutically acceptable carrier or diluent.

14. A compound according to claim 1 for prophylaxis and/or treatment of disorders associated with aberrant Rho kinase activity.

15. The compound of claim 14, wherein said disorder is selected from the group consisting of a cardiovascular disorder, a smooth muscle related disorder, a fibrotic disease, an inflammatory disease, neuropathic disorders, oncologic disorders, and an autoimmune disorder.

16. The compound of claim 15, wherein said cardiovascular disorder is selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension.

17. A compound, or a pharmaceutically acceptable salt thereof, selected from:

2-(((αR)-6-(4-isobutyl-2,5-dioxoimidazolidin-1-yl)spiro[3.3]heptan-2-yl)oxy)nicotinamide;
2-{[(αR)-6-[4-(cyclohexylmethyl)-2,5-dioxoimidazolidin-1-yl]spiro[3.3]heptan-2-yl]oxy}pyridine-3-carboxamide;
2-{[6-(2,5-dioxo-3-phenylimidazolidin-1-yl)spiro[3.3]heptan-2-yl]oxy}pyridine-3-carboxamide;
2-{[(αR)-6-[4-(2-cyclohexylethyl)-2,5-dioxoimidazolidin-1-yl]spiro[3.3]heptan-2-yl]oxy}pyridine-3-carboxamide;
2-{[(αR)-6-[2,5-dioxo-4-(2-phenylethyl)imidazolidin-1-yl]spiro[3.3]heptan-2-yl]oxy}pyridine-3-carboxamide;
2-{[(αR)-6-(4-cyclohexylmethyl-2,5-dioxoimidazolidin-1-yl)spiro[3.3]heptan-2-yl]oxy}pyridine-3-carboxamide;
2-{[(αR)-6-(4-tert-butyl-2,5-dioxoimidazolidin-1-yl)spiro[3.3]heptan-2-yl]oxy}pyridine-3-carboxamide;
2-{[(αR)-6-{2,4-dioxo-1,3-diazaspiro[4.4]nonan-3-yl}spiro[3.3]heptan-2-yl]oxy}pyridine-3-carboxamide;
2-{[(αR)-6-(4-tert-butoxymethyl-2,5-dioxoimidazolidin-1-yl)spiro[3.3]heptan-2-yl]oxy}pyridine-3-carboxamide;
2-{[6-(3-benzyl-2,5-dioxoimidazolidin-1-yl)spiro[3.3]heptan-2-yl]oxy}pyridine-3-carboxamide;
2-{[(αR)-6-[2,5-dioxo-3-(2-phenylethyl)imidazolidin-1-yl]spiro[3.3]heptan-2-yl]oxy}pyridine-3-carboxamide;
2-{[(αR)-6-(4-(2-phenylethyl)-2,5-dioxoimidazolidin-1-yl)spiro[3.3]heptan-2-yl]oxy}pyridine-3-carboxamide;
2-{[(αR)-6-[3-(2-methylpropyl)-2,5-dioxoimidazolidin-1-yl]spiro[3.3]heptan-2-yl]oxy}pyridine-3-carboxamide;
2-{[(αR)-6-[2,5-dioxo-4-(prop-2-yn-1-yl)imidazolidin-1-yl]spiro[3.3]heptan-2-yl]oxy}pyridine-3-carboxamide;
tert-butyl N-(3-{2,5-dioxo-1-[(aR)-6-[(3-carbamoylpyridin-2-yl)oxy]spiro[3.3]heptan-2-yl]imidazolidin-4-yl}propyl)carbamate;
2-{[(αR)-6-{6,8-dioxo-5,7-diazaspiro[3.4]octan-7-yl}spiro[3.3]heptan-2-yl]oxy}pyridine-3-carboxamide;
2-{[(αR)-6-{1,3-dioxo-hexahydro-1H-piperidino[1,2-c]imidazolidin-2-yl}spiro[3.3]heptan-2-yl]oxy}pyridine-3-carboxamide;
2-{[(αR)-6-[2,5-dioxo-4-(2-hydroxyethyl)imidazolidin-1-yl]spiro[3.3]heptan-2-yl]oxy}pyridine-3-carboxamide;
2-{[(αR)-6-[2,5-dioxo-4-(1-methyl-4-imidazylmethyl)imidazolidin-1-yl]spiro[3.3]heptan-2-yl]oxy}pyridine-3-carboxamide;
tert-butyl N-(2-{2,5-dioxo-1-[(αR)-6-[(3-carbamoylpyridin-2-yl)oxy]spiro[3.3]heptan-2-yl]imidazolidin-4-yl}ethyl)carbamate;
tert-butyl N-(2-{2,5-dioxo-1-[(αR)-6-[(3-carbamoylpyridin-2-yl)oxy]spiro[3.3]heptan-2-yl]imidazolidin-4-yl}ethyl)carbamate;
2-{[(αR)-6-{4-[(1H-imidazol-4-yl)methyl]-2,5-dioxoimidazolidin-1-yl}spiro[3.3]heptan-2-yl]oxy}pyridine-3-carboxamide;
2-{[(αR)-6-{1,3-dioxo-hexahydro-1H-pyrrolo[1,2-c]imidazolidin-2-yl}spiro[3.3]heptan-2-yl]oxy}pyridine-3-carboxamide;
2-(((R)-6-((S)-4-benzyl-2,5-dioxoimidazolidin-1-yl)spiro[3.3]heptan-2-yl)oxy)nicotinamide;
2-{[(αR)-6-[(4S)-4-(2,2-dimethylpropyl)-2,5-dioxoimidazolidin-1-yl]spiro[3.3]heptan-2-yl]oxy}pyridine-3-carboxamide;
2-{[(αR)-6-[(4S)-4-(cyclopropylmethyl)-2,5-dioxoimidazolidin-1-yl]spiro[3.3]heptan-2-yl]oxy}pyridine-3-carboxamide;
2-{[(αR)-6-[(4S)-4-[(2S)-butan-2-yl]-2,5-dioxoimidazolidin-1-yl]spiro[3.3]heptan-2-yl]oxy}pyridine-3-carboxamide;
2-{[(αR)-6-[(4S)-4-butyl-2,5-dioxoimidazolidin-1-yl]spiro[3.3]heptan-2-yl]oxy}pyridine-3-carboxamide;
2-{[(αR)-6-[2,5-dioxo-4-(3,3,3-trifluoropropyl)imidazolidin-1-yl]spiro[3.3]heptan-2-yl]oxy}pyridine-3-carboxamide;
2-{[(αR)-6-[(4S)-4-[2-(methylsulfanyl)ethyl]-2,5-dioxoimidazolidin-1-yl]spiro[3.3]heptan-2-yl]oxy}pyridine-3-carboxamide;
2-{[(αR)-6-[(4S)-2,5-dioxo-4-propylimidazolidin-1-yl]spiro[3.3]heptan-2-yl]oxy}pyridine-3-carboxamide;
2-{[(αR)-6-[(4S)-2,5-dioxo-4-(2,2,2-trifluoroethyl)imidazolidin-1-yl]spiro[3.3]heptan-2-yl]oxy}pyridine-3-carboxamide;
2-{[(αR)-6-[(4S)-4-[2-(benzyloxy)ethyl]-2,5-dioxoimidazolidin-1-yl]spiro[3.3]heptan-2-yl]oxy}pyridine-3-carboxamide;
2-({6-[(4R)-4-benzyl-2,5-dioxoimidazolidin-1-yl]spiro[3.3]heptan-2-yl}oxy)pyridine-3-carboxamide;
2-{[(αR)-6-[(4S)-4-ethyl-2,5-dioxoimidazolidin-1-yl]spiro[3.3]heptan-2-yl]oxy}pyridine-3-carboxamide;
2-{[(αR)-6-[(4S)-4-(methoxymethyl)-2,5-dioxoimidazolidin-1-yl]spiro[3.3]heptan-2-yl]oxy}pyridine-3-carboxamide;
2-(((R)-6-(4-(2-cyclopropylethyl)-2,5-dioxoimidazolidin-1-yl)spiro[3.3]heptan-2-yl)oxy)nicotinamide;
2-{[(αR)-6-[4-(2-ethylbutyl)-2,5-dioxoimidazolidin-1-yl]spiro[3.3]heptan-2-yl]oxy}pyridine-3-carboxamide;
2-{[(αR)-6-[4-(2-methylpentyl)-2,5-dioxoimidazolidin-1-yl]spiro[3.3]heptan-2-yl]oxy}pyridine-3-carboxamide;
2-{[(αR)-6-[4-(cyclopentylmethyl)-2,5-dioxoimidazolidin-1-yl]spiro[3.3]heptan-2-yl]oxy}pyridine-3-carboxamide;
2-{[(αR)-6-[4-(2-methylbutyl)-2,5-dioxoimidazolidin-1-yl]spiro[3.3]heptan-2-yl]oxy}pyridine-3-carboxamide;
2-{[(αR)-6-[2,5-dioxo-4-(4,4,4-trifluorobutyl)imidazolidin-1-yl]spiro[3.3]heptan-2-yl]oxy}pyridine-3-carboxamide;
2-{[(αR)-6-[4-(2-cycloheptylethyl)-2,5-dioxoimidazolidin-1-yl]spiro[3.3]heptan-2-yl]oxy}pyridine-3-carboxamide;
2-{[(αR)-6-[4-(2-methylpropyl)-2,5-dioxoimidazolidin-1-yl]spiro[3.3]heptan-2-yl]oxy}pyridine-3-carboxamide;
2-{[(αR)-6-[4-(cyclopentylmethyl)-2,5-dioxoimidazolidin-1-yl]spiro[3.3]heptan-2-yl]oxy}pyridine-3-carboxamide;
2-{[(αR)-6-{4-[(3,3-difluorocyclobutyl)methyl]-2,5-dioxoimidazolidin-1-yl}spiro[3.3]heptan-2-yl]oxy}pyridine-3-carboxamide;
2-{[(αR)-6-{4-[(3,3,3,3',3',3'-hexafluoroisobutyl]-2,5-dioxoimidazolidin-1-yl}spiro[3.3]heptan-2-yl]oxy}pyridine-3-carboxamide;
2-{[(αR)-6-[4-(2-ethylbutyl)-2,5-dioxoimidazolidin-1-yl]spiro[3.3]heptan-2-yl]oxy}pyridine-3-carboxamide;
2-{[(αR)-6-[2,5-dioxo-4-(3,3,3-trifluoropropyl)imidazolidin-1-yl]spiro[3.3]heptan-2-yl]oxy}pyridine-3-carboxamide;

2-{[(αR)-6-{2,5-dioxo-4-[2-(2,2,2-trifluoroethoxy)ethyl] imidazolidin-1-yl}spiro[3.3]heptan-2-yl]oxy}pyridine-3-carboxamide;
2-{[(αR)-6-[2,5-dioxo-4-(pentan-3-yl)imidazolidin-1-yl] spiro[3.3]heptan-2-yl]oxy}pyridine-3-carboxamide;
2-{[(R)-6-[4-(cyclopentylmethyl)-2,5-dioxoimidazolidin-1-yl]spiro[3.3]heptan-2-yl]oxy}pyridine-3-carboxamide;
2-{[(αR)-6-[4-(2-cycloheptylethyl)-2,5-dioxoimidazolidin-1-yl]spiro[3.3]heptan-2-yl]oxy}pyridine-3-carboxamide;
2-{[(αR)-6-[4-(3-methylbutyl)-2,5-dioxoimidazolidin-1-yl]spiro[3.3]heptan-2-yl]oxy}pyridine-3-carboxamide;
2-{[(αR)-6-{2,5-dioxo-4-[(oxolan-2-yl)methyl]imidazolidin-1-yl}spiro[3.3]heptan-2-yl]oxy}pyridine-3-carboxamide;
2-{[(αR)-6-{2,5-dioxo-4-[3,3,3-trifluoro-2-(trifluoromethyl)propyl]imidazolidin-1-yl}spiro[3.3]heptan-2-yl] oxy}pyridine-3-carboxamide;
2-{[(αR)-6-{2,5-dioxo-4-[2-(trifluoromethoxy)ethyl]imidazolidin-1-yl}spiro[3.3]heptan-2-yl]oxy}pyridine-3-carboxamide;
2-{[(αR)-6-[4-(2-hydroxy-2-methylpropyl)-2,5-dioxoimidazolidin-1-yl]spiro[3.3]heptan-2-yl]oxy}pyridine-3-carboxamide;
2-{[(αR)-6-{2,5-dioxo-4-[2-(trifluoromethoxy)ethyl]imidazolidin-1-yl}spiro[3.3]heptan-2-yl]oxy}pyridine-3-carboxamide;
2-{[(αR)-6-[2,5-dioxo-4-(4,4,4-trifluorobutyl)imidazolidin-1-yl]spiro[3.3]heptan-2-yl]oxy}pyridine-3-carboxamide;
2-{[(αR)-6-{2,5-dioxo-4-[2-(2,2,2-trifluoroethoxy)ethyl] imidazolidin-1-yl}spiro[3.3]heptan-2-yl]oxy}pyridine-3-carboxamide;
2-{[(αR)-6-[4-(3-hydroxy-3-methylbutyl)-2,5-dioxoimidazolidin-1-yl]spiro[3.3]heptan-2-yl]oxy}pyridine-3-carboxamide;
2-{[(αR)-6-[3-(cyclobutylmethyl)-2,4,5-trioxoimidazolidin-1-yl]spiro[3.3]heptan-2-yl]oxy}pyridine-3-carboxamide;
2-{[(αR)-6-{2,5-dioxo-4-[(oxolan-2-yl)methyl]imidazolidin-1-yl}spiro[3.3]heptan-2-yl]oxy}pyridine-3-carboxamide;
2-{[(αR)-6-[3-(3-methylbutyl)-2,4,5-trioxoimidazolidin-1-yl]spiro[3.3]heptan-2-yl]oxy}pyridine-3-carboxamide;
2-{[(αR)-6-[2,5-dioxo-4-(3-sulfamoylpropyl)imidazolidin-1-yl]spiro[3.3]heptan-2-yl]oxy}pyridine-3-carboxamide;
2-{[(αR)-6-[3-(2-methylpropyl)-2,4,5-trioxoimidazolidin-1-yl]spiro[3.3]heptan-2-yl]oxy}pyridine-3-carboxamide;
2-(((R)-6-(4-((1-adamantyl)methyl)-2,5-dioxoimidazolidin-1-yl)spiro[3.3]heptan-2-yl)oxy)nicotinamide;
2-{[(αR)-6-[4-({bicyclo[2.2.1]heptan-2-yl}methyl)-2,5-dioxoimidazolidin-1-yl]spiro[3.3]heptan-2-yl] oxy}pyridine-3-carboxamide;
2-{[(αR)-6-[4-({bicyclo[2.2.2]octan-2-yl}methyl)-2,5-dioxoimidazolidin-1-yl]spiro[3.3]heptan-2-yl] oxy}pyridine-3-carboxamide;
2-{[(αR)-6-[2,5-dioxo-4-(4,4,4-trifluoro-3-methylbutyl) imidazolidin-1-yl]spiro[3.3]heptan-2-yl]oxy}pyridine-3-carboxamide;
2-{[(αR)-6-{4-[(1,5-dimethyl-1H-pyrazol-4-yl)methyl]-2,5-dioxoimidazolidin-1-yl}spiro[3.3]heptan-2-yl] oxy}pyridine-3-carboxamide;
2-{[(αR)-6-{2,5-dioxo-4-[(pyridin-4-yl)methyl]imidazolidin-1-yl}spiro[3.3]heptan-2-yl]oxy}pyridine-3-carboxamide;
2-(((R)-6-((S)-2,6-dioxo-4-phenethyltetrahydropyrimidin-1(2H)-yl)spiro[3.3]heptan-2-yl)oxy)nicotinamide
2-{[(αR)-6-[(4R)-4-[(2S)-butan-2-yl]-2,6-dioxo-1,3-diazinan-1-yl]spiro[3.3]heptan-2-yl]oxy}pyridine-3-carboxamide;
2-{[(αR)-6-(4-benzyl-2,6-dioxo-1,3-diazinan-1-yl)spiro [3.3]heptan-2-yl]oxy}pyridine-3-carboxamide;
2-{[(αR)-6-[(4R)-4-(3-bromophenyl)-2,6-dioxo-1,3-diazinan-1-yl]spiro[3.3]heptan-2-yl]oxy}pyridine-3-carboxamide;
2-{[(αR)-6-[(4R)-2,6-dioxo-4-(prop-2-en-1-yl)-1,3-diazinan-1-yl]spiro[3.3]heptan-2-yl]oxy}pyridine-3-carboxamide;
2-(((R)-6-(5-isobutyl-2,6-dioxotetrahydropyrimidin-1 (2H)-yl)spiro[3.3]heptan-2-yl)oxy)nicotinamide;
2-(((aR)-6-(3-(3-chlorophenyl)-2,5-dioxoimidazolidin-1-yl)spiro[3.3]heptan-2-yl)oxy)nicotinamide;
2-(((αR)-6-(3-(2-(difluoromethoxy)phenyl)-2,5-dioxoimidazolidin-1-yl)spiro[3.3]heptan-2-yl)oxy)nicotinamide;
2-(((αR)-6-(2,5-dioxo-3-(3-(trifluoromethyl)phenyl)imidazolidin-1-yl)spiro[3.3]heptan-2-yl)oxy)nicotinamide;
2-(((αR)-6-(2,5-dioxo-3-(4-phenoxyphenyl)imidazolidin-1-yl)spiro[3.3]heptan-2-yl)oxy)nicotinamide;
2-(((αR)-6-(3-(4-benzylphenyl)-2,5-dioxoimidazolidin-1-yl)spiro[3.3]heptan-2-yl)oxy)nicotinamide;
2-(((αR)-6-(3-(3-fluorophenyl)-2,5-dioxoimidazolidin-1-yl)spiro[3.3]heptan-2-yl)oxy)nicotinamide;
2-(((αR)-6-(2,5-dioxo-3-(4-(trifluoromethoxy)phenyl) imidazolidin-1-yl)spiro[3.3]heptan-2-yl)oxy)nicotinamide;
2-(((αR)-6-(2,5-dioxo-3-(4-(trifluoromethyl)phenyl)imidazolidin-1-yl)spiro[3.3]heptan-2-yl)oxy)nicotinamide;
2-(((αR)-6-(3-(3-(2-hydroxy-2-methylpropoxy)phenyl)-2,5-dioxoimidazolidin-1-yl)spiro[3.3]heptan-2-yl)oxy) nicotinamide;
2-(((αR)-6-(3-(3-(methylsulfonyl)phenyl)-2,5-dioxoimidazolidin-1-yl)spiro[3.3]heptan-2-yl)oxy)nicotinamide;
2-(((αR)-6-(4-((E)-2-methyl-3-phenylallyl)-2,5-dioxoimidazolidin-1-yl)spiro[3.3]heptan-2-yl)oxy)nicotinamide;
2-(((αR)-6-(4-(2-methyl-3-phenylpropyl)-2,5-dioxoimidazolidin-1-yl)spiro[3.3]heptan-2-yl)oxy)nicotinamide;
2-(((αR)-6-((S)-2,5-dioxo-4-((R)-3,3,3-trifluoro-2-methylpropyl)imidazolidin-1-yl)spiro[3.3]heptan-2-yl)oxy) nicotinamide;
2-(((αR)-6-((S)-2,5-dioxo-4-((S)-3,3,3-trifluoro-2-methylpropyl)imidazolidin-1-yl)spiro[3.3]heptan-2-yl)oxy) nicotinamide;
2-(((αR)-6-(2,5-dioxo-4-(2-phenyl-2-methylpropyl)imidazolidin-1-yl)spiro[3.3]heptan-2-yl)oxy)nicotinamide;
2-(((αR)-6-((S)-2,5-dioxo-4-(2-phenyl-propyl)imidazolidin-1-yl)spiro[3.3]heptan-2-yl)oxy)nicotinamide;
2-(((αR)-6-((R)-2,5-dioxo-4-(2-phenyl-propyl)imidazolidin-1-yl)spiro[3.3]heptan-2-yl)oxy)nicotinamide;
2-(((αR)-6-((R)-2,5-dioxo-4-(trans-4-(beznylcarbamoyl)-cyclohex-1-ylmethyl)imidazolidin-1-yl)spiro[3.3]heptan-2-yl)oxy)nicotinamide;

2-(((R)-6-(2,5-dioxo-4-(N-benzyloxycarbonylpiperidin-4-ylmethyl)imidazolidin-1-yl)spiro[3.3]heptan-2-yl)oxy)nicotinamide;

Benzyl 3-((1-((aR)-6-((3-carbamoylpyridin-2-yl)oxy)spiro[3.3]heptan-2-yl)-2,5-dioxoimidazolidin-4-yl)methyl)-8-azabicyclo[3.2.1]octane-8-carboxylate;

2-(((R)-6-(2,5-dioxo-4-((trans-4-benzylaminocyclohex-1-yl)methylene)-2,5-dioxoimidazolidin-1-yl)spiro[3.3]heptan-2-yl)oxy)nicotinamide;

2-(((αR)-6-(2,5-dioxo-4-(N-benzoylpiperidin-4-ylmethyl)imidazolidin-1-yl)spiro[3.3]heptan-2-yl)oxy)nicotinamide; and 2-(((R)-6-((3R)-2,5-dioxo-3-(3,3,3-trifluoro-2-methylpropyl)pyrrolidin-1-yl)spiro[3.3]heptan-2-yl)oxy)-6-methoxynicotinamide.

* * * * *